United States Patent
Hegmans et al.

(10) Patent No.: US 9,714,271 B2
(45) Date of Patent: *Jul. 25, 2017

(54) CYCLOSPORINE ANALOGUE MOLECULES MODIFIED AT AMINO ACID 1 AND 3

(71) Applicant: ContraVir Pharmaceuticals, Inc., Edison, NJ (US)

(72) Inventors: Alexander Hegmans, Edmonton (CA); Bruce W. Fenske, Edmonton (CA); Dan J. Trepanier, Edmonton (CA); Mark D. Abel, Edmonton (CA); Daren R. Ure, Edmonton (CA); Shin Sugiyama, Edmonton (CA)

(73) Assignee: ContraVir Pharmaceuticals, Inc., Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/928,885

(22) Filed: Oct. 30, 2015

(65) Prior Publication Data

US 2016/0207961 A1 Jul. 21, 2016

Related U.S. Application Data

(63) Continuation of application No. 13/994,707, filed as application No. PCT/CA2011/050773 on Dec. 14, 2011, now Pat. No. 9,200,038.

(60) Provisional application No. 61/423,576, filed on Dec. 15, 2010.

(51) Int. Cl.
*A61K 38/13* (2006.01)
*C07K 7/64* (2006.01)
*A61K 38/00* (2006.01)

(52) U.S. Cl.
CPC .............. *C07K 7/645* (2013.01); *A61K 38/13* (2013.01); *A61K 38/00* (2013.01)

(58) Field of Classification Search
CPC .................................. A61K 38/13; C07K 7/645
See application file for complete search history.

(56) References Cited

U.S. PATENT DOCUMENTS

| | | | |
|---|---|---|---|
| 4,108,985 A | 8/1978 | Ruegger et al. | |
| 4,210,581 A | 7/1980 | Ruegger et al. | |
| 4,220,641 A | 9/1980 | Traber et al. | |
| 4,288,431 A | 9/1981 | Traber et al. | |
| 4,289,851 A | 9/1981 | Traber et al. | |
| 4,384,996 A | 5/1983 | Bollinger et al. | |
| 4,396,542 A | 8/1983 | Wenger | |
| 4,554,351 A | 11/1985 | Wenger | |
| 4,639,434 A | 1/1987 | Wenger et al. | |
| 4,703,033 A | 10/1987 | Seebach | |
| 4,764,503 A | 8/1988 | Wenger | |
| 4,771,122 A | 9/1988 | Seebach | |
| 4,798,823 A | 1/1989 | Witzel | |
| 4,885,276 A | 12/1989 | Witzel | |
| 4,914,188 A | 4/1990 | Dumont et al. | |
| 5,079,341 A | 1/1992 | Galpin et al. | |
| 5,116,816 A | 5/1992 | Dreyfuss et al. | |
| 5,122,511 A | 6/1992 | Patchett et al. | |
| 5,214,130 A | 5/1993 | Patchett et al. | |
| 5,227,467 A | 7/1993 | Durette et al. | |
| 5,236,899 A | 8/1993 | Durette | |
| 5,284,826 A | 2/1994 | Eberle | |
| 5,318,901 A | 6/1994 | Patchett et al. | |
| 5,350,574 A | 9/1994 | Erlanger et al. | |
| 5,405,785 A | 4/1995 | Erlanger et al. | |
| 5,525,590 A | 6/1996 | Bollinger et al. | |
| 5,604,092 A | 2/1997 | Erlanger et al. | |
| 5,639,852 A | 6/1997 | Rich et al. | |
| 5,643,870 A | 7/1997 | Boelsterli et al. | |

(Continued)

FOREIGN PATENT DOCUMENTS

| | | |
|---|---|---|
| EP | 194972 A2 | 9/1986 |
| EP | 296122 A2 | 12/1988 |

(Continued)

OTHER PUBLICATIONS

Aebi J.D. et al., Sythesis, conformation and immunosuppressive activity of a conformationally restricted cyclosporine lactam analogue, J. Med. Chem. 1998, vol. 31, pp. 1805-1815, ISSN: 002-2633; 11 pages.

Argaud, L, et al., "Specific inhibition of the mitochondrial permeability transition prevents lethal reperfusion injury", Journal of Molecular and Cell Cardiology, 2005, pp. 367-374, 8 pages.

Arora K., et al., "Extracellular cyclophilins contribute to the regulation of inflammatory responses", Journal of Immunology, 2005, pp. 517-522, 5 pages.

Balsley MA, et al. "A cell-impermeable cyclosporine a derivative reduces pathology in a mouse model of allergic lung inflammation", Journal of Immunology, 2010, pp. 7663-7670, 8 pages.

Basic Principles of Organic Chemistry, Second Edition, Roberts and Caserio. 1997, p. 615.

(Continued)

*Primary Examiner* — Jeffrey E Russel
(74) *Attorney, Agent, or Firm* — Cooley LLP; Ivor R. Elrifi; Heidi A. Erlacher

(57) ABSTRACT

Analogs of cyclosporin-A are disclosed comprising modifications of the substituents as the positions of amino acids 1 and 3, according to the following Formula. The disclosed compounds include compounds having affinity for cyclophilin, including cyclophilin-A, and reduced immunosuppressivity in comparison with cyclosporin-A and analogs thereof modified solely at position 1.

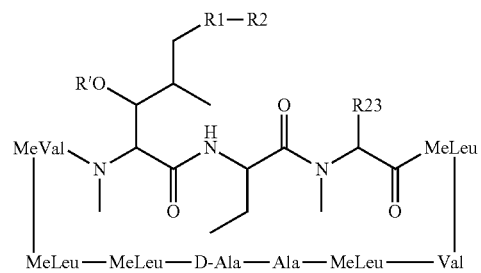

39 Claims, 3 Drawing Sheets

(56) References Cited

U.S. PATENT DOCUMENTS

| | | | |
|---|---|---|---|
| 5,767,069 A | 6/1998 | Ko et al. | |
| 5,798,823 A | 8/1998 | Kudo | |
| 5,948,693 A | 9/1999 | Rich et al. | |
| 5,948,755 A | 9/1999 | Barriere et al. | |
| 5,948,884 A | 9/1999 | Luchinger | |
| 5,965,527 A | 10/1999 | Barriere et al. | |
| 5,972,924 A | 10/1999 | Keep et al. | |
| 5,977,067 A | 11/1999 | Evers et al. | |
| 5,981,479 A | 11/1999 | Ko et al. | |
| 5,990,274 A | 11/1999 | Wang | |
| 5,994,299 A | 11/1999 | Barriere et al. | |
| 6,177,253 B1 | 1/2001 | Erlanger et al. | |
| 6,207,398 B1 | 3/2001 | Wang | |
| 6,255,100 B1 | 7/2001 | Ko et al. | |
| 6,270,957 B1 | 8/2001 | Rich et al. | |
| 6,316,405 B1 | 11/2001 | Rich et al. | |
| 6,444,643 B1 | 9/2002 | Steiner et al. | |
| 6,521,595 B1 | 2/2003 | Kim et al. | |
| 6,583,265 B1 | 6/2003 | Ellmerer-Muller et al. | |
| 6,605,593 B1 | 8/2003 | Naicker et al. | |
| 6,613,739 B1 | 9/2003 | Naicker et al. | |
| 6,762,164 B2 | 7/2004 | Kim et al. | |
| 6,784,156 B2 | 8/2004 | Or et al. | |
| 6,790,830 B2 | 9/2004 | Kim et al. | |
| 6,790,935 B1 | 9/2004 | Mutter et al. | |
| 6,809,077 B2 | 10/2004 | Or et al. | |
| 6,927,208 B1 | 8/2005 | Wenger et al. | |
| 6,979,671 B2 | 12/2005 | Or et al. | |
| 6,987,090 B2 | 1/2006 | Kim et al. | |
| 6,995,139 B2 | 2/2006 | Wenger et al. | |
| 6,998,385 B2 | 2/2006 | Naicker et al. | |
| 7,012,064 B2 | 3/2006 | Or et al. | |
| 7,012,065 B2 | 3/2006 | Or et al. | |
| 7,060,672 B2 | 6/2006 | Naicker et al. | |
| 7,141,648 B2 | 11/2006 | Naicker et al. | |
| 7,226,905 B2 | 6/2007 | Viskov | |
| 7,226,906 B2 | 6/2007 | Hunt et al. | |
| 7,332,472 B2 | 2/2008 | Naicker et al. | |
| 7,358,229 B2 | 4/2008 | Naicker et al. | |
| 7,361,636 B2 | 4/2008 | Molino et al. | |
| 7,378,391 B2 | 5/2008 | Molino et al. | |
| 7,429,562 B2 | 9/2008 | Naicker et al. | |
| 7,468,419 B2 | 12/2008 | Wu et al. | |
| 7,696,166 B2 | 4/2010 | Molino | |
| 9,200,038 B2* | 12/2015 | Hegmans | A61K 38/13 |
| 2002/0132763 A1 | 9/2002 | Naicker et al. | |
| 2002/0165133 A1 | 11/2002 | Kim et al. | |
| 2003/0087813 A1 | 5/2003 | Or et al. | |
| 2003/0109425 A1 | 6/2003 | Or et al. | |
| 2003/0109426 A1 | 6/2003 | Or et al. | |
| 2003/0212249 A1 | 11/2003 | Naicker et al. | |
| 2003/0220234 A1 | 11/2003 | Naicker et al. | |
| 2004/0006088 A1 | 1/2004 | Hoover et al. | |
| 2004/0063626 A1 | 4/2004 | Kim et al. | |
| 2004/0071650 A1 | 4/2004 | Kim et al. | |
| 2004/0110666 A1 | 6/2004 | Or et al. | |
| 2004/0161399 A1 | 8/2004 | Kim et al. | |
| 2004/0220091 A1 | 11/2004 | Adam et al. | |
| 2004/0235716 A1 | 11/2004 | Molino et al. | |
| 2004/0266669 A1 | 12/2004 | Wu et al. | |
| 2006/0015374 A1 | 1/2006 | Ochs et al. | |
| 2006/0035821 A1 | 2/2006 | Hunt et al. | |
| 2006/0052290 A1 | 3/2006 | Naicker et al. | |
| 2006/0069015 A1 | 3/2006 | Molino et al. | |
| 2006/0074015 A1* | 4/2006 | Molino | C07K 7/645 514/20.5 |
| 2006/0135414 A1 | 6/2006 | Naicker et al. | |
| 2006/0223743 A1 | 10/2006 | Abel et al. | |
| 2007/0087963 A1 | 4/2007 | Naicker et al. | |
| 2007/0213260 A1 | 9/2007 | Viskov | |
| 2007/0232530 A1 | 10/2007 | Molino | |
| 2007/0232531 A1 | 10/2007 | Molino | |
| 2007/0232532 A1 | 10/2007 | Molino | |
| 2008/0021197 A1 | 1/2008 | Molino et al. | |
| 2008/0153744 A1 | 6/2008 | Molino et al. | |
| 2008/0171699 A1 | 7/2008 | Scribner et al. | |
| 2008/0171850 A1 | 7/2008 | Naicker et al. | |
| 2008/0214447 A1 | 9/2008 | Kobayashi et al. | |
| 2008/0249002 A1 | 10/2008 | Molino et al. | |
| 2013/0190223 A1 | 7/2013 | Hegmans et al. | |
| 2015/0065433 A1* | 3/2015 | Frydrych | C07K 1/113 514/18.7 |

FOREIGN PATENT DOCUMENTS

| | | |
|---|---|---|
| EP | 484281 A2 | 5/1992 |
| JP | 1989-045396 | 2/1989 |
| JP | 1993-208996 | 8/1993 |
| JP | 1995-252296 | 10/1995 |
| JP | 1997-143198 | 6/1997 |
| JP | 2005-507911 A | 3/2005 |
| JP | 2005-343904 A | 12/2005 |
| JP | 2008-514701 A | 5/2008 |
| RU | 2521358 | 8/2012 |
| WO | 97/11092 A1 | 3/1997 |
| WO | WO 99/18120 | 4/1999 |
| WO | 99/32512 A1 | 7/1999 |
| WO | 01/35914 A1 | 5/2001 |
| WO | 03030834 A2 | 4/2003 |
| WO | 03033010 A1 | 4/2003 |
| WO | WO 03/033527 | 4/2003 |
| WO | 2004/087798 A1 | 10/2004 |
| WO | 2005/021028 A1 | 3/2005 |
| WO | WO 2005/087798 | 9/2005 |
| WO | 2006/039163 A2 | 4/2006 |
| WO | WO 2006/039668 | 4/2006 |
| WO | 2007041631 A1 | 4/2007 |
| WO | 2007/112352 A2 | 10/2007 |
| WO | 2010088573 A1 | 8/2010 |
| WO | 2010138422 A1 | 12/2010 |

OTHER PUBLICATIONS

Berriman M. and Fairlamb AH., "Detailed characterization of a cyclophilin from the human malaria parasite Plasmodium falciparum", The Biochemical Journal, 1998, pp. 437-445, 9 pages.

Bua J., et al, "Anti-Trypanosoma cruzi effects of cyclosporin A derivatives: possible role of a P-glycoprotein and parasite cyclophilins", Parasitology, 2008, pp. 217-228, 12 pages.

Coelmont L., et al. "DEB025 (Alisporivir) inhibits hepatitis C virus replication by preventing a cyclophilin A induced cis-trans isomerisation in domain II of NS5A", PLoS One, 2010, p. 13687, 1 page.

Daelemans D., et al., "Debio-025 inhibits HIV-1 by interfering with an early event in the replication cycle", Antiviral Research, 2010, pp. 418-421, 4 pages.

Eberle, M.K. et al., "Modifications of the MeBMT side chain of cyclosporin A", Bioorganic & Medicinal Chemistry Letters, 5/15, pp. 1725-1728, 1995.

Final Office Action dated Feb. 1, 2014 from U.S. Appl. No. 13/056,616.

Final Office Action issued Mar. 16, 2015 in related U.S. Appl. No. 13/056,616.

Flisiak R., et al., "The cyclophilin inhibitor Debio 025 combined with PEG IFNalpha2a significantly reduces viral load in reatment-naïve hepatitis C patients", Hepatology, 2009, pp. 1460-1468, 8 pages.

Flisiak R., et al., "The cyclophilin inhibitor Debio-025 shows potent anti-hepatitis C effect in patients coinfected with hepatitis C and human immunodeficiency virus", Hepatology, 2008, pp. 817-826, 10 pages.

Gaither LA, et al., "Multiple cyclophilins involved in different cellular pathways mediate HCV replication", Virology, 2010, pp. 43-55, 13 pages.

Galat A and Bua J. "Molecular aspects of cyclophilins mediating therapeutic actions of their ligandsMolecular aspects of cyclophilins mediating therapeutic actions of their ligands", Cellular and Molecular Life Sciences, 2010, pp. 3467-3488, 22 pages.

(56) References Cited

OTHER PUBLICATIONS

Gomez, L., et al., "Inhibition of mitochondrial permeability transition improves functional recovery and reduces mortality following acute myocardial infarction in mice", American Journal of Physiology: Heart and Circulatory Physiology, 2007, pp. 1654-1661, 8 pages.
Halestrap AP and Pasdois P., "The role of the mitochondrial permeability transition pore in heart disease", Biochimica et Biophysica acta., 2009, pp. 1402-1415, 19 pages.
Hokari M., et al., "Pretreatment with the ciclosporin derivative NIM811 reduces delayed neuronal death in the hippocampus after transient forebrain ischaemia", The Journal of Pharmacy and Pharmacology, 2010, pp. 485-490, 6 pages.
Hopkins S., et al., "SCY-635, a novel nonimmunosuppressive analog of cyclosporine that exhibits potent inhibition of hepatitis C virus RNA relication in vitro", Antimicrobial Agents and Chemotherapy, 2010, pp. 660-672, 13 pages.
Kaul A., et al., "Essential role of cyclophilin A for hepatitis C virus replication and virus production and possible link to polyprotein cleavage kinetics", PLoS Pathogens, 2009, p. 1000546, 1 page.
Korde AS et al., "Protective effects of NIM811 in transient focal cerebral ischemia suggest involvement of the mitochondrial permeability transistion", Journal of Neurotrauma, 2007, pp. 895-908, 6 pages.
Kubota M., et al, "Therapeutic implications of down-regulation of cyclophilin D in bipolar disorder", International Journal of Neuropsycholpharmacology, 2010, pp. 1355-1368, 14 pages.
Lazarova et al., J. Med. Chem., 45/5, pp. 674-676, 2003.
LoGuidice A., et al., "Pharmacologic targeting or genetic deletion of mitochondrial cyclophilin D protects from NSAID-induced small intestinal ulceration in mice", Toxicological Sciences: An official journal of the Society of Toxicologoly, 2010, pp. 276-285, 10 pages.
Ma S., et al., "NIM811, a cyclophilin inhibitor, exhibits potent in vitro activity against hepatitis C virus alone or in combination with alpha interferon", Antimicrobial Agents and Chemotherapy, 2006, pp. 2976-2982, 7 pages.
Mathy JE, et al., "Combinations of cyclophilin inhibitor NIM811 with hepatitis C virus NS3-4A Protease or NS5B polymerase inhibitors enhance antiviral and suppress the emergence of resistance", Antimicrobial Agents and Chemotherapy, 2008, pp. 3267-3275, 9 pages.
Matsumoto, S., et al. "Blockade of the mitochondrial permeability transition pore diminishes infarct size in the rat after transient middle cebrebral artery occlusion", Journal of Cerebral Blood Flow and Metabolism: Official Journal of the International Society of Cerebral Blood Flow and Matabolism, 1999, pp. 736-741, 6 pages.
Mbye LH, et al., "Comparative neuroprotective effects of cyclosporin A and NIM811, a nonimmunosuppressive cyclosporin A analog, following traumatic brain injury", Journal of Celebral Blood Flow Metabolism: Official Journal of International Society of Celebral Blood Flow and Metabolism, 2009, pp. 87-97, 11 pages.
Miillay DP, et al., "Genetic and pharmacologic inhibition of mitochondrial-dependent necrosis attenuates muscular dystrophy", Nature Medicine, 2008, pp. 442-447, 5 pages.
Morota S., et al., "Evaluation of putative inhibitors of mitochondrial permeability transition for brain disorders—specificity vs toxicity", Experimental Neurology, 2009, pp. 353-362, 10 pages.
Non-final office action dated Aug. 6, 2013 from U.S. Appl. No. 13/056,616.
Non-final office action dated Sep. 4, 2014 from U.S. Appl. No. 13/056,616.
Non-final office action dated Jul. 29, 2015 in related U.S. Appl. No. 13/056,616.
Notice of Allowance dated Jul. 23, 2015 in related U.S. Appl. No. 13/994,707.
Paeshuyse J., et al., "The non-immunosuppressive cyclosporin DEBIO-025 is a potent inhibitor of hepatitis C virus replicaiton in vitro", Hepatology, 2006, pp. 761-770, 10 pages.
Park and Meier, Tetrahedeon letters, 30/32, pp. 4215-4218, 1989.

Ptak RG., et al., "Inhibition of human immunodeficiency virus type 1 replication in human cells by DEBIO-025, a novel cyclophilin binding agent", Antimicrobial Agents and Chemotherapy, 2008, pp. 1302-1317, 16 pages.
Quesniaux V.F.J. et al., Cyclophilin binds to the region of cyclosporine involved in its immunosuppresive activity. Eur. J. Immunology 1987, vol. 17, pp. 1359-1365, ISSN: 1521-4141; 7 pages.
Ravikumar R. et al, "Post-treatmentwith the cyclosporin deritative, NIM811, reduced indices of cell death and increased the volume of spared tissue in the acute period following spinal cord contusion", Journal of Neurotrauma, 2007, pp. 1618-1630, 12 pages.
Rehman H., et al., "NIM811 (N-methyl-4-isoleucine cyclosporine), a mitochondrial permeability transition inhibitor, attenuates cholestatic liver injury but not fibrosis in mice", Journal of Pharmacology and Experimental Therapeutics, 2008, pp. 699-706, 8 pages.
Rosenwirth B., et al., "Inhibition of human immunodeficiency virus type 1 replication by SDZ NIM 811, a nonimmunosuppressive cyclosporine analog", Antimicrobial Agents and Chemotherapy, 1994, pp. 1763-1772, 10 pages.
Rossi et al., "Recruitment of adult thymic progenitors is regulated by P-selectin and its ligand PSGL-1", Nature Immunology, 2005, pp. 626-634.
Scribner et al., "Synthesis and biological evaluation of [D-Lysine]8 cyclosporin A analogs as potential anti-HCV agents", pp. 6542-6546, 2010.
Sigal N.H. et al., Is cyclophilin involved in the immunosuppressive and nephrotoxic mechanism of action of cyclosporin A?, J.Exp. Med. 1991, vol. 173, pp. 619-628, ISSN: 1540-9538; 10 pages.
Smulik et al., Synthesis of cyclosporin A-derived affinity reagents by olefin metathesis, Organic Letters 2002 4(12):2051.
Theruvath, TP., et al., "Minocycline and N-methyl-4-isoleucine cyclosporin (NIM811) mitigate storage/reperfusion injury after rat liver transplantation through suppression of the mitochondrial permeability transition", Hepatology, 2008, pp. 236-246, 10 pages.
Tiepolo, T., et al., "The cyclophilin inhibitor Debio 025 normalizes mitochondrial function, muscle apoptosis and ultrastructural defects in Col6a1−/− myopathis mice", British Journal of Pharmacology, 2009, pp. 1045-1052, 8 pages.
Wissing ER, et al., "Debio-025 is more effective than prednisone in reducing muscular pathology in mdx mice", Neuromuscular Disorders, 2010, pp. 753-760, 8 pages.
Allain F. et al. "Interaction with glycosaminoglycans is required for cyclophilin B to trigger integrin-mediated adhesion of peripheral blood T lymphocytes to extracellular matrix", *Proc. Natl. Acad. Sci. USA* 2002, 99: 2714-2719.
Anderson SK et al. "A cyclophilin-related protein involved in the function of natural killer cells", *Proc. Natl. Acad. Sci. USA* 1993, 90:542-546.
Andreeva L. et al. "Cyclophilins and their possible role in the stress response", *Int. J. Exp Pathol.* 1999, 80:305-315.
Bartz S. et al. "Inhibition of human immunodeficiency virus replication by nonimmunosuppressive analogs of Cyclosporin A", *Proc. Natl. Acad. Sci. USA* 1995, 92: 5381-5385.
Billich A. et al. "Mode of action of SDZ NIM 811, a noninanunosuppressive Cyclosporin A analog with activity against human immunodeficiency virus (HIV) type 1: Interference with HIV protein-cyclophilin A interactions", *J. Virol.* 1995, 69: 2451-2461.
Billich et al. "Presence of Cyclophilin A in Synovial Fluids of Patients with Rheumatoid Arthritis", *J. Exp. Med.* 1997, 185(5):975-80.
Bourquin JP et al. "A serine/arginine-rich nuclear matrix cyclophilin interacts with the C-terminal domain of RNA polymerase II", *Nucleic Acids Res.* 1997, 25:2055-61.
Braaten D. et al. "Cyclophilin A is required for an early step in the life cycle of human immunodeficiency virus type 1 before the initiation of reverse transcription", *J. Virol.* 1996 70: 3551-3560.
Bukovsky A. et al. "Transfer of the HIV-1 cyclophilin-binding site to simian immunodeficiency virus from Macaca mulatta can confer both cyclosporine sensitivity and cyclosporine dependence", *Proc. Natl. Acad. Sci. USA* 1997, 94: 10943-10948.

(56) References Cited

OTHER PUBLICATIONS

Campa et al. "Protein Expression Profiling Identifies Macrophage Migration Inhibitory Factor and Cyclophilin A as Potential Molecular Targets in Non-Small Cell Lung Cancer", Cancer Res. 2003, 63(7):1652-6.
Caroni P et al. "New member of the cyclophilin family associated with thaw the secretory pathway", J. Biol. Chem. 1991, 266:10739-42.
Colgan J et al. "Cyclophilin A-Deficient Mice Are Resistant to Immunosuppression by Cyclosporine", J. Immunol. 2005, 174: 6030-6038.
Connern CP, Halestrap AP "Recruitment of mitochondrial cyclophilin to the mitochondrial inner membrane under conditions o.f oxidative stress that enhance the opening of a calcium-5 sensitive non-specific channel", Biochem. J. 1994, 302:321-4.
Craxi A. et al. "Clinical trial results of peginterferons in combination with ribavirin", Semen Liver Dis 2003; 23(Suppl 1):35-46.
Doman J. et al, "Structures of immunophilins and their ligand complexes", Curr. Top. Med. Chem. 2003, 3:1392-1409.
Du H. et a. "Cyclophilin D deficiency attenuates mitochondrial and neuronal perturbation and ameliorates learning and memory in Alzheimer's disease", Nature Medicine 2008, 14(10):1097-1105.
Fang F. et al. "The expression of Cyclophilin B is Associated with Malignant Progression and Regulation of Genes Implicated in the Pathogenesis of Breast Cancer", The American Journal of Pathology 2009, 174(1):297-308.
Fisher GA et al. "A phase 1 study of paclitaxel (taxol) (T) in combination with SDZ valspodar, a potent modulator of multidrug resistance (MDR)", Anticancer Drugs, 1994 5(Suppl 1): 43.
Flisiak R. et al. "Cyclophilin inhibitors in hepatitis C viral infection", Expert Opinion on Investigational Drugs 2007, 16(9):1345-1354.
Forte M. et al. "Cyclophilin D inactivation protects axons in experimental autoimmune encephalomyelitis, an animal model of multiple sclerosis", PNAS 2007, 104(18):7558-7563.
Friedman J .et al. "Two cytoplasmic candidates for immunophilin action are revealed by affinity for a new cyclophilin: one in the presence and one in the absence of CsA", Cell 1991, 66: 799-806.
Galat A. "Peptidylprolyl cis/trans isomerases (immunophilins): biological diversity- targets-functions", Curr. Top. Med. Chem. 2003, 3:1315-1347.
Galat A. et al. "Peptidylproline cis/trans isomerases", Prog. Biophys. Mol. Biol. 1995, 63:67-118.
Gamble T. et al. "Crystal structure of human cyclophilin A bound to the amino-terminal domain of HIV-1 capsid", Cell 1996, 87:1285-1294.
Gomez L. et al. "Inhibition of mitochondrial permeability transition improves functional recovery and reduces mortality following acute myocardial infarction in mice", Am. J. Physiol. Heart Circ. Physiol. 2007, 293:H1654-H1661.
Goto K., et al. "Evaluation of the anti-hepatitis C virus effects of cyclophilin inhibitors, CsA, and NIM8I1", Biochem. Biophys. Res. Comm. 2006, 343: 879-884.
Halestrap AP et al. "CsA binding to mitochondrial cyclophilin inhibits the permeability transition pore and protects hearts from ischaemia/reperfusion Injury", Mol. Cell Biochem. 1997, 174:167-72.
Hamilton GS et al. Immunophilins: beyond immunosuppression, J. Med. Chem. 1998, 41:5119-5143.
Handschumacher RE et al. "Cyclophilin: a specific cytosolic binding protein for CsA", Science 1984, 226: 544-7.
Hansson MJ et al. "The Nonimmunosuppressive Cyclosporine analogues NIM811 and UNIL025 Display Nanomolar Potencies on Permeability Transition in Brain- Derived Mitochondria", Journal of Bioenergetics and Biomembranes, 2004, 36(4): 407-413.
Harding MW et al. "Isolation and amino acid sequence of cyclophilin"J. Biol. Chem. 1986, 261:8547-55.
Harris R et al. "The Discovery of Novel Non-Immunosuppressie Cyclosporine Ethers and Thioethers With Potent HCV Activity",
Poster# 1915, *59th Annual Meeting of the American Association for the Study of Liver Diseases (AASLD)*, 2008.
Hatziioannou TD et at Cyclophilin interactions with incoming human immunodeficiency virus type 1 capsids with opposing effects on infectivity in human cells, J. Virol. 2005, 79:176-183.
Inoue K. et al. "Interferon combined with cyclosporine treatment as an effective countermeasure against hepatitis C virus recurrence in liver transplant patients with end-stage hepatitis C virus related disease", Transplant Proc. 2005, 37:1233-1234.
jin Z. et al. "Cyclophilin A is a secreted growth factor induced by oxidative stress", Circ. Res. 30 2000, 87:789-796.
Kamalpreet A et al. "Extracellular cyclophilins contribute to the regulation of inflammatory responses", J. Immunol. 2005, 175: 517-522.
Keep M. et al. "Intrathecal cyclosporine prolongs survival of late-stage ALS mice", Brain Research 2001, 894:327-331.
Kieffer LJ et al. "Cyclophilin-40, a protein with homology, to the P59 component of the steroid receptor complex. Cloning of the eDNA and further characterization", J. Biol.Chem. 1993, 268:12303-12310.
Kristal BS et al. "The Mitochondrial Permeability Transition as a Target for Neuroprotection", Journal of Bioenergetics and Biomembranes 2004, 36(4); 309-312.
Leventhal L. et al. "CsA protects striatal neurons in vitro and in vivo from 3-nitropropionic acid toxicity", Journal of Comparative Neurology 2000, 425(4):471-478.
Li et al. "Cyclophilin A Is Overexpressed in Human Pancreatic Cancer Cells and Stimulates Cell Proliferation through CD147", Cancer 2006, 106(10):2284-94.
Liu J. et al. "Calcineurin Is a Common Target of Cyclophilin-Cyclospo A and FKBP-FK506 Complexes", Cell 1991, 66: 807-815.
Lubart J. et al. "Human immunodeficiency virus type I Gag protein binds to cyclophilins A and B", Cell 1993, 73:1067-1078.
Manns M. et al. "The way forward in HCV treatment-finding the right path", Nature Reviews Drug Discovery 2007, 6:991-1000.
Matsuura K. et al. "GsA attenuates degeneration of dopaminergic neurons induced by 6-hydroxydoparnine in the mouse brain", Brain Research 1996, 733(1):101-104.
Mercer D. et al. "Hepatitis C virus replication in mice with chimeric human livers", Nat. Med. 2001, 7:927-933.
Merlini L. et al. "GsA corrects mitochondrial dysfunction and muscle apoptosis in patients with collagen VI myojatliies", PNAS 2008, 105(13): 5225-5229.
Mi H. et al. "A nuclear RNA-binding cyclophilln in human T cells", FEBS Lett. 1996, 398:201-205.
Mikol V. et al. "X-ray structure of tnonmeric cyclophilin A-cycloporin a crystal complex at 2.1 A resolution", J. Mol. Biol. 1993, 234:1119-1130.
Millay DP et al. "Genetic and pharmacologic inhibition of mitochondrial dependent necrosis attenuates muscular dystrophy", Nature Medicine 2008, 14(4): 442-447.
Mlynar E. et al. "The non-immunosuppressive GsA analogue SDZ NIM 811 inhibits cyclophilin A incorporation into virions and virus replication in human immunodeficiency virus type 1-infected primary and growth-arrested T cells", J. Gen. Virol. 1997, 78: 825-835.
Molino B. "Strategic Research Institute: 3rd annual viral hepatitis in drug discovery and development world summit 2007", AMRI Technical Reports; 12(1).
Piot C. et al. "Effect of Cyclosporine on Reperfusion Injury in Acute Myocardial Infarction", New England Journal of Medicine 2008, 395(5):474-481.
Ptak R et al. "Inhibition of Human Immunodeficiency Virus Type 1 Replication in Human Cells by Debio-025, a Novel Cyclophilin Binding Agent", Antimicrobial Agents and Chemotherapy 2008, 52(4), 1302-1317.
Rasola A. et al. "The mitochondrial permeability transition pore and its involvement in cell death and in disease pathogenesis", Apoptosis 2007, 12:815-833.
Rinfret A et al. "The N-terminal cydophilin-homologous domain of a 150-kilodalton tumor recognition molecule exhibits both peptidylprolyl cis-transisomerase and chaperone activities", Biochemistry, 1994, 33:1668-1673.

(56) References Cited

OTHER PUBLICATIONS

Rosenwirth BA et al. "Cyclophilin A as a novel target in anti-HIV-1 chemotherapy" *Int. Antivir. News* 1995, 3:62-63.
Rosenwirth B. et al "Inhibition of human immunodeficiency virus type 1 replication by SDZ NIM 811, a nonimmunosuppressive Cyclosporine Analogue", *Antimicrob Agents Chemother* 1994, 38:1763-1772.
Sherry B.et al. "Identification of cyclophilin as a proinflammatory secretory product of lipopolysaccharideactivated macrophages", *Proc. Natl. Acad. Sci. USA* 1992, 89: 3511-3515.
Steinkasserer A. et al. "Mode of action of SDZ NIM 811, a nonimmunosuppressive CsA analog with activity against human immunodeficiency virus type I (HIV-1): interference with early and late events in HIV-1 replication", *J. Virol.* 1995, 69: 814-824.
Thali M. et al. "Functional association of cyclophilin A with HIV-1 virions", *Nature* 1994, 372: 363-365.
Wainberg M. et al. "The effect of CsA on infection of susceptible cells by human immunodeficiency virus type 1", *Blood* 1998, 72:1904-1910.
Waldmeier PC et al. "Cyclophilin D as a drug target", *Curr. Med. Chem.* 2003. 10:1485-1506.
Watashi K et al, "Gyclophilin B is a Functional Regulator of Hepatitis C Virus RNA Polymerase", *Molecular Cell* 2005, 19:111-122.
Watashi K. et al. "CsA suppresses replication of hepatitis C virus genome in cultured hepatocytes", *Hepatology* 2003; 38:1282-1288.
Xu Q. et al. "Leukocyte chemotactic activity of cyclophilin", *J. Biol. Chem.* 1992; 267: 11968-11971.
Yang H. et al. "Cyclophilin A is upregulated in small cell lung cancer and activates ERK1/2 signal", *Biochemical and Biophysical Research Communications* 2007, 361: 763-767.
Yao Q. et al. "Roles of Cyclophilins in Cancers and Other Organs Systems", *World J. Surg.* 2005, 29: 276-280.
Yurchenko V. et al. "Active-site residues of cyclophilin A are crucial for its signaling activity via CD147", *J. Biol. Chem.* 2002; 277:22959-22965.
Zheng J. et al. "Prolyl Isomerase Cyclophilin A Regulation of Janus-Activated Kinase 2 and the Progression of Human Breast Cancer", *Cancer Research* 2008, 68(19): 7769-7778.

* cited by examiner

Figure 1A

Table 5

| 1-Mod Name | Modification: 1-Mod Structure | 1-Mod Structure | | 1 + 3-O-MeAla | |
|---|---|---|---|---|---|
| | | Cyp A inhibition Fold-potency vs CsA | Immunosuppression % vs CsA | Cyp A inhibition Fold-potency vs CsA | Immunosuppression % vs CsA |
| 404-58 | [structure with COOH] | 0.16 | <1 | 1.3 | <1 |
| 420-171 | [structure with COOH] | 2.3 | <1 | 8.7 | <1 |
| 420-19 | [structure with COOH] | 3.7 | <1 | 9.5 | 3.4 |
| 416-08 | [structure with COOH] | 3.7 | <1 | 14.3 | 3 |
| 404-96 | [structure] | 2.2 | 6.5 | 15 | 7.6 |

| | | | | | |
|---|---|---|---|---|---|
| 404-154 | structure with NMe₂ | 0.98 | 2 | 8.3 (saturated) | 9.2 (saturated) |
| 420-30-1 | structure with NH/acetyl | 3.3 | <1 | 11.7 | <1 |
| 420-103 | structure with (CH₂)₂COOEt, CsA | 0.19 | 10 | 1.9 (saturated) | 7.7 (saturated) |
| 404-173 | structure with ketone | 1.14 | 2.5 | 3.9 | 4 |
| 404-76 | structure with CH₂F | 0.65 | 12.5 | 2.8 | 9.7 |
| 404-194 | structure with nitrile | 0.61 | 2 | 4.4 | 1.4 |

Figure 1B

| 1-Mod Name | Modification | | 1-Mod Structure | | 1 + 3-D-EtSar | |
|---|---|---|---|---|---|---|
| | 1-Mod Structure | Cyp A Inhibition Fold-potency vs CsA | Immunosuppression % vs CsA | Cyp A Inhibition Fold-potency vs CsA | Immunosuppression % vs CsA |
| 404-58 |  | 0.16 | <1 | 0.56 | <1 |
| 420-19 |  | 3.7 | <1 | 4.2 | 2.3 |
| 404-154 |  | 0.98 | 2 | 10.6 (saturated) | 4.1 (saturated) |
| 420-30-1 |  | 3.3 | <1 | 8.9 | 1.1 |
| 404-194 |  | 0.61 | 2 | 2.1 | 4.9 |

CYCLOSPORINE ANALOGUE MOLECULES MODIFIED AT AMINO ACID 1 AND 3

FIELD OF THE INVENTION

The present invention relates to novel analogs of molecules belonging to the cyclosporine family, including analogs of Cyclosporine A (CsA) and including analogs that have reduced or no immunosuppressive activity and bind cyclophilin (CyP).

BACKGROUND OF THE INVENTION

Cyclosporines are members of a class of cyclic polypeptides having potent immunosuppressant activity. At least some of these compounds, such as Cyclosporine A (CsA), are produced by the species *Tolypocladium inflatum* as secondary metabolites. CsA is a potent immunosuppressive agent that has been demonstrated to suppress humoral immunity and cell-mediated immune reactions, such as allograft rejection, delayed hypersensitivity, experimental allergic encephalomyelitis, Freund's adjuvant arthritis and graft versus host disease. It is used for the prophylaxis of organ rejection in organ transplants; for the treatment of rheumatoid arthritis; and for the treatment of psoriasis.

Although a number of compounds in the cyclosporine family are known, CsA is perhaps the most widely used medically. The immunosuppressive effects of CsA are related to the inhibition of T-cell mediated activation events. Immunosuppression is accomplished by the binding of cyclosporine to a ubiquitous intracellular protein called cyclophilin (CyP). This complex, in turn, inhibits the calcium and calmodulin-dependent serine-threonine phosphatase activity of the enzyme calcineurin. Inhibition of calcineurin prevents the activation of transcription factors, such as $NFAT_{p/c}$ and NF-κB, which are necessary for the induction of cytokine genes (IL-2, IFN-γ, IL-4, and GM-CSF) during T-cell activation.

Since the original discovery of cyclosporine, a wide variety of naturally occurring cyclosporines have been isolated and identified. Additionally, many cyclosporines that do not occur naturally have been prepared by partial or total synthetic means, and by the application of modified cell culture techniques. Thus, the class comprising cyclosporines is substantial and includes, for example, the naturally occurring cyclosporines A through Z; various non-naturally occurring cyclosporine derivatives; artificial or synthetic cyclosporines including the dihydro- and iso-cyclosporines; derivatized cyclosporines (for example, either the 3'-O-atom of the MeBmt residue may be acylated, or a further substituent may be introduced at the sarcosyl residue at the 3-position); cyclosporines in which the MeBmt residue is present in isomeric form (e.g., in which the configuration across positions 6' and 7' of the MeBmt residue is cis rather than trans); and cyclosporines wherein variant amino acids are incorporated at specific positions within the peptide sequence.

Cyclosporine analogues containing modified amino acids in the 1-position are disclosed in WO 99/18120 and WO 03/033527, which are incorporated herein by reference in their entirety. These applications describe a cyclosporine derivative known as "$ISA_{TX}247$" or "ISA247" or "ISA." This analog is structurally identical to CsA, except for modification at the amino acid-1 residue. Applicants have previously discovered that certain mixtures of cis and trans isomers of ISA247, including mixtures that are predominantly comprised of trans ISA247, exhibited a combination of enhanced immunosuppressive potency and reduced toxicity over the naturally occurring and presently known cyclosporines.

Cyclosporine has three well established cellular targets; calcineurin, the CyP isoforms (which includes but is not limited to CyP-A, CyP-B and CyP-D), and P-glycoprotein (PgP). The binding of cyclosporine to calcineurin results in significant immunosuppression and is responsible for its traditional association with transplantation and autoimmune indications.

The Cyclophilin Family

CyPs (Enzyme Commission (EC) number 5.1.2.8) belong to a group of proteins that have peptidyl-prolyl cis-trans isomerase activity; such proteins are collectively known as immunophilins and also include the FK-506-binding proteins and the parvulins. CyPs are found in all cells of all organisms studied, in both prokaryotes and eukaryotes and are structurally conserved throughout evolution, There are 7 major CyPs in humans, namely CyP-A, CyP-B, CyP-C, CyP-D, CyP-E, CyP-40, and CyP-NK (first identified from human natural killer cells), and a total of 16 unique proteins (Galat A. Peptidylprolyl cis/trans isomerases (immunophilins): biological diversity-targets-functions. *Curr Top Med Chem* 2003, 3:1315-1347; Waldmeier P C et al. Cyclophilin D as a drug target. *Curr Med Chem* 2003, 10:1485-1506).

The first member of the CyPs to be identified in mammals was CyP-A. CyP-A is an 18-kDa cytosolic protein and is the most abundant protein for CsA binding. It is estimated that CyP-A makes up 0.6% of the total cytosolic protein (Mikol V et al. X-ray structure of monmeric cyclophilin A-cycloporin A crystal complex at 2.1 A resolution. *J. Mol. Biol.* 1993, 234:1119-1130; Galat A, Metcalfe S M. Peptidylproline cis/trans isomerases. Prog. Biophys. *Mol. Biol.* 1995, 63:67-118).

Cellular Location of Cyclophilins

CyPs can be found in most cellular compartments of most tissues and encode unique functions. In mammals, CyP-A and CyP-40 are cytosolic whereas CyP-B and CyP-C have amino-terminal signal sequences that target them to the endoplasmic reticulum protein secretory pathway (reviewed in Galat, 2003; Dornan J et al. Structures of immunophilins and their ligand complexes. *Curr Top Med Chem* 2003, 3:1392-1409). CyP-D has a signal sequence that directs it to the mitochondria (Andreeva L et al. Cyclophilins and their possible role in the stress response. *Int J Exp Pathol* 1999, 80:305-315; Hamilton G S et al. Immunophilins: beyond immunosuppression. *J Med Chem* 1998, 41:5119-5143); CyP-E has an amino-terminal RNA-binding domain and is localized in the nucleus (Mi H et al. A nuclear RNA-binding cyclophilin in human T cells. *FEBS Lett* 1996, 398:201-205) and CyP-40 has TPRs and is located in the cytosol (Kieffer L J et al. Cyclophilin-40, a protein with homology to the P59 component of the steroid receptor complex. Cloning of the cDNA and further characterization. *J Biol Chem* 1993, 268:12303-12310). Human CyP-NK is the largest CyP, with a large, hydrophilic and positively charged carboxyl terminus, and is located in the cytosol (Anderson S K et al. A cyclophilin-related protein involved in the function of natural killer cells. *Proc Natl Acad Sci USA* 1993, 90:542-546; Rinfret A et al. The N-terminal cyclophilin-homologous domain of a 150-kilodalton tumor recognition molecule exhibits both peptidylprolyl cis-trans isomerase and chaperone activities. *Biochemistry* 1994, 33:1668-1673)

Function and Activity of the Cyclophilins

CyPs are multifunctional proteins that are involved in many cellular processes. Because CyPs were highly conserved throughout evolution, this suggests an essential role for CyPs. Initially, it was found that CyPs have the specific enzymatic property of catalyzing cis-trans isomerization of peptidyl-prolyl bonds (Galat, 1995; Fisher G A et al. A phase I study of paclitaxel (taxol) (T) in combination with SDZ valspodar, a potent modulator of multidrug resistance (MDR), *Anticancer Drugs.* 1994; 5(Suppl 1): 43). Thus, CyPs are called peptidyl-prolyl-cis-trans isomerase (PPIase), which can act as an acceleration factor in the proper folding of newly synthesized proteins, PPIases are also involved in repairing damaged proteins due to environmental stresses including thermal stress, ultraviolet irradiation, changes in the pH of the cell environment, and treatment with oxidants. This function is known as molecular chaperoning activity. (Yao Q et al. Roles of Cyclophilins in Cancers and Other Organs Systems. *World J. Surg.* 2005, 29: 276-280)

In addition, the PPIase activity of CyPs has recently been shown to be involved in diverse cellular processes, including intracellular protein trafficking (Andreeva, 1999; Caroni P et al. New member of the cyclophilin family associated with the secretory pathway. *J Biol Chem* 1991, 266:10739-42), mitochondrial function (Halestrap A P et al. CsA binding to mitochondrial cyclophilin inhibits the permeability transition pore and protects hearts from ischaemia/reperfusion injury. *Mol Cell Biochem* 1997, 174:167-72; Connern C P, Halestrap A P. Recruitment of mitochondrial cyclophilin to the mitochondrial inner membrane under conditions of oxidative stress that enhance the opening of a calcium-sensitive non-specific channel. *Biochem J* 1994, 302:321-4), pre-mRNA processing (Bourquin J P et al. A serine/arginine rich nuclear matrix cyclophilin interacts with the C terminal domain of RNA polymerase II. *Nucleic Acids Res* 1997, 25:2055-61), and maintenance of multiprotein complex stability (Andreeva, 1999).

Cyclosporine binds with nanomolar affinity to CyP-A via contacts within the hydrophobic pocket (Colgan J et al. Cyclophilin A-Deficient Mice Are Resistant to Immunosuppression by Cyclosporine. *The Journal of Immunology* 2005, 174: 6030-6038, Mikol, 1993) and inhibits PPIase activity. However, this effect is thought to be irrelevant for the immunosuppression. Rather, the complex between CsA and CyP-A creates a composite surface that binds to and prevents calcineurin from regulating cytokine gene transcription (Friedman J et al. Two cytoplasmic candidates for immunophilin action are revealed by affinity for a new cyclophilin: one in the presence and one in the absence of CsA. *Cell* 1991, 66: 799-806; Liu J et al. Calcineurin is a common target of cyclophilin-CsA and FKBP-FK506 complexes. *Cell* 1991, 66: 807-815).

Homology of the Cyclophilins

CyP-A, the prototypical member of the family, is a highly conserved protein in mammalian cells (Handschumacher R E et al. Cyclophilin: a specific cytosolic binding protein for CsA. *Science* 1984, 226: 544-7). Sequence homology analysis of human CyP-A shows that it is highly homologous to human CyP-B, CyP-C, and CyP-D (Harding M W, Handschumacher R E, Speicher D W. Isolation and amino acid sequence of cyclophilin. *J Biol Chem* 1986, 261:8547-55). The cyclosporine binding pocket of all CyPs is formed by a highly conserved region of approximately 109 amino acids. Of the known CyPs, CyP-D has the highest homology to CyP-A. In fact, in this region the sequence identity is 100% between CyP-A and CyP-D (Waldmeier 2003; Kristal B S et al. The Mitochondrial Permeability Transition as a Target for Neuroprotection. *Journal of Bioenergetics and Biomembranes* 2004, 36(4); 309-312). Therefore, CyP-A affinity is a very good predictor of CyP-D affinity, and visa versa (Hansson M J et al. The Nonimmunosuppressive Cyclosporine analogues NIM811 and UNIL025 Display Nanomolar Potencies on Permeability Transition in Brain-Derived Mitochondria. *Journal of Bioenergetics and Biomembranes,* 2004, 36(4): 407-413). This relationship has been repeatedly demonstrated empirically with Cyclosporine analogues (Hansson, 2004; Ptak Rg et al. Inhibition of Human Immunodeficiency Virus Type 1 Replication in Human Cells by Debio-025, a Novel Cyclophilin Binding Agent. *Antimicrobial Agents and Chemotherapy* 2008: 1302-1317; Millay D P et al. Genetic and pharmacologic inhibition of mitochondrial dependent necrosis attenuates muscular dystrophy. *Nature Medicine* 2008, 14(4): 442-447; Harris R et al. The Discovery of Novel Non-Immunosuppressive Cyclosporine Ethers and Thioethers With Potent HCV Activity. Poster #1915, 59*th Annual Meeting of the American Association for the Study of Liver Diseases (AASLD),* 2008). The sequence homology across the CyPs suggests that all CyPs are potential targets for Cyclosporine analogues. Because of the multitude of cellular processes in which the CyPs are involved, this further suggests that CsA analogues that retain significant binding to CyP can be useful in the treatment of many disease indications.

Cyclophilin Mediated Diseases

Human Immunodeficiency Virus (HIV):

HIV is a lentivirus of the retrovirus family and serves as an example of the involvement of CyP in the process of infection and replication of certain viruses. CyP-A was established more than a decade ago to be a valid target in anti-HIV chemotherapy (Rosenwirth B A et al. Cyclophilin A as a novel target in anti-HIV-1 chemotherapy. *Int. Antivir. News* 1995, 3:62-63). CyP-A fulfills an essential function early in the HIV-1 replication cycle. It was found to bind specifically to the HIV-1 Gag polyprotein (Luban J K L et al. Human immunodeficiency virus type 1 Gag protein binds to cyclophilins A and B. *Cell* 1993, 73: 1067-1078). A defined amino acid sequence around G89 and P90 of capsid protein p24 (CA) was identified as the binding site for CyP-A (Bukovsky A A A et al. Transfer of the HIV-1 cyclophilin-binding site to simian immunodeficiency virus from *Macaca mulatta* can confer both cyclosporine sensitivity and cyclosporine dependence. *Proc. Natl. Acad. Sci. USA* 1997, 94: 10943-10948; Gamble T R F et al. Crystal structure of human cyclophilin A bound to the amino-terminal domain of HIV-1 capsid. *Cell* 1996, 87: 1285-1294). The affinity of CyP-A for CA promotes the incorporation of CyP-A into the virion particles during assembly (Thali M A et al. Functional association of cyclophilin A with HIV-1 virions. *Nature* 1994, 372: 363-365). Experimental evidence indicates that the CyP-A-CA interaction is essential for HIV-1 replication; inhibition of this interaction impairs HIV-1 replication in human cells (Hatziioannou T D et al. Cyclophilin interactions with incoming human immunodeficiency virus type 1 capsids with opposing effects on infectivity in human cells. *J. Virol.* 2005, 79: 176-183; Steinkasserer A R et al. Mode of action of SDZ NIM 811, a nonimmunosuppressive CsA analog with activity against human immunodeficiency virus type 1 (HIV-1): interference with early and late events in HIV-1 replication. *J. Virol* 1995, 69: 814-824). The step in the viral replication cycle where CyP-A is involved was demonstrated to be an event after penetration of the virus particle and before integration of the double-stranded viral DNA into the cellular genome (Braaten D E K et al. Cyclophilin A is required for an early step in the life cycle of human immunodeficiency virus type 1 before the initiation of reverse transcription. *J. Virol* 1996 70: 3551-3560;

Mlynar E D et al. The non-immunosuppressive CsA analogue SDZ NIM 811 inhibits cyclophilin A incorporation into virions and virus replication in human immunodeficiency virus type 1-infected primary and growth-arrested T cells. *J. Gen. Virol* 1996, 78: 825-835; Steinkasserer, 1995). The anti-HIV-1 activity of CsA was first reported in 1988 (Wainberg M A et al. The effect of CsA on infection of susceptible cells by human immunodeficiency virus type 1. *Blood* 1998, 72: 1904-1910). Evaluation of CsA and many derivatives for inhibition of HIV-1 replication revealed that nonimmunosuppressive CsA analogs had anti-HIV-1 activities equal to or even superior to those of immunosuppressive analogs (Bartz S R E et al. Inhibition of human immunodeficiency virus replication by nonimmunosuppressive analogs of CsA. *Proc. Natl. Acad. Sci. USA* 1995, 92: 5381-5385; Billich A F et al. Mode of action of SDZ NIM 811, a nonimmunosuppressive CsA analog with activity against human immunodeficiency virus (HIV) type 1: Interference with HIV protein-cyclophilin A interactions. *J. Virol* 1995, 69: 2451-2461; Ptak, 2008).

Inflammation

Inflammation in disease involves the influx of leukocytes (white blood cells) to the area of infection. The leukocytes are drawn to the area by chemokines, a family of chemoattracting agents. In vitro studies have shown that extracellular CyP-A is a potent chemoattractant for human leukocytes and T cells (Kamalpreet A et al. Extracellular cyclophilins contribute to the regulation of Inflammatory responses *Journal of Immunology* 2005; 175: 517-522; Yurchenko V G et al. Active-site residues of cyclophilin A are crucial for its signaling activity via CD147. *J. Biol. Chem.* 2002; 277: 22959-22965; Xu Q M C et al. Leukocyte chemotactic activity of cyclophilin. *J. Biol. Chem.* 1992; 267: 11968-11971; Allain F C et al. Interaction with glycosaminoglycans is required for cyclophilin B to trigger integrin-mediated adhesion of peripheral blood T lymphocytes to extracellular matrix. *Proc. Natl. Acad. Sci. USA* 2002; 99: 2714-2719). Furthermore, CyP-A can induce a rapid inflammatory response, characterized by leukocyte influx, when injected in vivo (Sherry B N et al. Identification of cyclophilin as a proinflammatory secretory product of lipopolysaccharide-activated macrophages. *Proc. Nat. Acad. Sci. USA* 1992; 89:3511-3515). CyP-A is ubiquitously distributed intracellularly, however, during the course of inflammatory responses, CyP-A is released into extracellular tissue spaces by both live and dying cells (Sherry, 1992). Indeed, elevated levels of CyP-A have been reported in several different inflammatory diseases, including sepsis, rheumatoid arthritis, and vascular smooth muscle cell disease (Jin Z G et al. Cyclophilin A is a secreted growth factor induced by oxidative stress. *Circ. Res.* 2000; 87: 789-796; Teger, 1997; Billich, 1997). In the case of rheumatoid arthritis, a direct correlation between levels of CyP-A and the number of neutrophils in the synovial fluid of rheumatoid arthritis patients was reported (Billich, 1997).

Cancer

CyP-A has recently been shown to be over-expressed in many cancer tissues and cell lines, including but not limited to small and non-small cell lung, bladder, hepatocellular, pancreatic and breast cancer (Li, 2006; Yang H et al. Cyclophilin A is upregulated in small cell lung cancer and activates ERK½ signal. *Biochemical and Biophysical Research Communications* 2007; 361: 763-767; Campa, 2003). In cases where exogenous CyP-A was supplied this was shown to stimulate the cancer cell growth (Li, 2006; Yang, 2007) while CsA arrested the growth (Campa, 2003). Most recently it has been demonstrated the CyP (A and B) is intricately involved in the biochemical pathway allowing growth of human breast cancer cells and that CyP knockdown experiments decreased the cancer cell growth, proliferation and motility (Fang F et al. The expression of Cyclophilin B is Associated with Malignant Progression and Regulation of Genes Implicated in the Pathogenesis of Breast Cancer. *The American Journal of Pathology* 2009; 174(1): 297-308; Zheng J et al. Prolyl Isomerase Cyclophilin A Regulation of Janus-Activated Kinase 2 and the Progression of Human Breast Cancer. *Cancer Research* 2008; 68 (19): 7769-7778). Most interestingly, CsA treatment of mice xenografted with breast cancer cells induced tumor necrosis and completely inhibited metastasis (Zheng. 2008). The researchers conclude that "Cyclophilin B action may significantly contribute to the pathogenesis of human breast cancer" and that "cyclophilin inhibition may be a novel therapeutic strategy in the treatment of human breast cancer" (Fang, 2009; Zheng, 2008).

Hepatitis C

Hepatitis C Virus (HCV) is the most prevalent liver disease in the world and is considered by the World Health Organization as an epidemic. Because HCV can infect a patient for decades before being discovered, it is often called the "silent" epidemic. Studies suggest that over 200 million people worldwide are infected with HCV, an overall incidence of around 3.3% of the world's population. In the US alone, nearly 4 million people are or have been infected with HCV and of these; 2.7 million have an ongoing chronic infection. All HCV infected individuals are at risk of developing serious life-threatening liver diseases. Current standard therapy for chronic hepatitis C consists of the combination of pegylated interferon in combination with ribavirin, both generalized anti-viral agents (Craxi A et al. Clinical trial results of peginterferons in combination with ribavirin. *Semin Liver Dis* 2003; 23(Suppl 1): 35-46). Failure rate for the treatment is approximately 50% (Molino B F. Strategic Research Institute: $3^{rd}$ annual viral hepatitis in drug discovery and development world summit 2007. *AMRI Technical Reports;* 12(1)).

It has recently been demonstrated that CyP-B is critical for the efficient replication of the HCV genome (Watashi K et al. Cyclophilin B Is a Functional Regulator of Hepatitis C Virus RNA Polymerase. Molecular Cell 2005, 19: 111-122). Viruses depend on host-derived factors such as CyP-B for their efficient genome replication. CyP-B interacts with the HCV RNA polymerase NS5B to directly stimulate its RNA binding activity. Both the RNA interference (RNAi)-mediated reduction of endogenous CyP-B expression and the induced loss of NS5B binding to CyP-B decreases the levels of HCV replication. Thus, CyP-B functions as a stimulatory regulator of NS5B in HCV replication machinery. This regulation mechanism for viral replication identifies CyP-B as a target for antiviral therapeutic strategies.

Unlike other HCV treatments, CyP inhibition does not directly target the HCV virus. It is therefore thought that resistance to CyP binding drugs will occur more slowly than current HCV treatment drugs (Manns M P, et al. The way forward in HCV treatment-finding the right path. *Nature Reviews Drug Discovery* 2007; 6: 991-1000). In addition, by interfering at the level of host-viral interaction, CyP inhibition may open the way for a novel approach to anti-HCV treatment that could be complementary, not only to interferon-based treatment, but also to future treatments that directly target HCV replication enzymes such as protease and polymerase inhibitors (Flisiak R, Dumont J M, Crabbé R. Cyclophilin inhibitors in hepatitis C viral infection. *Expert Opinion on Investigational Drugs* 2007, 16(9): 1345-

1354). Development of new anti-HCV drugs effecting HCV viral replication has been significantly impeded by the lack of a suitable laboratory HCV model. This obstacle has only recently been overcome by the development of several suitable cell culture models (Subgenomic HCV Replicon Systems) and a mouse model containing human liver cells (Goto K, et al. Evaluation of the anti-hepatitis C virus effects of cyclophilin inhibitors, CsA, and NIM811. *Biochem Biophys Res Comm* 2006; 343: 879-884; Mercer D F, et al. Hepatitis C virus replication in mice with chimeric human livers. *Nat Med* 2001; 7: 927-933). Cyclosporine has recently demonstrated anti-HCV activity in screening models and in small clinical trials (Watashi K, et al. CsA suppresses replication of hepatitis C virus genome in cultured hepatocytes. *Hepatology* 2003; 38:1282-1288; Inoue K, Yoshiba M. Interferon combined with cyclosporine treatment as an effective countermeasure against hepatitis C virus recurrence in liver transplant patients with end-stage hepatitis C virus related disease. *Transplant Proc* 2005; 37:1233-1234).

Muscular Degenerative Disorders

CyP-D is an integral part of the mitochondrial permeability transition pore (MTP) in all cells. The function of the MTP pore is to provide calcium homeostasis within the cell. Under normal conditions the opening and closing of the MTP pore is reversible. Under pathological conditions that Involve an excessive calcium influx into the cell, this overloads the mitochondria and induces an irreversible opening of the MPT pore, leading to cell death or apoptosis. CsA has been reported to correct mitochondrial dysfunction and muscle apoptosis in patients with Ullrich congenital muscular dystrophy and Bethlam myopathy [(Merlini L et al. CsA corrects mitochondrial dysfunction and muscle apoptosis in patients with collagen VI myopathies. *PNAS* 2008; 105(13): 5225-5229]. CsA has been demonstrated in vitro to dose dependently inhibit MTP opening in isolated cardiac mitochondria, thereby preventing apoptosis and allowing the cell precious time for repair (Gomez L et al. Inhibition of mitochondrial permeability transition improves functional recovery and reduces mortality following acute myocardial infarction in mice *Am J Physiol Heart Circ Physiol* 2007, 293: H1654-H1661). A clinical study in 58 patients who presented with acute myocardial infarction demonstrated that administration of CsA at the time of reperfusion was associated with a smaller infarct than that seen with placebo (Piot C et al. Effect of Cyclosporine on Reperfusion Injury in Acute Myocardial Infarction. *New England Journal of Medicine* 2008; 395(5): 474-481)).

Chronic Neurodegenerative Diseases

CsA can act as a neuroprotective agent in cases of acute cerebral ischemia and damage as a result of head trauma (Keep M, et al. Intrathecal cyclosporine prolongs survival of late-stage ALS mice. *Brain Research* 2001; 894: 327-331). Animals treated with CsA showed a dramatic 80% survival rate relative to only a 10% survival rate in the absence of treatment. It was later established that this was largely the result of the binding of CsA to mitochondrial CyP-D. It has been subsequently established that the utility of CsA extends to chronic neurodegeneration, as was subsequently demonstrated in a rat model of Lou Gerhig's Disease (ALS) (U.S. Pat. No. 5,972,924), where CsA treatment more than doubled the remaining life-span. It has also recently been shown that CyP-D inactivation in CyP-D knockout mice protects axons in experimental autoimmune encephalomyelitis, an animal model of multiple sclerosis (Forte M et al. Cyclophilin D inactivation protects axons in experimental autoimmune encephalomyelitis, an animal model of multiple sclerosis. *PNAS* 2007; 104(18): 7558-7563). In an Alzhelmer's disease mouse model CyP-D deficiency substantially improves learning, memory and synaptic function (Du H et al. Cyclophilin D deficiency attenuates mitochondrial and neuronal perturbation and ameliorates learning and memory in Alzheimer's disease *Nature Medicine* 2008, 14(10): 1097-1105). In addition, CsA has been shown to be effective in a rat model of Huntington's disease (Leventhal L et al. CsA protects striatal neurons in vitro and in vivo from 3-nitropropionic acid toxicity. *Journal of Comparative Neurology* 2000, 425(4): 471-478), and partially effective in a mouse model of Parkinson's disease (Matsuura K et al. CsA attenuates degeneration of dopaminergic neurons induced by 6-hydroxydopamine in the mouse brain. *Brain Research* 1996, 733(1): 101-104). Thus, mitochondrial-dependent necrosis represents a prominent disease mechanism suggesting that inhibition of CyP-D could provide a new pharmacologic treatment strategy for these diseases (Du, 2008).

Cellular, Tissue and Organ Injury Due to a Loss of Cellular Calcium Ion ($Ca^{2+}$) Homeostasis $Ca^{2+}$ is involved in a number of physiological processes at a cellular level, including healthy mitochondrial function. Under certain pathological conditions, such as myocardial infarct, stroke, acute hepatotoxicity, cholestasis, and storage/reperfusion injury of transplant organs, mitochondria lose the ability to regulate calcium levels, and excessive calcium accumulation in the mitochondrial matrix results in the opening of large pores in the inner mitochondrial membrane. (Rasola A. et al. The mitochondrial permeability transition pore and its involvement in cell death and in disease pathogenesis. *Apoptosis* 2007, 12: 815-833.) Nonselective conductance of ions and molecules up to 1.5 kilodaltons through the pore, a process called mitochondrial permeability transition, leads to swelling of mitochondria and other events which culminate in cell death, including the induction of apoptosis. One of the components of the MTP is CyP-D. CyP-D is an immunophilin molecule whose isomerase activity regulates opening of the MPTP, and inhibition of the isomerase activity by CsA or CsA analogs inhibits creation of the MPTP, and thus prevents cell death.

Non-Immunosuppressive Cyclosporine Analogue Cyclophilin Inhibitors

Despite the advantageous effects of CsA in the above mentioned indications, the concomitant effects of immunosuppression limit the utility of CsA as a CyP inhibitor in clinical practice. At present, there are only a few CsA analogs that have been proven to have little or reduced immunosuppressive activity (i.e., <10% of the immunosuppressive potency of CsA) and still retain their ability to bind CyP (i.e., >10% CyP binding capacity as compared to CsA).

NIM 811 (Melle$^4$-Cyclosporine)

NIM 811 is a fermentation product of the fungus *Tolypocladium niveum*, which is modified at amino acid 4 and displays no immunosuppressive activity (due to lack of calcineurin binding), yet retains binding affinity for CyP-A (Rosenwirth B A et al. Inhibition of human immunodeficiency virus type 1 replication by SDZ NIM 811, a nonimmunosuppressive Cyclosporine Analogue. *Antimicrob Agents Chemother* 1994, 38: 1763-1772).

DEBIO 025 (MeAla$^3$EtVal$^4$-Cyclosporin)

DEBIO 025 is a dual chemical modification of CsA at amino acids 3 and 4. DEBIO 025 also displays no immunosuppressive activity yet retains binding affinity for CyP-A PPIase activity (Kristal, 2004).

SCY-635 (DimethylaminoethylthioSar³-hydroxyLeu⁴-Cyclosporin)

SCY-635 is a dual chemical modification of CsA at amino acids 3 and 4. SCY-635 also displays no immunosuppressive activity yet retains binding affinity for CyP-A PPIase activity (PCT Publication No. WO2006/039668).

Generally, these compounds have modification on the face of CsA that is responsible for binding calcineurin, and generally require the modification of amino acids 3 and 4. The modification of amino acids 3 and 4 is laborious and complex, as this approach typically involves opening up the cyclosporine ring, replacing and/or modifying those amino acids and then closing up the ring to produce the modified cyclosporine.

In contrast, modification of the side chain of amino acid 1 does not require opening of the cyclosporine ring. However, amino acid 1 is associated with CyP binding (as opposed to calcineurin binding) and has been modified to increase the immunosuppressive efficacy of CsA. For example U.S. Pat. No. 6,605,593, discloses a single modification of amino acid 1 that results in a CsA analog with increased immunosuppressive potency.

Therefore, it would be desirable to have a cyclosporine analogue molecule (a "CAM") that is readily synthesized and is efficacious in the treatment of CyP mediated diseases. It is also desirable to provide a CsA analogue that provides as least some of the functionality of native CsA, but which possesses improved or additional properties, effects or functions relative to native CsA.

SUMMARY OF THE INVENTION

According to one aspect, compounds of the present invention comprise cyclosporin-A analogs that are non-immunosuppressive according to the definition herein. According to another aspect, the compounds have affinity for cyclophilin, including cyclophilin-A. According to other aspects, compounds of the present invention comprise cyclosporin-A analogs that are at useful with respect to a cyclophilin-mediated disease or condition and developing therapies with respect to such diseases and conditions.

According to one aspect, the invention relates to a compound of Formula L:

Formula L

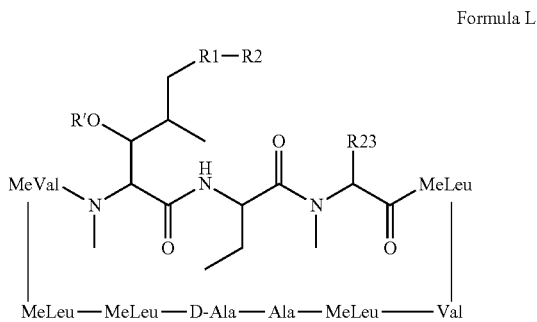

wherein
  a. R' is H or acetyl;
  b. R1 is a saturated or unsaturated straight chain or branched aliphatic carbon chain from 2 to 15 carbon atoms in length;
  c. R2 is selected from the group consisting of:
    i. H;
    ii. an unsubstituted, N-substituted, or N,N-disubstituted amide;
    iii. a N-substituted or unsubstituted acyl protected amine;
    iv. a carboxylic acid;
    v. a N-substituted or unsubstituted amine;
    vi. a nitrile;
    vii. an ester;
    viii. a ketone;
    ix. a hydroxy, dihydroxy, trihydroxy, or polyhydroxy alkyl; and
    x. a substituted or unsubstituted aryl;
    xi. a saturated or unsaturated, straight or branched aliphatic chain optionally containing a substituent selected from the group consisting of hydrogen, ketones, hydroxyls, nitriles, carboxylic acids, esters, 1,3-dioxolanes, halogens, and oxo;
    xii. an aromatic group containing a substituent selected from the group consisting of halides, esters and nitro; and
    xiii. a combination of the saturated or unsaturated, straight or branched aliphatic chain of (xi) and the aromatic group of (xii); and
  d. R23 is a saturated or unsaturated straight chain or branched optionally substituted aliphatic carbon chain.

In one aspect, the substituent R1-R2 is selected from the group consisting of:

i.

⟋⟍COOH;

ii.

⟋⟍⟋COOH;

iii.

⟋⟍⟋COOH;

iv.

⟋⟍(CH₂)₃COOH;

v.

⟋⟍(CH₂)₃COOH;

vi.

⟋⟍⟋⟍⟋COOH;

vii.

⟋⟍⟋⟍⟋COOH;

viii.

⟋⟍⟋⟍⟋COOH;

ix.

⟋⟍⟋⟍⟋C(O)OH;

x.

⟋⟍⟋⟍⟋COOH;

xi.

⟋⟍(CH₂)₉COOH;

xii.

⟋⟍(CH₂)₆COOH;

xiii.

⟋⟍(CH₂)₉COOH;

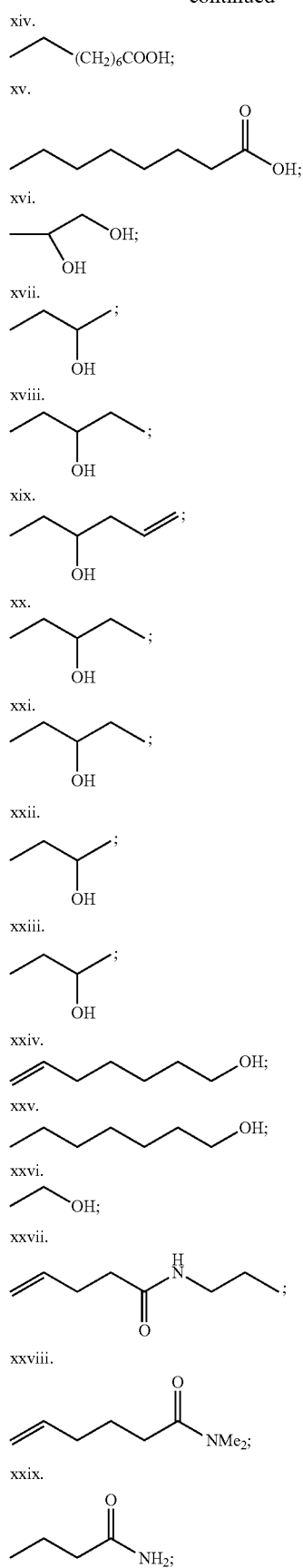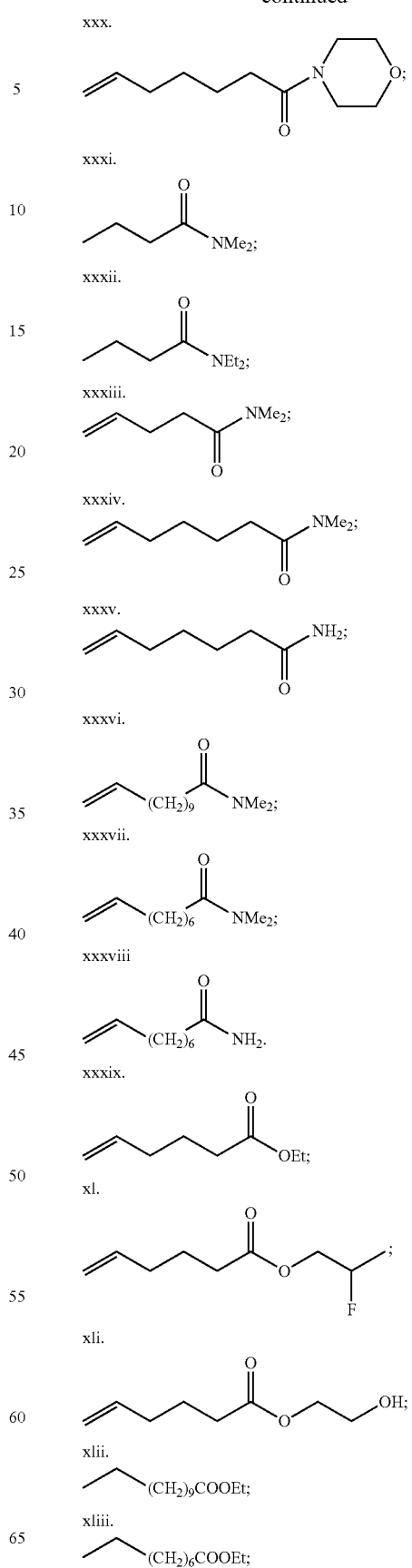

xliv. 3-vinyl-methyl benzoate;

xlv. pentan-3-one;

xlvi. butan-2-one;

xlvii. 1-butene;

xlviii. 1-pentene;

xlix. 1-CH=CH-(CH₂)₆CH₃;

l. 1-hexene;

li. CH=CH-(CH₂)₄CH₃;

lii. 3-methyl-1-butene;

liii. pent-4-en-1-amine (NH₂);

liv. oct-7-en-1-amine (NH₂);

lv. pent-4-enenitrile;

lvi. oct-7-enenitrile;

lvii. but-3-enenitrile;

lviii. N-pentyl acetamide;

lix. NHBOC pentenyl;

lx. NHBOC octenyl;

lxi. N-(oct-7-en-1-yl)acetamide;

lxii. N-pentyl butyramide;

lxiii. N-octyl acetamide;

lxiv. N-(pent-4-en-1-yl)butyramide;

lxv. N-(oct-7-en-1-yl)butyramide (with (CH₂)₅);

lxvi. N-butyl acetamide;

lxvii. NHBOC octyl;

lxviii. styrene;

lxix. ethylbenzene;

lxx. 4-fluorostyrene;

lxxi. 4-fluoroethylbenzene;

lxxii. 3-vinylbenzoic acid (COOH); and lxxiii. 3-vinyl methyl benzoate (COOMe).

In another aspect, R2 is selected from the group consisting of

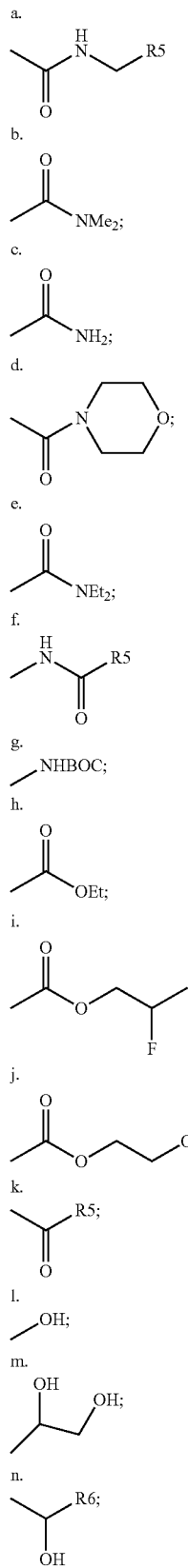

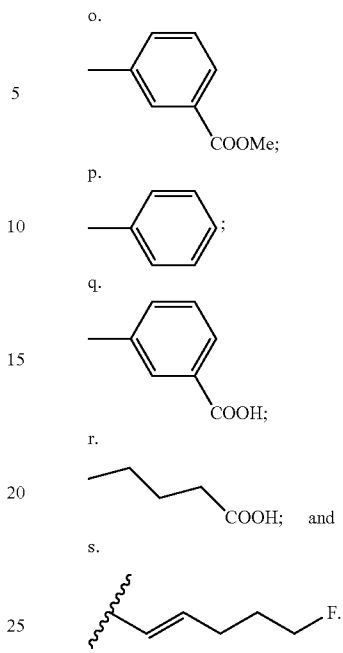

wherein
  i. R5 is a saturated or unsaturated straight chain or branched aliphatic carbon chain between 1 and 10 carbons in length; and
  ii. R6 is a monohydroxylated, dihydroxylated, trihydroxylated or polyhydroxylated saturated or unsaturated straight chain or branched aliphatic carbon chain between 1 and 10 carbons in length.

In one aspect, R1-R2 comprises a saturated or unsaturated, straight or branched aliphatic chain of between 2 and 5 carbons optionally substituted with a substituent selected from the group consisting of hydrogen, ketones, hydroxyls, nitriles, halogens, oxo, carboxylic acids, esters and 1,3-dioxolanes;

In one aspect, R23 is selected from the group consisting of:
  i. —$CH_3$
  ii. —$CH_2CH_3$
  iii. —$CH_2CHCH_2$
  iv. —$CH_2CH_2CH_2I$
  v. —$(CH_2)_3CH_2I$
  vi. —$(CH_2)_3N^+(CH_3)_3$
  vii. —$CH_2CCH$
  viii. —$CH_2CO_2(t\text{-}Bu)$
  ix. —$CH_2Ph$
  x. —$CH_2OH$
  xi. —$CH(OH)CH_3$
  xii. —$CH(OH)(t\text{-}Bu)$
  xiii. —$CH(OH)Ph$
  xiv. —COOH
  xv. —$SCH_3$
  xvi. —S(p-Tol)

In one aspect, R23 comprises an optionally substituted alkyl, including optionally substituted C1-C3 alkyl. Said alkyl may be substituted with amino and may comprise a C1-C3-Ala wherein said compound comprises the D-epimer. In said embodiment, R23 can be MeAla.

In one aspect, on the above formula L,

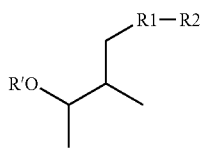

is selected from the group consisting of:

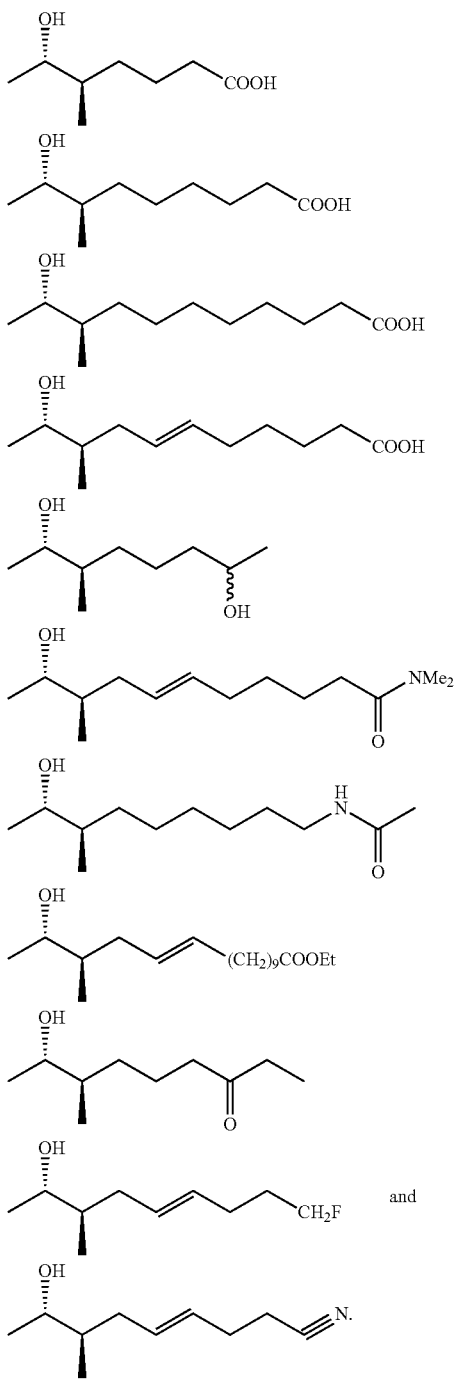

In one aspect, R23 is a straight or branched aliphatic carbon chain of 1 to 6, 1 to 5, 1 to 4, 1 to 3 or 2 carbons in length.

In one aspect, the invention relates to a method of treating or preventing a cyclophilin mediated disease in a mammal comprising administering the compound as described herein to the mammal under conditions to treat the cyclophilin mediated disease or injury, or use of said compound or composition to treat said disease or injury, or use of the compound to prepare a medicament for said use or treatment. Said disease or injury can be mediated by the over expression of cyclophilin or the disease is a congenital over expression of cyclophillin. Said cyclophilin mediated disease or injury can be selected from the group consisting of
 a. a viral infection;
 b. inflammatory disease;
 c. cancer;
 d. muscular disorder;
 e. neurological disorder; and
 f. injury associated with ischemia, reperfusion, loss of cellular calcium homeostasis, loss of ionic homeostasis, increase in free radical production, or toxins that induce mitochondrial dysfunction;
wherein the viral infection is optionally caused by a virus selected from the group consisting of Human Immunodeficiency virus, Hepatitis A, Hepatitis B, Hepatitis C, Hepatitis D, Hepatitis E, SARS-CoV, hCoV-NL63, hCoV-HKU-1, hCoV-OC43, hCOV-229E, coronavirus, feline infectious peritonitis virus, and transmissible gastroenteritis virus;
wherein the inflammatory disease is optionally selected from the group consisting of asthma, autoimmune disease, chronic inflammation, chronic prostatitis, glomerulonephritis, hypersensitivity disease, inflammatory bowel disease, sepsis, vascular smooth muscle cell disease, aneurysms, pelvic inflammatory disease, reperfusion injury, rheumatoid arthritis, transplant rejection, and vasculitis;
wherein the cancer is optionally selected from the group consisting of small and non-small cell lung, bladder, hepatocellular, pancreatic, breast cancer, glioblastoma, colorectal cancer, squamous cell carcinoma, melanoma, and prostate cancer;
wherein the muscular disorder is optionally selected from the group consisting of myocardial reperfusion injury, muscular dystrophy, collagen VI myopathies, Post-cardiac arrest syndrome (PCAS), heart failure, atherosclerosis, and abdominal aortic aneurysm;
wherein the neurological disorder is optionally selected from the group consisting of Alzheimer's disease, Parkinson's disease, Huntington's disease, multiple systems atrophy, multiple sclerosis, cerebral palsy, epilepsy, stroke, diabetic neuropathy, amyotrophic lateral sclerosis (Lou Gehrig's Disease), bipolar disorder, excitotoxic injury, hepatic encephalopathy, hypoglycemia, manganese toxicity, neuronal target deprivation, toxic fatty acids such as arachadonic acid, mechanical nerve injury, spinal cord injury, and cerebral injury; and
wherein the injury associated with loss of cellular calcium homeostasis is optionally selected from the group consisting of myocardial infarct, stroke, acute hepatotoxicity, cholestasis, and storage/reperfusion injury of transplant organs.

In one aspect, the invention relates to a process for the preparation of a compound of the above Formula L, comprising the steps of:

1) reacting cyclosporin-A (CsA) with a basic lithium alkylamide, in the presence of a suitable solvent, followed by reaction with a suitable electrophile to generate a compound of Formula 1:

Formula 1

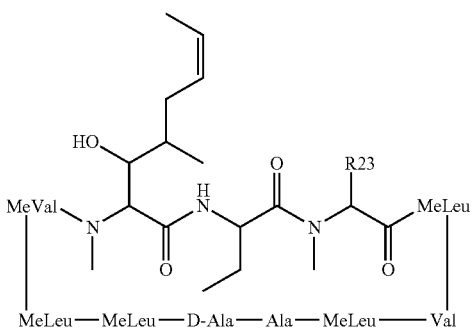

2) reacting the compound of Formula 1 with AC₂O in the presence of a suitable solvent to form a compound of Formula 2A:

Formula 2A

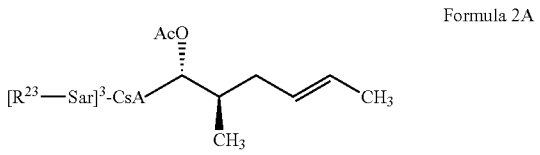

3) Reacting the compound of Formula 2A with an oxidant to form a compound of Formula 3A:

Formula 3A

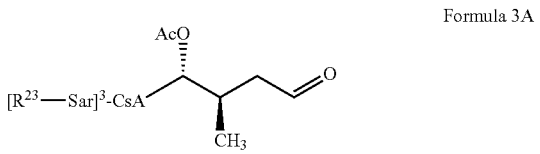

4) Reacting the compound of Formula 3A with an electrophile to form a compound of Formula 4A:

Formula 4A

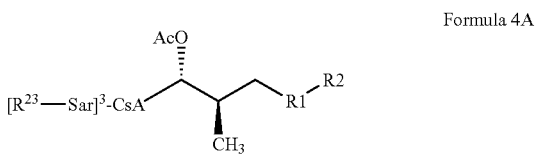

5) optionally deacylating the compound of Formula 4A.

In one aspect, the above preparation of Formula L comprises the addition of an excess of LiCl in said solvent to form predominantly the L-epimer of Formula L, or said preparation of Formula L Is carried out in the absence of LiCl to form predominantly the D-epimer of Formula L. Said basic lithium alkylamide can comprise lithium diisopropylamide.

In one aspect, said electrophile is selected from the group defined in the following table, to generate the corresponding R23 set out in said table:

| Electrophile | R23 |
|---|---|
| methyl iodide | —CH₃ |
| ethyl iodide | —CH₂CH₃ |
| allyl bromide | —CH₂CHCH₂ |
| 1,3-diiodopropane | —CH₂CH₂CH₂I |
| 1,4-diiodobutane | —(CH₂)₃CH₂I |
| trimethylammonium-3-iodopropane hexafluorophosphate | —(CH₂)₃N⁺(CH₃)₃ |
| propargyl bromide | —CH₂CCH |
| tert-butyl bromoacetate | —CH₂CO₂(t-Bu) |
| benzyl bromide | —CH₂Ph² |
| formaldehyde | —CH₂OH |
| acetaldehyde | —CH(OH)CH₃ |
| pivalaldehyde | —CH(OH)(t-Bu)³ |
| benzaldehyde | —CH(OH)Ph |
| carbon dioxide | —COOH |
| dimethyl disulfide | —SCH₃ |
| p-tolyl disulfide | —S(p-Tol)⁴ |

In one aspect, the invention relates to a method for the preparation of Formula L as defined herein comprising the steps of:
1) reacting a compound of Formula 1A with dimethylaminopridine in the presence of a suitable solvent, to form the compound of Formula 2:

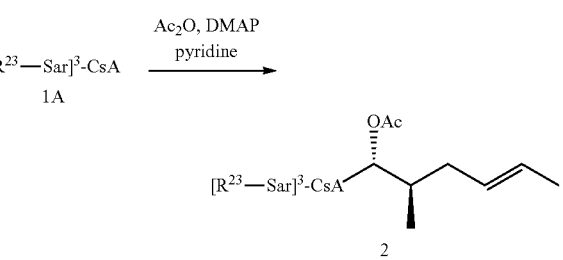

optionally followed by formation of the aldehyde of Formula 3:

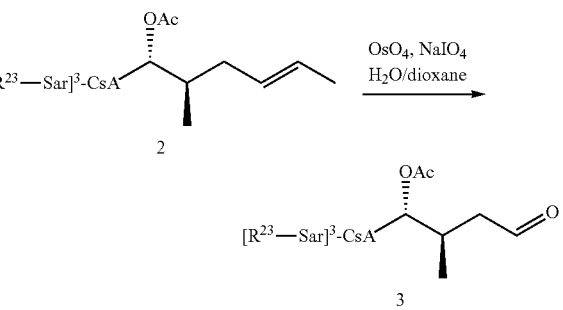

optionally followed by a Wittig reaction to generate compounds of Formula L, wherein R23 is selected from the group consisting of
i. —CH₃
ii. —CHCH₂CH
ii. —CH₂CHCH₂.
iv. —H₂CH₂CH₂I
v. —(CH₂)₃CH₂I;
vi. —(CH₂)₃N⁺(CH₃)₃;
vii. —CH₂CCH;
viii. —CH₂CO₂(t-Bu).
ix. —CH₂Ph
x. —CH₂OH;

xi. —CH(OH)CH$_3$;
xii. —CH(OH)(t-Bu)$^3$;
xiii. —CH(OH)Ph;
xiv. —COOH;
xv. —SCH$_3$; and
xvi. —S(p-Tol)

In one aspect, the invention relates to the preparation of Formula L as defined herein comprising the steps of: reacting a compound of Formula 5, with a basic lithium alkylamide, optionally comprising lithium diispropylamide, in presence of a suitable electrophile in an appropriate solvent to form the compound of Formula L, wherein R23 comprises optionally substituted C1-C3 alkyl.

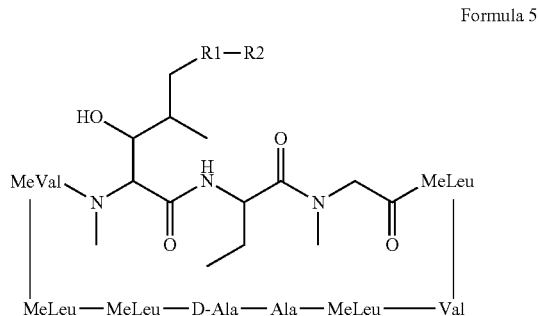

Formula 5

In general, for all chemical formulae disclosed in this document:

"Carboxylic acid" includes a group in which the carboxylic acid moiety Is connected to one of the following substituents:
 1. alkyl which may be substituted (for example, alkyl of 2 to 15 carbons);
 2. alkenyl which may be substituted (for example, alkenyl of 2 to 15 carbons); and
 3. alkynyl which may be substituted (for example, alkynyl of 2 to 15 carbons);

The substituents of the above-described may include halogen (for example, fluorine, chlorine, bromine, iodine, etc.), nitro, cyano, hydroxy, thiol which may be substituted (for example, thiol, C1-4 alkylthio, etc.), amino which may be substituted (for example, amino, mono-C1-4 alkylamino, di-C1-4 alkylamino, 5- to 6-membered cyclic amino such as tetrahydropyrrole, piperazine, piperidine, morpholine, thiomorpholine, pyrrole, imidazole, etc.), C1-4 alkoxy which may be halogenated (for example, methoxy, ethoxy, propoxy, butoxy, trifluoromethoxy, trifluoroethoxy, etc.), C1-4 alkoxy-C1-4 alkoxy which may be halogenated (for example, methoxymethoxy, methoxyethoxy, ethoxyethoxy, trifluoromethoxyethoxy, trifluoroethoxyethoxy, etc.), formyl, C2-4 alkanoyl (for example, acetyl, propionyl, etc.), C1-4 alkylsulfonyl (for example, methanesulfonyl, ethanesulfonyl, etc.), and the like, and the number of the substituents is preferably 1 to 3.

Further, the substituents of the above "amino which may be substituted" may bind each other to form a cyclic amino group (for example, a group which is formed by subtracting a hydrogen atom from the ring constituting nitrogen atom of a 5- to 6-membered ring such as tetrahydropyrrole, piperazine, piperidine, morpholine, thiomorpholine, pyrrole, imidazole, etc. so that a substituent can be attached to the nitrogen atom, or the like). The cyclic amino group may be substituted and examples of the substituent include halogen (for example, fluorine, chlorine, bromine, iodine, etc.), nitro, cyano, hydroxy, thiol which may be substituted (for example, thiol, C1-4 alkylthio, etc.), amino which may be substituted (for example, amino, mono-C.sub.1-4 alkylamino, di-C1-4 alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, C1-4 alkoxy-carbonyl, carbamoyl, mono-C1-4 alkyl-carbamoyl, di-C1-4 alkyl-carbamoyl, etc.), C1-4 alkoxy which may be halogenated (for example, methoxy, ethoxy, propoxy, butoxy, trifluoromethoxy, trifluoroethoxy, etc.), C1-4 alkoxy-C.sub.1-4 alkoxy which may halogenated (for example, methoxymethoxy, methoxyethoxy, ethoxyethoxy, trifluoromethoxyethoxy, trifluoroethoxyethoxy, etc.), formyl, C2-4 alkanoyl (for example, acetyl, propionyl, etc.), C1-4 alkylsulfonyl (for example, methanesulfonyl, ethanesulfonyl), and the like, and the number of the substituents is preferably 1 to 3.

"Amine" includes a group which may be unsubstituted or in which the amine moiety is N-substituted or N,N disubstituted having one or two substituents which may be independently selected from:
 1. alkyl which may be substituted (for example, alkyl of 2 to 15 carbons);
 2. alkenyl which may be substituted (for example, alkenyl of 2 to 15 carbons);
 3. alkynyl which may be substituted (for example, alkynyl of 2 to 15 carbons);
 4. formyl or acyl which may be substituted (for example, alkanoyl of 2 to 4 carbons (for example, acetyl, propionyl, butyryl, isobutyryl, etc.), alkylsulfonyl of 1 to 4 carbons (for example, methanesulfonyl, ethanesulfonyl, etc.) and the like);
 5. aryl which may be substituted (for example, phenyl, naphthyl, etc.); and the like;
and connected to a substituent independently selected from the substituents as defined for "carboxylic acid" above.

"Amide" includes a compound in which the carboxylic group of the amide moiety is connected to a substituent independently selected from the substituents as defined for "carboxylic acid" above, connected to the amino group of the amide moiety is an N-substituted or N,N disubstituted having one or two substituents, respectively, which may be independently selected from:
 1. alkyl which may be substituted (for example, alkyl of 2 to 15 carbons);
 2. alkenyl which may be substituted (for example, alkenyl of 2 to 15 carbons);
 3. alkynyl which may be substituted (for example, alkynyl of 2 to 15 carbons);
 4. formyl or acyl which may be substituted (for example, alkanoyl of 2 to 4 carbons (for example, acetyl, propionyl, butyryl, isobutyryl, etc.), alkylsulfonyl of 1 to 4 carbons (for example, methanesulfonyl, ethanesulfonyl, etc.) and the like);
 5. aryl which may be substituted (for example, phenyl, naphthyl, etc.); and the like "Aryl" may be exemplified by a monocyclic or fused polycyclic aromatic hydrocarbon group, and for example, a C6-14 aryl group such as phenyl, naphthyl, anthryl, phenanthryl or acenaphthylenyl, and the like are preferred, with phenyl being preferred. Said aryl may be substituted with one or more substituents, such as lower alkoxy (e.g., C1-6 alkoxy such as methoxy, ethoxy or propoxy, etc.), a halogen atom (e.g., fluorine, chlorine, bromine, iodine, etc.), lower alkyl (e.g., C1-6 alkyl such as methyl, ethyl or propyl, etc.), lower alkenyl (e.g., C2-6 alkenyl such as vinyl or allyl, etc.), lower alkynyl (e.g., C.2-6 alkynyl such as ethynyl or propargyl, etc.), amino which may be substituted, hydroxyl which may be substituted, cyano, amidino which may be substituted, carboxyl, lower alkoxycarbonyl (e.g., C1-6 alkoxycarbonyl such as methoxycarbonyl or ethoxycarbonyl, etc.), carbamoyl which may be substituted (e.g., carbamoyl which may be substituted with C1-6 alkyl or acyl (e.g., formyl, C2-6 alkanoyl, benzoyl, C1-6 alkoxycarbonyl which may be halogenated. C1-6 alkylsulfonyl which may be halogenated, benzenesulfonyl, etc.) which may be substituted with a 5- to 6-membered aromatic monocyclic heterocyclic group (e.g., pyridinyl, etc.), 1-azetidinylcarbonyl, 1-pyrrolidinylcarbonyl, piperidinocarbonyl, morpholinocarbonyl, thiomorpholinocarbonyl (the sulfur atom may be oxidized). 1-piperazinylcarbonyl, etc.), or the like. Any of these substituents may be independently substituted at 1 to 3 substitutable positions.

"Ketone" includes a compound in which the carbonyl group of the ketone moiety is connected to one or two substituents independently selected from the substituents as defined above for said "carboxylic acid".

"Ester" Includes either a carboxylic or an alcohol ester wherein of the ester group is composed of one or two substituents independently selected from the substituents as defined for "carboxylic acid" or "aryl".

"Alkyl" unless otherwise defined is preferably an alkyl of 1 to 15 carbon units in length.

"Aromatic group" may be exemplified by aryl as defined above, or a 5- to 6-membered aromatic monocyclic heterocyclic group such as furyl, thienyl, pyrrolyl, oxazolyl, isoxazolyl, thiazolyl, isothiazolyl, Imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; and a 8- to 16-membered (preferably, 10- to 12-membered) aromatic fused heterocyclic group "Non-immunosuppressive" refers to the ability of a compound to exhibit a substantially reduced level of suppression of the immune system as compared with CsA, as measured by the compounds ability to inhibit the proliferation of human lymphocytes in cell culture and preferably as measured by the method set out in Example 19 below.

"Analogue" means a structural analogue of CsA that differs from CsA in one or more functional groups. Preferably, such analogues preserve at least a substantial portion of the ability of CsA to bind CyP.

Preferred species of Formula I are those in which R' is H, R1 is a saturated or unsaturated alkyl between 2 and 15 carbons in length and R2 is selected from:
1. carboxylic acid comprising a carboxyl group;
2. N-substituted of N,N-disubstituted amide wherein the substituents are independently selected from an H, an alkyl of between 1 and 7 carbons in length, or said substituents form a heterocyclic ring of which the heterocyle is selected from O, N or S;
3. an ester of between 1 and 7 carbons in length;
4. an monohydroxylated, or dihydroxylated alkyl of between 1 and 7 carbons in length;
5. a N-substituted or unsubstituted acyl protected amine of between 1 and 7 carbons in length;
6. a nitrile;
7. a ketone wherein the carboxylic group of the ketone is connected to R1 and saturated or unsaturated alkyl chain of between 1 and 7 carbons in length;
8. phenyl, optionally substituted with one or more substituents independently selected from nitrogen dioxide, a fluorine, an amine, an ester or a carboxyl group.

The compounds of the present invention may exist in the form of optically active compounds. The present invention contemplates all enantiomers of optically active compounds within the scope of the above formulae, both individually and in mixtures of racemates. As well, the present invention includes prodrugs of the compounds defined herein.

According to another aspect, compounds of the present invention may be useful for treating or preventing or studying a CyP mediated disease in a mammal, preferably a human. Such disease is usually mediated by the over expression of CyP, such as a congenital over expression of CyP.

CyP mediated diseases which may be treated by compounds of the present invention include:
a. a viral infection;
b. inflammatory disease;
c. cancer;
d. muscular degenerative disorder;
e. neurodegenerative disorder; and
f. injury associated with loss of cellular calcium homeostasis.

Said viral infection may be caused by a virus selected from the group consisting of Human Immunodeficiency Virus, Hepatitis A, Hepatitis B, Hepatitis C, Hepatitis D, and Hepatitis E. Said inflammatory disease is selected from the group consisting of asthma, autoimmune disease, chronic inflammation, chronic prostatitis, glomerulonephritis, hypersensitivity disease, inflammatory bowel disease, sepsis, vascular smooth muscle cell disease, aneurysms, pelvic inflammatory disease, reperfusion injury, rheumatoid arthritis, transplant rejection, and vasculitis. Said cancer may be selected from the group consisting of small and non-small cell lung, bladder, hepatocellular, pancreatic and breast cancer. Said muscular degenerative disorder may selected from the group consisting of myocardial reperfusion injury, muscular dystrophy and collagen VI myopathies. Said neurodegenerative disorder may be selected from the group consisting of Alzheimer's disease, Parkinson's disease, Huntington's disease, Multiple Systems Atrophy, Multiple Sclerosis, cerebral palsy, stroke, diabetic neuropathy, amyotrophic lateral sclerosis (Lou Gehrig's Disease), spinal cord injury, and cerebral injury. Said injury associated with loss of cellular calcium homeostasis may be selected from the group consisting of myocardial infarct, stroke, acute hepatotoxicity, cholestasis, and storage/reperfusion injury of transplant organs.

BRIEF DESCRIPTION OF THE DRAWINGS

FIGS. 1A, 1B, and 1C depict Table 5 showing cyclophilin A inhibition and immunosuppression of CsA analogs modifies at position 1 and at positions 1 and 3.

DETAILED DESCRIPTION

Figure 1C:
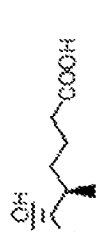
Figure 1C:
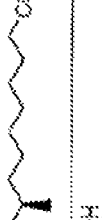
Figure 1C:
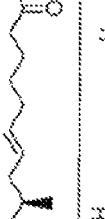
Figure 1C:
Figure 1C:

According to one aspect, a compound of this invention may be administered neat or with a pharmaceutical carrier to a warm-blooded animal in need thereof. The pharmaceutical carrier may be solid or liquid. The compound may be administered orally, topically, parenterally, by inhalation spray or rectally in dosage unit formulations containing conventional non-toxic pharmaceutically acceptable carriers, adjuvants and vehicles. The term parenteral, as used herein, includes subcutaneous injections, intravenous, intramuscular, intrasternal injection or infusion techniques.

The pharmaceutical compositions containing the inventive mixture may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to methods known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may include: (1) suspending agents such as sodium carboxymethylcellulose, methylcellulose, hydroxypropylmethylcellulose, sodium alginate, polyvinylpyrrolidone, gum tragacanth and gum acacia; or (2) dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitan monooleate, or a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose, aspartame or saccharin.

Oily suspension may be formulated by suspending the active ingredient in a vegetable oil, for example arachis oil, olive oil, sesame oil or coconut oil, a fish oil which contains omega 3 fatty acid, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in a mixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions containing the inventive mixture may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial ester 30 derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol, aspartame or sucrose. Such formulations may also contain a demulcent, a preservative, and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

The inventive compound may also be administered in the form of suppositories for rectal administration of the drug. Suitable compositions can be prepared by mixing the compound with a suitable non-irritating excipient which is solid at ordinary temperatures but liquid at the rectal temperature and will therefore melt in the rectum to release the drug. Such materials are cocoa butter and polyethylene glycols.

For topical use, suitable creams, ointments, jellies, solutions or suspensions, etc., which normally are used with cyclosporine may be employed.

In a particularly preferred embodiment, a liquid solution containing a surfactant, ethanol, a lipophilic and/or an amphiphilic solvent as non-active ingredients is used. Specifically, an oral multiple emulsion formula containing the isomeric analogue mixture and the following non-medicinal ingredients: d-alpha Tocopheryl polyethylene glycol 1000 succinate (vitamin E TPGS), medium chain triglyceride (MCT) oil, Tween 40, and ethanol is used. A soft gelatin capsule (comprising gelatin, glycerin, water, and sorbitol) containing the compound and the same non-medicinal ingredients as the oral solution may also preferably be used.

It will be understood, however, that the specific dose level for any particular patient will depend upon a variety of factors including the activity of the specific compound employed, the age, body weight, general health, sex, diet, time of administration, route of administration, rate of excretion, drug combination and the nature and severity of the particular disease or condition undergoing therapy.

Methodology

The reactions set out below, are general examples of the chemical reactions able to synthesize the desired compounds modified at amino acid 1 residue (AA1) and amino acid 3 residue (AA3) of CsA. Modifications to AA1 are depicted as:

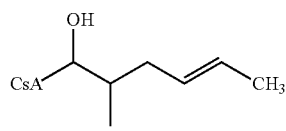

and modifications to AA3 are depicted as

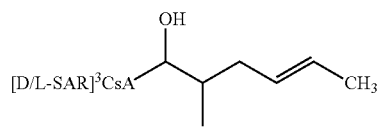

both modifications to AA1 and AA3 use reagents that have the requisite chemical properties, and it would be understood by a person skilled in the art that substitutions of certain reactants may be made.

The identity and purity of the prepared compounds were generally established by methodologies including mass spectrometry, HPLC and NMR spectroscopy. Mass spectra (ESI-MS) were measured on a Hewlett Packard 1100 MSD system. NMR spectra were measured on a Varian Mercury-Plus 400 MHz spectrometer in deuterated solvents (DMSO for phosphonium salts, benzene for all other compounds). Analytical and preparative reversed phase HPLC was carried out on an Agilent 1100 Series system.

Synthesis of Phosphonium Salt Compounds

Phosphonium salts are prepared through reaction of triphenylphosphine or any other suitable phosphines with alkyl halides (R—X; X=Cl, Br, or I). Suitable alkyl halides are any primary or any secondary aliphatic halide of any chain length or molecular weight. These alkyl halides may be branched or unbranched, saturated or unsaturated.

If the reaction is carried out in toluene (Reaction 1), the product precipitates directly from the reaction solution. Unreactive substrates, however, require a more polar solvent such as dimethylformamide (DMF) (Reaction 2) to shorten reaction times and to achieve satisfactory yields.

Reaction 1

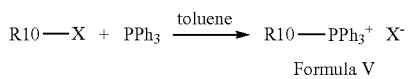

Formula V

Where X is a halide (including but not limited to Cl, Br, and I), and R10 is a saturated or unsaturated, straight or branched aliphatic chain, optionally containing a substituent selected from the group of ketones, hydroxyls, nitriles, carboxylic acids, esters and 1,3-dioxolanes; an aromatic group, optionally containing a substituent selected from the group of halides, esters and nitro; or a combination of the aforementioned saturated or unsaturated, straight or branched aliphatic chain and the aforementioned aromatic groups.

Example 1. Synthesis of 404-15

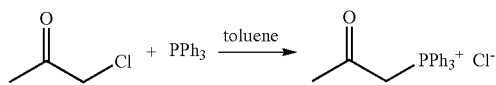

As an illustrative example, triphenylphosphine (13 mmol) is dissolved in 50 mL toluene and chloroacetone (10 mmol) is added to give a clear solution. The reaction is stirred under reflux over night. A colorless solid is filtered off, washed with toluene and hexane and dried in vacuum.

Using Reaction 1, the following compounds are further examples of the compounds that may be synthesized.

| Compound | Reactant (R10—X) | Conditions |
| --- | --- | --- |
| 404-08 | benzyl bromide | 4 hours at reflux |

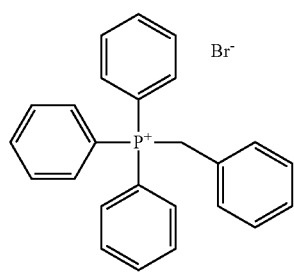 [SMILES: c1ccc(C[P+](c2ccccc2)(c2ccccc2)c2ccccc2)cc1 ; [Br-]]

-continued
| Compound | Reactant (R10—X) | Conditions |
|---|---|---|
| 404-09  | methyl iodide | RT over night |
| 404-12  | 4-nitrobenzyl bromide | 6 hours at reflux |
| 404-15  | chloroacetone | reflux over night |
| 404-64  | 4-fluorobenzyl bromide | reflux over night |
| 404-77  | methyl 3-bromomethylbensoate | 6 hours at reflux |

-continued

| Compound | Reactant (R10—X) | Conditions |
|---|---|---|
| 404-87 | 3-nitrobenzyl bromide | 6 hours at reflux |
| 404-161 | 1-bromo-2-butanone | RT over night |
| 404-170 | 4-bromobutyronitrile | reflux over night |

Alternatively, suitable phosphonium salts may be synthesized through Reaction 2 as illustrated below:

Reaction 2

$$R11-X + PPh_3 \xrightarrow{DMF} R11-PPh_3^+ \ X^-$$

Formula VI

Where X is a halide (including but not limited to Cl, Br, and I), and R10 is a saturated or unsaturated, straight or branched aliphatic chain, optionally containing a substituent selected from the group of ketones, hydroxyls, nitriles, carboxylic acids, esters and 1,3-dioxolanes; an aromatic group, optionally containing a substituent selected from the group of halides, esters and nitro; or a combination of the aforementioned saturated or unsaturated, straight or branched aliphatic chain and the aforementioned aromatic groups.

Example 2: Synthesis of 404-51

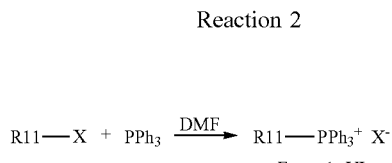

As an illustrative example, triphenylphosphine (11 mmol) is dissolved in 10 mL DMF and 4-bromobutyric acid (10 mmol) is added. The reaction is stirred for 7 hours at 110° C. and is then allowed to cool over night. Fifty mL toluene is added and a crystalline, colorless solid is collected by filtration. The product is washed with toluene and hexane and dried in vacuum over night.

If crystallization does not set in after treatment with toluene, the product is extracted with 20 mL MeOH/H$_2$O (1:1 mixture). The aqueous phase is washed with toluene and hexane and brought to dryness. The residue is stirred with 50 mL ethyl acetate (EtOAc) at reflux temperature for 20-30 min. If a crystalline solid is obtained, the product is collected by filtration, washed with EtOAc and hexane and dried. In case the product is obtained as an oil or gum, the EtOAc is decanted and the remaining product is dried in vacuum.

Using Reaction 2, the following compounds are further examples of the compounds that may be synthesized.

| Compound | Reactant (R11—X) | Conditions |
| --- | --- | --- |
| 404-14 | 1-bromobutane | 6.5 hours at 120° C. |
| 404-29 | 2-bromomethyl-1,3-dioxolane | 120° C. over night |
| 404-34 | 1-bromooctane | 110° C. over night |
| 404-51 | 5-bromovaleric acid | 8 hours at 120° C. |
| 404-78 | 6-bromohexanol | 110° C. over night |

-continued

| Compound | Reactant (R11—X) | Conditions |
|---|---|---|
| 404-116 | 4-bromobutyric acid | 7 hours at 110° C. |
| 416-01 | 1-bromohexane | 110° C. over night |
| 416-02 | 6-bromohexanoic acid | 110° C. over night |
| 419-132 | 7-bromoheptanenitrile | 110° C. over night |
| 419-134 | 6-chloro-2-hexanone | 110° C. over night |

-continued

| Compound | Reactant (R11—X) | Conditions |
|---|---|---|
| 419-136 [Ph3P+(CH2)8OH Br−] | 9-bromo-1-nonanol | 110° C. over night |
| 420-32 [Ph3P+–(CH2)6COOMe Br−] | methyl 7-bromohexanoate | 110° C. over night |
| 420-78 [Ph3P+(CH2)9COOH Br−] | 11-bromoundecanoic acid | 110° C. over night |
| 420-80 [Ph3P+–CH2CH2CN Br−] | 3-bromopropionitrile | 110° C. over night |
| 420-82 [Ph3P+(CH2)6COOH Br−] | 8-bromooctanoic acid | 110° C. over night |

| Compound | Reactant (R11—X) | Conditions |
|---|---|---|
| 420-90 | 6-bromohexanenitrile | 110° C. over night |
| 420-94 | 5-chloro-2-pentanone | 110° C. over night |

Wittig Reaction

The Wittig reaction is broadly applicable to a wide range of substrates and reactants. The side chain, which is introduced to the substrate in the reaction, can represent any number of branched and unbranched, saturated and unsaturated aliphatic compounds of variable length (R') and may contain a broad range of functional groups.

In the Wittig reaction, a base, such as potassium tert-butoxide (KOtBu) is used to generate an ylide from a phosphonium salt. The ylide reacts with the carbonyl group of the substrate, CsA-aldehyde, to form an alkene. Phosphonium salts containing a carboxylic acid side chain require at least two equivalents of base to generate the ylide.

Reaction 3: Synthesis of an Acetylated Cyclosporine Analogue Intermediate Using a Phosphonium Salt Compound Through a Wittig Reaction

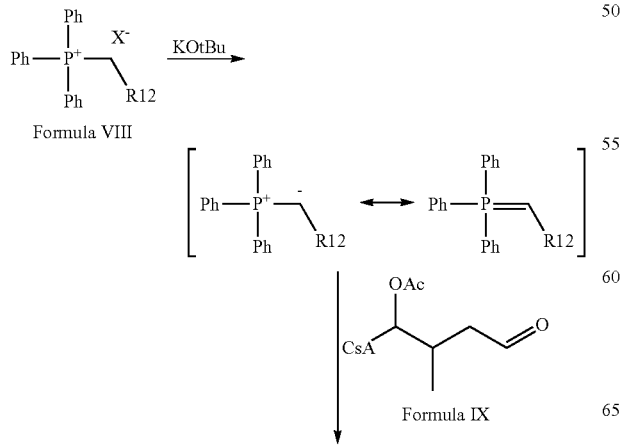

Where X is a halide (including but not limited to Cl, Br, and I), and R12 is a saturated or unsaturated, straight or branched aliphatic chain, optionally containing a substituent selected from the group of ketones, hydroxyls, nitriles, carboxylic acids, esters and 1,3-dioxolanes; an aromatic group, optionally containing a substituent selected from the group of halides, esters and nitro; or a combination of the aforementioned saturated or unsaturated, straight or branched aliphatic chain and the aforementioned aromatic groups.

Example 3: Synthesis of Compound 404-20 Using a Phosphonium Salt Compound Through a Wittig Reaction -continued

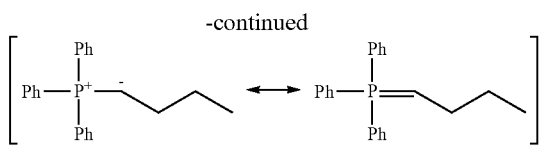

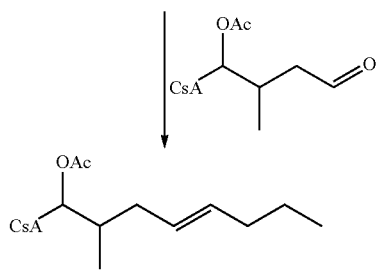

As an illustrative example, an oven dried 250 mL flask is charged under argon atmosphere with triphenylbutylphosphonium bromide (6.0 mmol) and 40 mL anhydrous tetrahydrofuran (THF). The suspension is cooled to 0° C. and potassium tert-butoxide (6.0 mmol) is added to obtain an orange color. The reaction is stirred at ambient temperature for 1-2 hours, followed by addition of CsA-aldehyde (2.0 mmol, dissolved in 20 mL anhydrous THF). Stirring is continued for 3 hours at room temperature. The reaction is quenched with 10 mL sat. $NH_4Cl$ and 20 mL ice-water. The layers are separated and the aqueous phase is extracted with EtOAc. The organic layers are combined, washed with brine and dried over $Na_2SO_4$. The solvent is removed and the crude product is purified over silica gel (hexane/acetone 3:1).

Using Reaction 3, the following compounds are further examples of the compounds that may be synthesized.

| Compound | Starting Material | MS (Na$^+$) | Remarks |
|---|---|---|---|
| 404-16 | 404-09 | 1252.9 | |
| 404-19 | 404-08 | 1328.9 | |
| 404-20 | 404-14 | 1294.9 | |

-continued

| Compound | Starting Material | MS (Na$^+$) | Remarks |
|---|---|---|---|
| 404-30 (CsA-CH(OAc)-CH(CH$_3$)-CH$_2$-CH=CH-C$_6$H$_4$-NO$_2$) | 404-12; Ph$_3$P$^+$-CH$_2$-C$_6$H$_4$-NO$_2$ Br$^-$ | 1373.9 | stirred at 60° C. over night |
| 404-31 (CsA-CH(OAc)-CH(CH$_3$)-CH$_2$-CH=CH-C(O)-OEt) | 404-12; Ph$_3$P$^+$-CH$_2$-C(O)OEt Br$^-$ | 1324.9 | stirred at 60° C. for 2 days |
| 404-33 (CsA-CH(OAc)-CH(CH$_3$)-CH$_2$-CH=CH-(1,3-dioxolan-2-yl)) | 404-29; Ph$_3$P$^+$-CH$_2$-(1,3-dioxolan-2-yl) Br$^-$ | 1325.0 | |
| 404-40 (CsA-CH(OAc)-CH(CH$_3$)-CH$_2$-CH=CH-(CH$_2$)$_6$CH$_3$) | 404-34; Ph$_3$P$^+$-(CH$_2$)$_7$CH$_3$ Br$^-$ | 1351.2 | |
| 404-43 (CsA-CH(OAc)-CH(CH$_3$)-CH$_2$-CH=CH-C(O)-CH$_3$) | 404-15; Ph$_3$P$^+$-CH$_2$-C(O)CH$_3$ Cl$^-$ | 1295.1 | stirred at reflux for 10 days |

-continued
| Compound | Starting Material | MS (Na+) | Remarks |
|---|---|---|---|
| 404-59 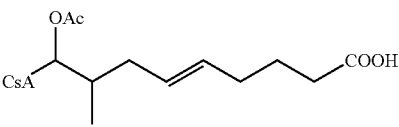 | 404-51 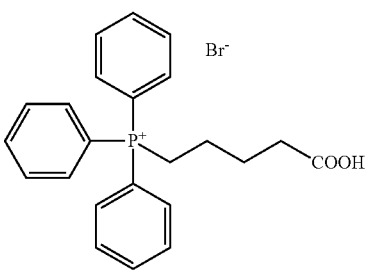 [SMILES: O=C(O)CCCC[P+](c1ccccc1)(c1ccccc1)c1ccccc1 ; [Br-]] | 1338.9 | 2 eq of KOtBu |
| 404-65 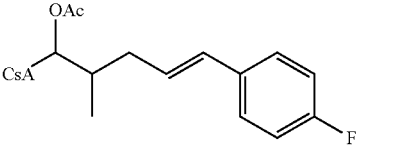 | 404-64 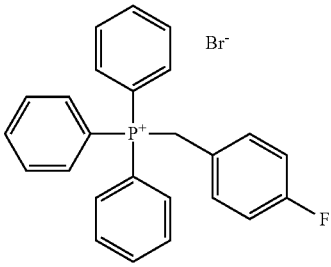 [SMILES: Fc1ccc(C[P+](c2ccccc2)(c2ccccc2)c2ccccc2)cc1 ; [Br-]] | 1347.1 | |
| 404-79 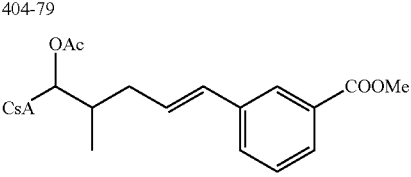 | 404-77 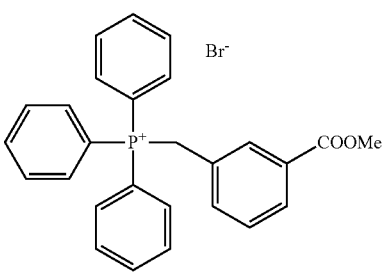 | 1386.9 | stirred at RT over night |
| 404-89 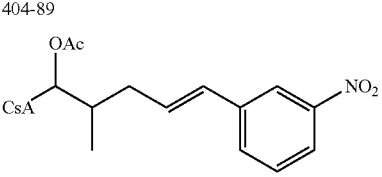 | 404-87 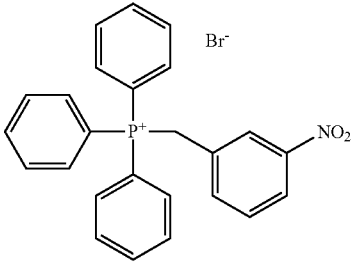 | 1374.1 | stirred at RT for 2 days |
| 404-134 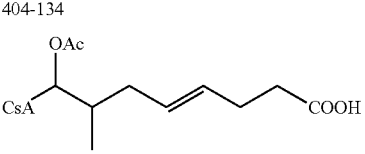 | 404-116 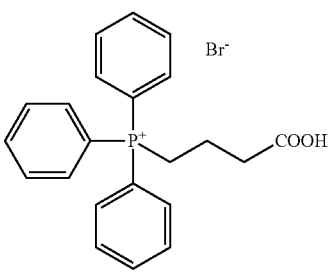 | 1325.0 | 2 eq of KOtBu; stirred at RT for 2 days |

-continued

| Compound | Starting Material | MS (Na+) | Remarks |
|---|---|---|---|
| 404-163 (CsA-CH(OAc)-CH(Me)-CH2-CH=CH-C(O)-CH2CH3) | 404-161 (Ph3P+-CH2-C(O)-CH2CH3 Br−) | 1308.8 | stirred at reflux for 15 days |
| 404-187 (CsA-CH(OAc)-CH(Me)-CH2-CH=CH-CH2-CN) | 404-170 (Ph3P+-CH2CH2CH2-CN Br−) | 1305.9 | stirred at RT over night |
| 416-04 (CsA-CH(OAc)-CH(Me)-CH2-CH=CH-(CH2)3-COOH) | 416-02 (Ph3P+-(CH2)4-COOH Br−) | 1353.0 | 2 eq of KOtBu |
| 416-09 (CsA-CH(OAc)-CH(Me)-CH2-CH=CH-(CH2)3-CH3) | 416-01 (Ph3P+-(CH2)4-CH3 Br−) | 1323.1 | |
| 420-40 (CsA-CH(OAc)-CH(Me)-CH2-CH=CH-(CH2)4-COOMe) | 420-32 (Ph3P+-(CH2)5-COOMe Br−) | 1381.0 | stirred at RT over night |

-continued

| Compound | Starting Material | MS (Na⁺) | Remarks |
|---|---|---|---|
| 420-85 CsA-CH(OAc)-CH(CH₃)-CH₂-CH=CH-(CH₂)₉COOH | 420-78 Ph₃P⁺-(CH₂)₉COOH Br⁻ | 1423.1 | 2 eq of KOtBu |
| 420-89 CsA-CH(OAc)-CH(CH₃)-CH₂-CH=CH-CH₂-CN | 420-80 Ph₃P⁺-CH₂-CH₂-CN Br⁻ | 1291.9 | |
| 420-92 CsA-CH(OAc)-CH(CH₃)-CH₂-CH=CH-(CH₂)₆COOH | 420-82 Ph₃P⁺-(CH₂)₆COOH Br⁻ | 1381.1 | 2 eq of KOtBu |
| 420-96 CsA-CH(OAc)-CH(CH₃)-CH₂-CH=CH-(CH₂)₅-OH | 404-78 Ph₃P⁺-(CH₂)₅-OH Br⁻ | 1338.9 | |
| 420-101 CsA-CH(OAc)-CH(CH₃)-CH₂-CH=CH-(CH₂)₅-CN | 419-132 Ph₃P⁺-(CH₂)₅-CN Br⁻ | 1347.9 | |

Deacetylation

Reaction 4: Deacetylation of Acetylated Cyclosporine Analogues

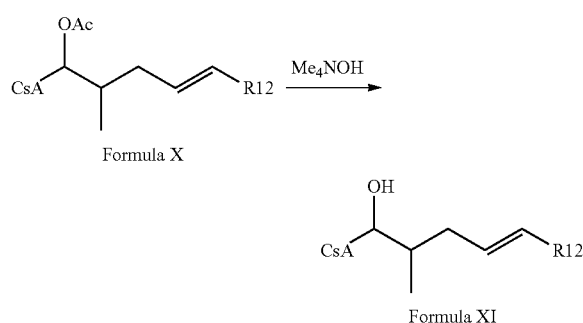

Formula X

Formula XI

Where R12 is a saturated or unsaturated, straight or branched aliphatic chain, optionally containing a substituent selected from the group of ketones, hydroxyls, nitriles, carboxylic acids, esters, amides, acyl-protected amines and 1,3-dioxolanes; an aromatic group, optionally containing a substituent selected from the group of halides, esters, amines and nitro; or a combination of the aforementioned saturated or unsaturated, straight or branched aliphatic chain and the aforementioned aromatic groups.

Example 4: Synthesis of Compound 404-90 Though Deacetylation

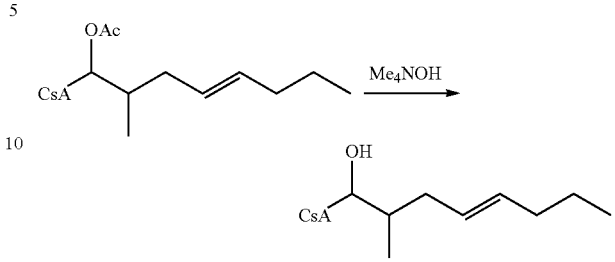

As an illustrative example, a solution of 404-20 (0.16 mmol) in 10 mL MeOH is combined with a solution of tetramethylammoniumhydroxide pentahydrate (0.47 mmol) in 2 mL $H_2O$. The mixture is stirred at room temperature for 2 days. The reaction is concentrated in vacuum and 5 mL 120 are added. The reaction is extracted with EtOAc, the extract is washed with brine, dried over $Na_2SO_4$ and concentrated to dryness. The crude product is purified by reversed phase preparative HPLC.

Purification of deacetylated compounds is generally carried out over silica gel (hexane/acetone 2:1) or by preparative HPLC. In the case of compounds 404-60, 404-137, 416-08, 420-98 and 420-100 (carboxylic acids), the reaction is acidified to pH 2-3 with 1 M HCl prior to extraction.

Using Reaction 4, the following compounds are further examples of the compounds that may be synthesized.

| Compound | Starting Material | MS ($Na^+$) |
|---|---|---|
| 404-22 | 404-16 | 1210.9 |
| 404-25 | 404-19 | 1287.0 |
| 404-36 | 404-33 | 1283.0 |
| 404-44 | 404-40 | 1309.1 |

-continued

| Compound | Starting Material | MS (Na+) |
|---|---|---|
| 404-58 | 404-57 | 1257.1 |
| 404-60 | 404-59 | 1297.1 |
| 404-61 | 404-56 | 1255.1 |
| 404-66 | 404-65 | 1305.1 |
| 404-81-1 | 404-79-1 | 1331.1 |
| 404-81-2 | 404-79-1 | 1345.1 |
| 404-85 | 404-83 | 1326.2 |
| 404-90 | 404-20 | 1253.0 |

-continued

| Compound | Starting Material | MS (Na+) |
|---|---|---|
| 404-96-1 ![CsA-CH(OH)-CH(Me)-CH2CH2CH2-C6H4-COOH] | 404-94 ![CsA-CH(OAc)-CH(Me)-CH2CH2CH2-C6H4-COOMe] | 1333.0 |
| 404-96-2 ![CsA-CH(OH)-CH(Me)-CH2CH2CH2-C6H4-COOMe] | 404-94 ![CsA-CH(OAc)-CH(Me)-CH2CH2CH2-C6H4-COOMe] | 1347.0 |
| 404-97 ![CsA-CH(OH)-CH(Me)-CH=CH-C6H4-NO2] | 404-89 ![CsA-CH(OAc)-CH(Me)-CH=CH-C6H4-NO2] | 1331.9 |
| 404-125 ![CsA-CH(OH)-CH(Me)-CH2CH2CH2-C6H4-NH2] | 404-120 ![CsA-CH(OAc)-CH(Me)-CH2CH2CH2-C6H4-NH2] | 1304.0 |
| 404-130 ![CsA-CH(OH)-CH(Me)-CH2CH2CH2-C(O)NH2] | 404-128 ![CsA-CH(OAc)-CH(Me)-CH2CH2CH2-C(O)NH2] | 1270.1 |
| 404-132 ![CsA-CH(OH)-CH(Me)-CH2CH2CH2-C(O)NMe2] | 404-129 ![CsA-CH(OAc)-CH(Me)-CH2CH2CH2-C(O)NMe2] | 1298.0 |
| 404-137 ![CsA-CH(OH)-CH(Me)-CH2-CH=CH-CH2-COOH] | 404-134 ![CsA-CH(OAc)-CH(Me)-CH2-CH=CH-CH2-COOH] | 1283.0 |
| 404-154 ![CsA-CH(OH)-CH(Me)-CH2-C(O)-CH=CH-CH2CH2-C(O)NMe2] | 404-150 ![CsA-CH(OAc)-CH(Me)-CH2-C(O)-CH=CH-CH2CH2-C(O)NMe2] | 1338.1 |

-continued

| Compound | Starting Material | MS (Na+) |
|---|---|---|
| 404-157 | 404-155 | 1310.0 |
| 404-173 | 404-172 | 1268.9 |
| 404-194 | 404-187 | 1263.9 |
| 416-08 | 416-04 | 1311.0 |
| 416-13 | 416-09 | 1281.1 |
| 420-17 | 420-08-1 | 1368.0 |
| 420-30-1 | 420-27 | 1312.0 |
| 420-43 | 420-40 | 1324.9 |

-continued

| Compound | Starting Material | MS (Na⁺) |
|---|---|---|
| 420-47 | 420-46 | 1327.0 |
| 420-98 | 420-85 | 1381.1 |
| 420-100 | 420-92 | 1339.1 |
| 420-102 | 420-96 | 1297.0 |
| 420-108 | 420-101 | 1305.9 |
| 420-117 | 420-109-1 | 1352.1 |
| 420-120 | 420-110-1 | 1410.0 |
| 420-122 | 420-107-2 | 1340.0 |

| Compound | Starting Material | MS (Na⁺) |
|---|---|---|
| 420-124 | 420-109-2 | 1354.0 |
| 420-125 | 420-110-2 | 1412.0 |
| 420-126 | 420-107-1 | 1337.9 |
| 420-131 | 420-130 | 1297.9 |
| 420-132 | 420-128-1 | 1380.0 |

Hydrogenation of the Double Bond

The double bond can be hydrogenated under atmospheric pressure to obtain the saturated side chain. Functional groups such as hydroxyl, carbonyl and carboxyl are stable under these conditions and do not require protection. R' represents either an acetyl group or hydrogen. In the case of α,β-unsaturated carbonyl compounds the double bond has to be reduced prior to deacetylation to avoid cyclization through a nucleophilic addition of the free hydroxy group on the activated double bond.

Where R12 is a saturated or unsaturated, straight or branched aliphatic chain, optionally containing a substituent selected from the group of ketones, hydroxyls, nitriles, carboxylic acids, esters, amides, acyl-protected amines and 1,3-dioxolanes; an aromatic group, optionally containing a substituent selected from the group of halides, esters, amines and nitro; or a combination of the aforementioned saturated or unsaturated, straight or branched aliphatic chain and the aforementioned aromatic groups, and R' is either a H or an acetyl group.

Reaction 5

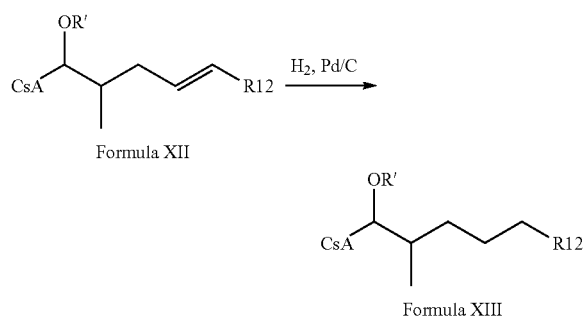

Example 5: Synthesis of 404-56

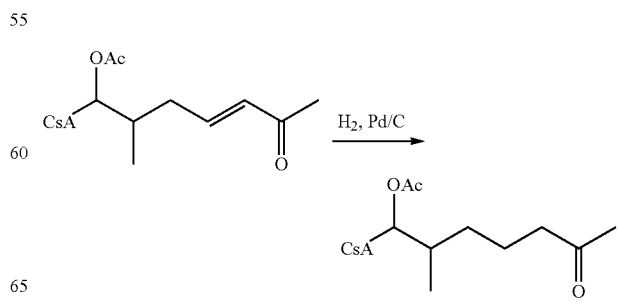

As an illustrative example, 404-43 (0.34 mmol) is dissolved in 40 mL anhydrous EtOH and 43 mg Pd/C (10%) and 0.2 mL acetic acid are added. The mixture is stirred under hydrogen at atmospheric pressure for 2 days. The reaction is filtered through Celite and is concentrated in vacuum. The crude product is purified by preparative HPLC.

Using Reaction 5, the following compounds are further examples of the compounds that may be synthesized.

| Compound | Starting Material | MS (Na$^+$) |
|---|---|---|
| 404-50 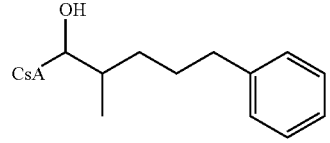 | 404-25 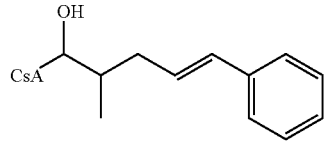 | 1289.1 |
| 404-56 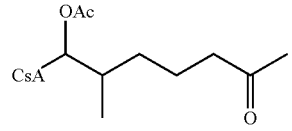 | 404-43 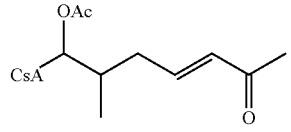 | 1297.0 |
| 404-57 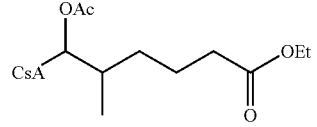 | 404-31 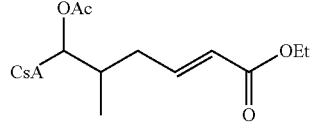 | 1327.1 |
| 404-63 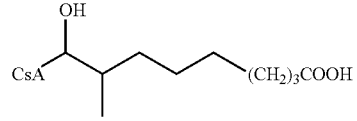 | 404-60 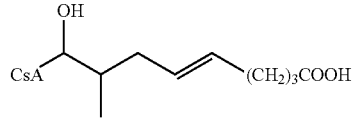 | 1299.1 |
| 404-74 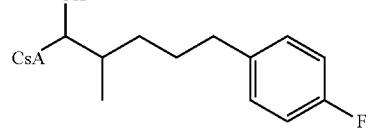 | 404-66 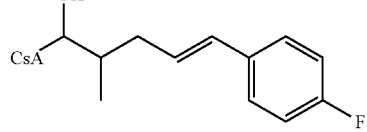 | 1307.1 |
| 404-92 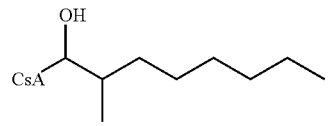 | 404-90 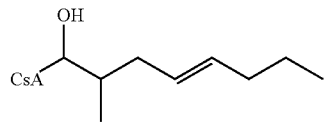 | 1255.1 |
| 404-94 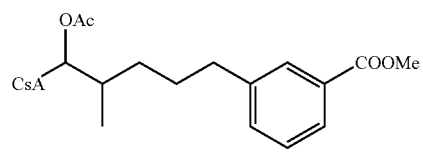 | 404-79 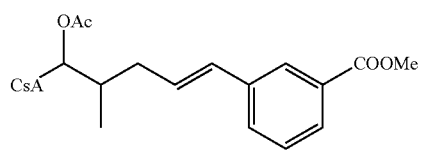 | 1388.9 |
| 404-168 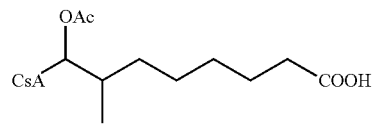 | 404-134 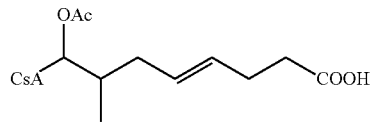 | 1326.8 |

| Compound | Starting Material | MS (Na+) |
|---|---|---|
| 404-172 | 404-163 | 1310.9 |
| 420-19 | 416-08 | 1313.0 |
| 420-46 | 420-40 | 1383.1 |
| 420-68 | 420-134 | 1326.9 |
| 420-106 | 420-98 | 1383.1 |
| 420-111 | 420-100 | 1341.0 |
| 420-112 | 420-102 | 1298.9 |
| 420-130 | 420-123 | 1340.0 |

Reduction of the Nitrile Group

Reduction of the nitrile group to the corresponding primary amine can be achieved with nickel boride generated in situ from sodium borohydride (NaBH$_4$) and nickel(II)chloride (NiCl$_2$). Addition of a suitable trapping reagent leads to acyl-protected primary amines (carbamates or amides, respectively) and prevents the formation of secondary amines as an undesired side reaction. The double bond is partially reduced under the given conditions and a product mixture is obtained. Both, saturated and unsaturated protected amine compounds were isolated and purified. For reaction 420-123 the mixture was not separated. Instead, the mixture underwent catalytic hydrogenation to produce the fully saturated compound.

Reaction 6

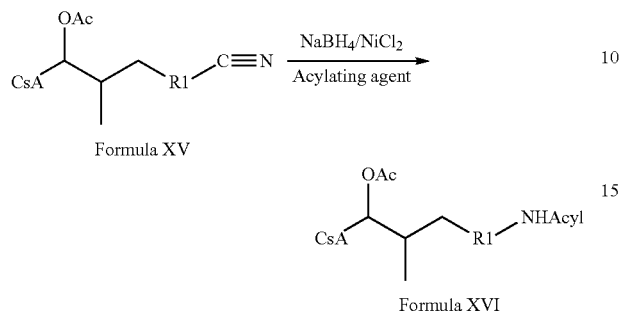

Formula XV → Formula XVI

Where Acyl is any one of BOC, acetyl, or butyryl, acylating agent is any one of di-tert-butyldicarbonate, acetic anhydride, and butyric anhydride and R1 is a saturated or unsaturated straight chain or branched aliphatic group. It would be understood by one skilled in the art that the acylating agents described above may be replaced with a broad range of acylating agents to produce a similarly broad range of acyl-protected amines.

Example 6: Synthesis of 420-08

420-08-1
+
420-08-2

As an illustrative example, 404-187 (0.257 mmol) is dissolved in 15 mL methanol and cooled to 0° C. Di-tert-butyldicarbonate (0.514 mmol) and nickel(II)chloride (0.025 mmol) are added to give a clear solution. Sodium borohydride (3.85 mmol) is added in portions over 1 hour. The resulting mixture is stirred at ambient temperature over night. Additional sodium borohydride (1.95 mmol) is added at 0° C. and stirring is continued for 3 hours at room temperature. HPLC shows a mixture of 420-08-1 (carbamate compound) and 420-08-2 (carbamate compound with double bond reduced). The reaction is stirred for 30 minutes with diethylenetriamine (0.257 mmol) and is then concentrated in vacuum. The residue is taken up in 75 mL EtOAc, washed with 20 mL sat. $NaHCO_3$ solution and dried over $Na_2SO_4$. The solvent is removed in vacuum. The crude product is purified by preparative HPLC.

Using Reaction 6, the following compounds are further examples of the compounds that may be synthesized.

| Compound | Starting Material | Protecting Reagent | MS ($Na^+$) |
|---|---|---|---|
| 420-08-1 | 404-197 | di-tert-butyldicarbonate | 1410.0 |
| 420-08-2 | 404-197 | di-tert-butyldicarbonate | 1412.1 |
| 420-107-1 | 404-197 | butyric anhydride | 1379.9 |

-continued

| Compound | Starting Material | Protecting Reagent | MS (Na+) |
|---|---|---|---|
| 420-107-2 | 404-197 | butyric anhydride | 1382.1 |
| 420-109-1 | 420-101 | acetic anhydride | 1394.1 |
| 420-109-2 | 420-101 | acetic anhydride | 1396.1 |
| 420-110-1 | 420-101 | di-tert-butyldicarbonate | 1452.1 |
| 420-110-2 | 420-101 | di-tert-butyldicarbonate | 1454.1 |
| 420-123 [1] | 420-89 | acetic anhydride | 1337.9/ 1339.9 |
| 420-128-1 | 420-101 | butyric anhydride | 1422.1 |
| 420-128-2 | 420-101 | butyric anhydride | 1424.1 |

[1] mixture not separated

Amine Deprotection

The BOC protected amine (carbamate) can be converted into the free amine by acidic hydrolysis using trifluoroacetic acid (TFA).

Reaction 7

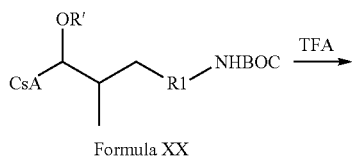

Formula XX

As an illustrative example, 420-17 (0.026 mmol) is dissolved in 4 mL anhydrous DCM and 2 mL trifluoroacetic acid is added at 0° C. The reaction is stirred at room temperature for 3 hours. Twenty 20 mL dichloromethane is added. The reaction mixture is washed with $H_2O$ and sat. $NaHCO_3$ solution and is dried over $Na_2SO_4$. The solvent is removed and the crude product is purified by preparative HPLC.

Using Reaction 7, the following compounds are further examples of the compounds that may be synthesized.

| Compound | Starting Material | MS (M + 1) |
|---|---|---|
| 420-23 | 420-17 | 1246.0 |
| 420-25 | 420-13 | 1290.0 |
| 420-129 | 420-120 | 1288.0 |

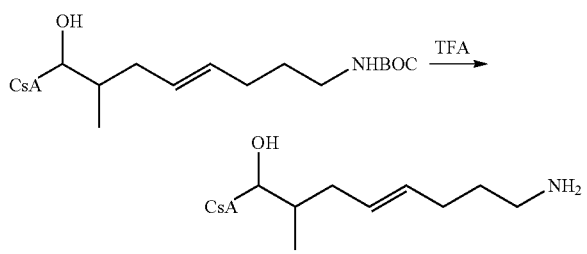

-continued

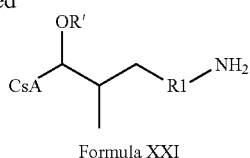

Formula XXI

Where R1 is a saturated or unsaturated, straight or branched aliphatic chain, and R' is either a H or an acetyl group.

Example 7: Synthesis of 420-23

Protection of the Amino Group

The free amino function can be protected using a wide range of protecting groups using established methods. A broader range of protecting agents is available compared to the reductive introduction starting from the nitrile. Together, reactions 7 and 8 offer an alternate route to reaction 6 for the preparation of acyl-protected amino compounds.

Reaction 8

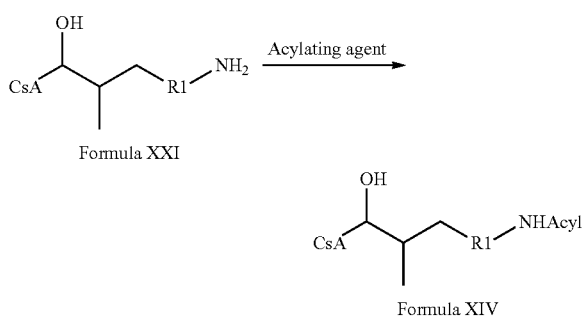

Formula XIV

Where Acyl is any one of BOC, acetyl or butyryl, acylating agent is any one of di-tert-butyldicarbonate, acetic anhydride, butyric anhydride, it would be understood by one skilled in the art that a broad range of acylating agents including, dicarbonates, anhydrides and acyl halides can be employed to produce a broad range of acyl-protected amines, and R1 is a saturated or unsaturated straight chain or branched aliphatic group.

Example 8: Synthesis of 420-27

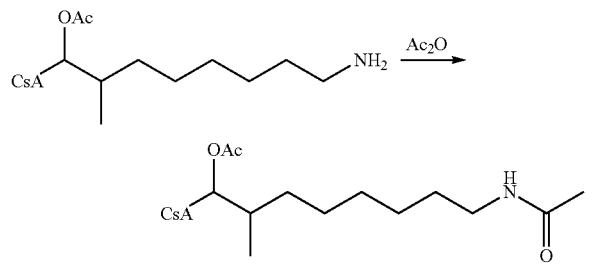

As an illustrative example, 420-25 (0.039 mmol) is dissolved in 3 mL anhydrous pyridine under nitrogen. The reaction is cooled to 0° C. and acetic anhydride (0.59 mmol) is added. The mixture is stirred at ambient temperature overnight. The solvent is removed in vacuum and the residue is taken up in 25 mL EtOAc. The reaction is washed with 2×10 mL 1 M HCl, 2×10 mL sat. $NaHCO_3$ solution and 10 mL brine and is dried over $Na_2SO_4$. The solvent is removed in vacuum to give the product as a colorless solid.

Deprotection of Aldehyde

The 1,3-dioxolane moiety is converted into an aldehyde function through acidic hydrolysis.

Reaction 9 and Example 9: Synthesis of 404-47

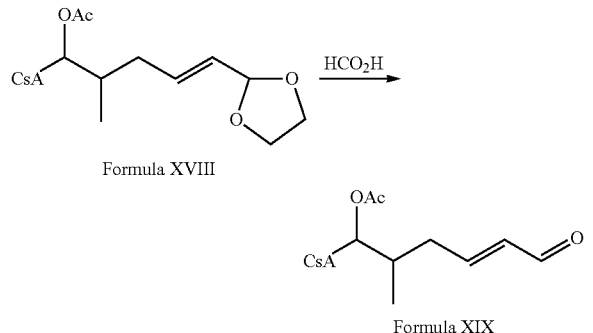

As an illustrative example, a solution of 404-33 (0.246 mmol) in 20 mL formic acid is stirred at room temperature for 45 minutes. One hundred mL ice-water and 200 mL sat. $NaHCO_3$ solution are added slowly to the reaction (strong foaming). The reaction is extracted with 2×150 mL EtOAc. The combined extracts are washed with sat. $NaHCO_3$ solution, water and brine and are dried over $Na_2SO_4$. The solvent is removed and the product is dried in vacuum.

Reduction of the Nitro Group

The aromatic nitro compound is reduced to the aniline through catalytic hydrogenation. The reaction leads to the reduction of the double bond.

Reaction 10 and Example 10: Synthesis of 404-120

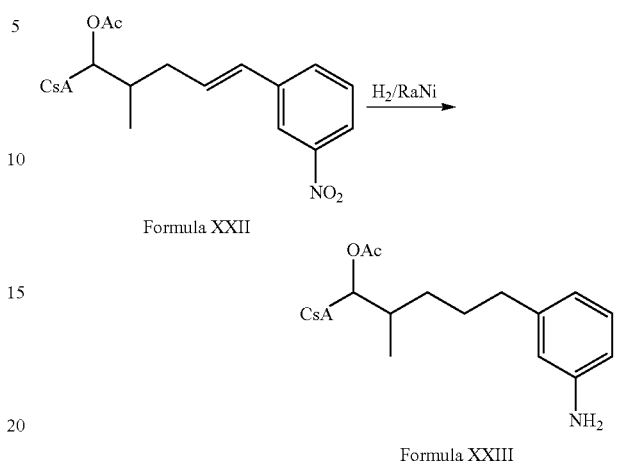

As an illustrative example, 404-89 (0.13 mmol) is dissolved in 2 mL ethanol and Raney-Nickel (0.18 g, 50% in $H_2O$, washed 3 times with ethanol, then suspended in 2 mL ethanol) and 0.1 mL acetic acid are added. The reaction is stirred at room temperature for 2 days. The reaction is filtered through Celite and the filter cake is washed with methanol. The filtrate is brought to dryness. The residue is taken up in EtOAc, washed with $NaHCO_3$ solution and brine and is dried over $Na_2SO_4$. The solvent is removed in vacuum. The crude product is purified over silica gel (hexane/acetone 2:1).

Amide Synthesis

Amides are prepared from carboxylic acids by reaction of an amine with the corresponding acid chloride (Reaction 11). The synthesis can also proceed directly from the acid by use of appropriate coupling reagents, such as DCC and HOBt (Reaction 12).

Reaction 11

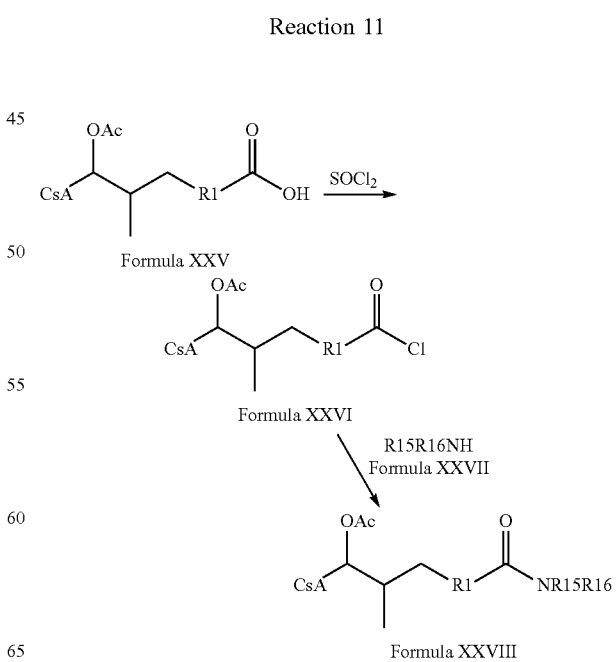

Where R1 is a saturated or unsaturated, straight or branched aliphatic chain, R15 and R16 are independently hydrogen or a saturated or unsaturated, straight or branched aliphatic chain, or where NR15R16 together forms a morpholinyl moiety.

Using Reaction 11, the following compounds are further examples of the compounds that may be synthesized.

| Compound | Starting Material | MS (Na+) | Amine |
|---|---|---|---|
| 404-83 | 365-73 | 1368.2 | diethylamine |
| 404-128 | 404-124 | 1311.9 | anhydrous ammonia [1] |
| 404-129 | 404-124 | 1340.1 | Dimethylamine [2] |

[1] passed through reaction for 10 min at 0° C.;
[2] 2M solution in THF

Example 11: Synthesis of 404-85

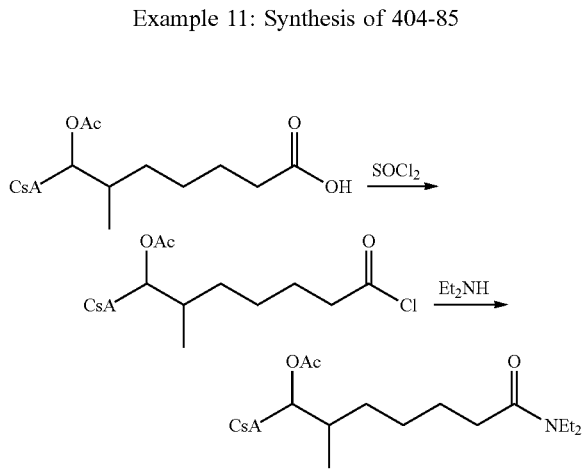

As an illustrative example, 365-73 (0.04 mmol) and thionylchloride (68 mmol) are combined under nitrogen atmosphere and are heated to reflux for 2 hours. The reaction is allowed to cool and is concentrated to dryness. Twenty mL toluene Is added and the reaction is concentrated to dryness again (2 times). The residue is taken up in 5 mL anhydrous toluene and diethylamine (0.48 mmol) is added. The reaction is stirred at room temperature over night. Five mL H$_2$O are added and the mixture is extracted with 20 mL EtOAc. The extract is washed with brine and dried over Na$_2$SO$_4$. The solvent is removed in vacuum and the crude product is purified over silica gel (hexane/acetone 3:1).

Reaction 12

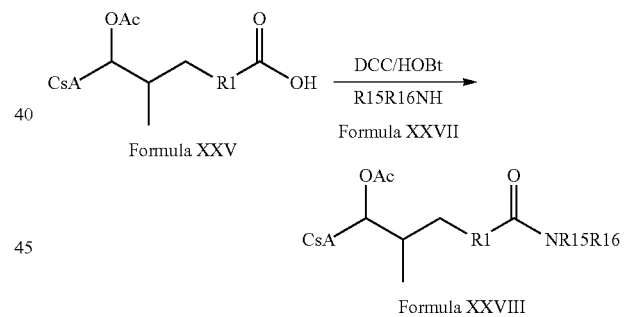

Where R1 is a saturated or unsaturated, straight or branched aliphatic chain, R15 and R16 are independently hydrogen or a saturated or unsaturated, straight or branched aliphatic chain, or where NR15R16 together forms a morpholinyl moiety.

Example 12: Synthesis of 420-104

As an illustrative example, 420-98 (0.078 mmol) is dissolved in 10 mL anhydrous DCM under nitrogen atmosphere. Dicyclohexylcarbodiimide (DCC, 0.117 mmol) and 1-hydroxybenzotriazole hydrate (HOBt, 0.078 mmol) are added at 0° C. and the mixture is stirred for 15 minutes. Dimethylamine (0.78 mmol) is added to give a clear, colorless solution. The cooling bath is removed after 15 minutes and stirring is continued at ambient temperature for 5 days. The reaction is transferred to a separatory funnel and 20 mL DCM and 10 mL 0.5 M HCl are added. The organic layer is taken off, dried over $Na_2SO_4$ and concentrated to dryness. The residue is taken up in 10 mL acetonitrile. Undissolved solid is filtered off and the filtrate is concentrated in vacuum. The crude product is purified by preparative HPLC.

Using Reaction 12, the following compounds are further examples of the compounds that may be synthesized.

| Compound | Starting Material | MS ($Na^+$) | Amine |
|---|---|---|---|
| 404-150 | 416-04 | 1380.1 | Dimethylamine [2] |
| 404-155 | 404-134 | 1352.1 | Dimethylamine [2] |
| 404-156 | 404-60 | 1324.1 | Dimethylamine [2] |
| 404-162 | 416-08 | 1379.9 | Morpholine |
| 404-164 | 416-08 | 1309.8 | anhydrous ammonia [1] |
| 404-178 | 404-137 | 1323.9 | Propylamine |
| 420-104 | 420-98 | 1408.1 | Dimethylamine [2] |

| Compound | Starting Material | MS (Na⁺) | Amine |
|---|---|---|---|
| 420-114 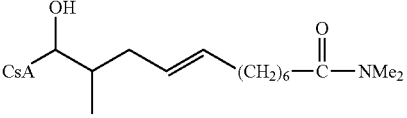 | 420-100 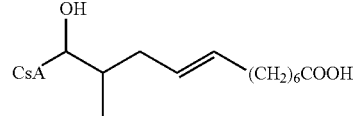 | 1366.0 | Dimethyl-amine [2] |
| 420-121 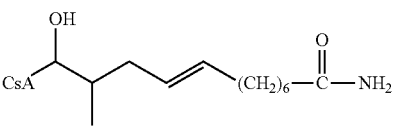 | 420-100 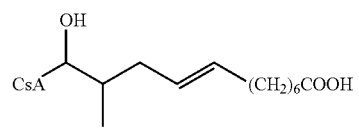 | 1338.0 | anhydrous ammonia [1] |

[1] passed through reaction for 10 min at 0° C.;
[2] 2M solution in THF

Esterification

Carboxylic acid esters are prepared from the corresponding carboxylic acids and an alcohol either using acidic catalysis (Reaction 13) or coupling reagents (DCC and DMAP, Reaction 14).

Reaction 13

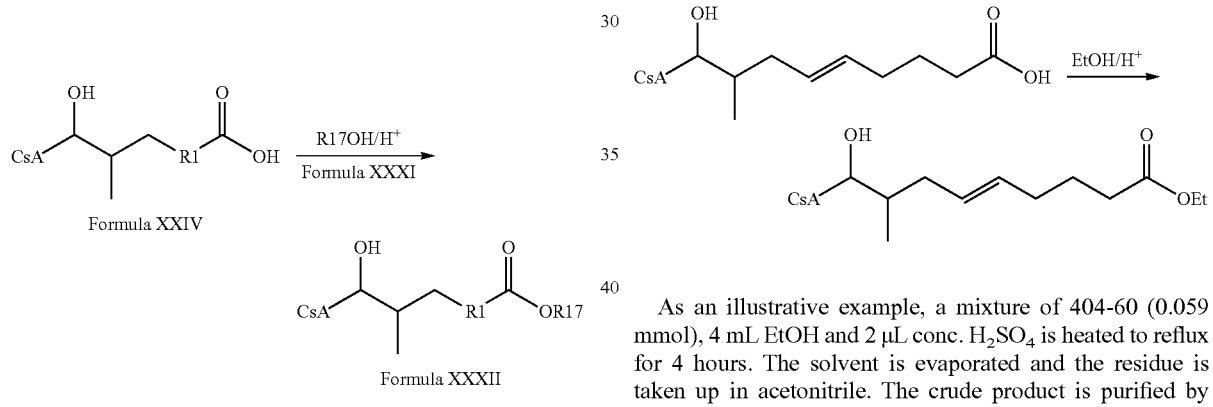

Where R1 is a saturated or unsaturated, straight or branched aliphatic chain, and R17 is a saturated or unsaturated, straight or branched aliphatic chain, optionally containing a halogen or hydroxyl substituent.

Example 13: Synthesis of 404-171

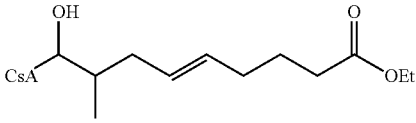

As an illustrative example, a mixture of 404-60 (0.059 mmol), 4 mL EtOH and 2 μL conc. $H_2SO_4$ is heated to reflux for 4 hours. The solvent is evaporated and the residue is taken up in acetonitrile. The crude product is purified by preparative HPLC.

Using Reaction 13, the following compounds are further examples of the compounds that may be synthesized.

| Compound | Starting Material | MS (Na⁺) | Reagent |
|---|---|---|---|
| 404-171 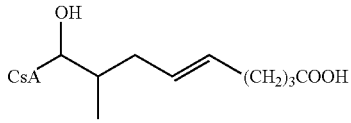 | 404-60 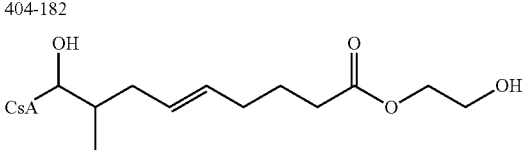 | 1368.2 | ethanol |
| 404-182 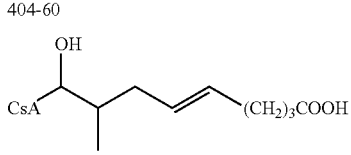 | 404-60 | 1311.9 | ethylene glycol [1] |

-continued

| Compound | Starting Material | MS (Na⁺) | Reagent |
|---|---|---|---|
| 420-103 | 420-98 | 1409.1 | ethanol |
| CsA—CH(OH)—CH(CH₃)—CH₂—CH=CH—(CH₂)₃COOEt | CsA—CH(OH)—CH(CH₃)—CH₂—CH=CH—(CH₂)₉COOEt | | |
| 420-113 | 420-100 | 1366.9 | ethanol |
| CsA—CH(OH)—CH(CH₃)—CH₂—CH=CH—(CH₂)₆COOEt | CsA—CH(OH)—CH(CH₃)—CH₂—CH=CH—(CH₂)₆COOH | | |

¹ 3 hours at 90° C.; product extracted with EtOAc

Reaction 14

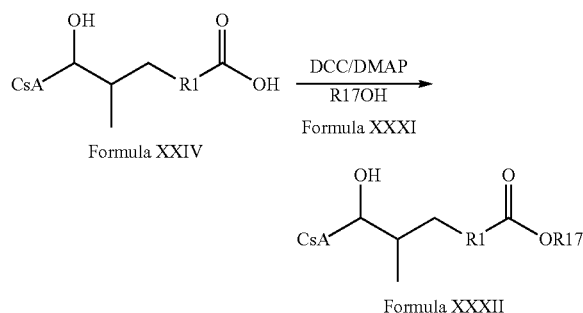

Where R1 is a saturated or unsaturated, straight or branched aliphatic chain, and R17 is a saturated or unsaturated, straight or branched aliphatic chain, optionally containing a halogen or hydroxyl substituent.

Example 14: 420-24

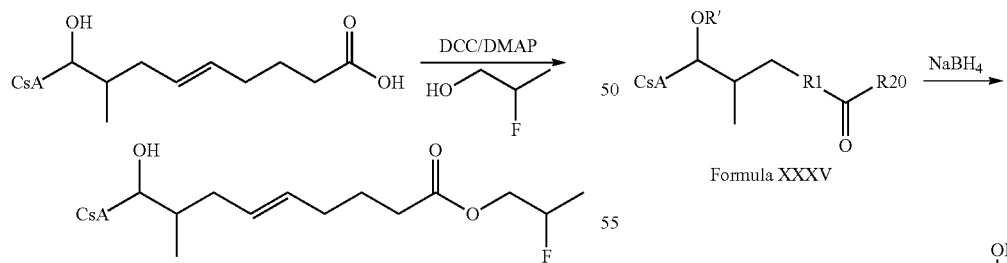

As an illustrative example, 404-60 (0.053 mmol) is dissolved in 4 mL anhydrous DCM and cooled to 0° C. under nitrogen atmosphere. Dimethylaminopyridine (DMAP, 0.005 mmol), 2-fluoropropanol (0.27 mmol) and dicyclohexylcarbodiimide (DCC, 0.058 mmol) are added and the reaction is stirred for 15 min at 0° C. The cooling bath is removed and stirring is continued over night at ambient temperature. 20 mL DCM are added, the reaction is then washed with H₂O and evaporated to dryness. The residue is taken up in 10 mL acetonitrile and filtered. The filtrate is concentrated in vacuum. The crude product is purified by preparative HPLC.

Alcohols

Besides direct synthesis in the Wittig reaction, alcohols are obtained through a number of reactions. Reduction of a carbonyl group with sodium borohydride leads to primary (starting from aldehyde) or secondary (starting from ketone) alcohols, respectively.

Oxidation of a double bond through the hydroboration method can lead to a mixture of isomers. The reaction proceeds predominantly in anti-Markovnikov orientation. In the case of a terminal olefin the primary alcohol is the main product.

An olefin can be converted into a diol through oxidation with hydrogen peroxide. Reaction of a carbonyl compound with a Grignard reagent leads to secondary (starting from aldehyde) and tertiary (starting from ketone) alcohols. This method allows for an extension of the carbon chain.

Reaction 15

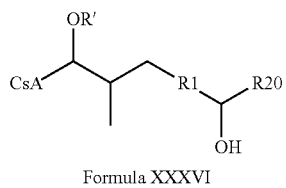

Where R' is a H or acetyl, R1 is a saturated or unsaturated, straight or branched aliphatic chain, and R20 is a saturated or unsaturated, straight or branched aliphatic chain.

Example 15: Synthesis of 404-98

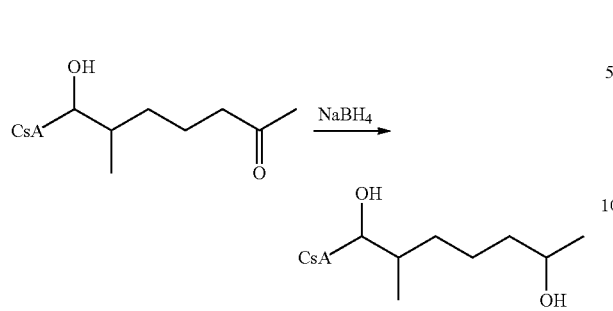

As an illustrative example, 404-61 (0.0365 mmol) is dissolved in 4.5 mL anhydrous EtOH under nitrogen atmosphere. Sodium borohydride (0.15 mmol, suspended in 0.5 mL anhydrous EtOH) is added at 0° C. and the resulting mixture is stirred at ambient temperature over night. Additional sodium borohydride (0.08 mmol) is added and stirring is continued over night. The reaction is quenched with 5 mL 1 M HCl under ice-bath cooling and is extracted with EtOAc. The extract is washed with brine, dried over $Na_2SO_4$ and concentrated to dryness. The crude product is purified by preparative HPLC.

Using Reaction 15, the following compounds are further examples of the compounds that may be synthesized.

Reaction 16

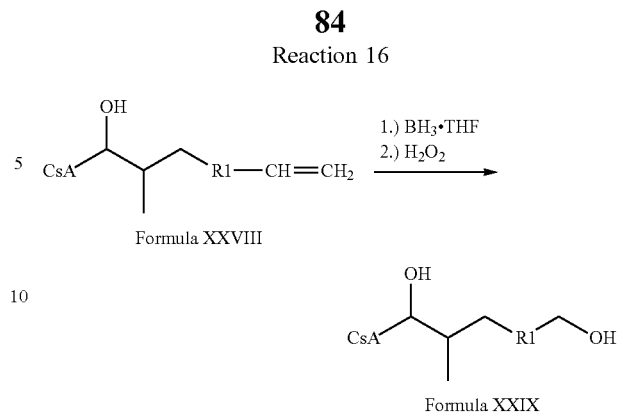

Where R1 is a saturated or unsaturated, straight or branched aliphatic chain.

Example 16: Synthesis of 420-28-1

| Compound | Starting Material | MS (Na⁺) |
|---|---|---|
| 404-98 | 404-61 | 1256.9 |
| 404-195 | 404-173 | 1271.0 |
| 404-198 | 404-172 | 1313.0 |
| 420-09 | 404-56 | 1298.9 |

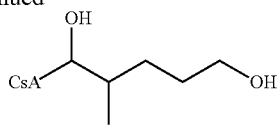

As an illustrative example, 404-16 (0.081 mmol) is dissolved under nitrogen atmosphere in 4 mL anhydrous THF. The reaction is cooled to 0° C. and $BH_3$.THF (1 M sol. in THF, 0.06 mmol) is added. The reaction is stirred at room temperature over night. HPLC shows the reaction is incomplete. Additional $BH_3$.THF (0.5 mmol) is added and stirring is continued for 4 hours at room temperature. The reaction is cooled to 0° C. and 10 mL 1 M NaOH and 0.30 mL 30% hydrogen peroxide solution are added. The mixture is stirred at room temperature over night. The reaction is extracted with 25 mL EtOAc. The extract is washed with brine, dried over $Na_2SO_4$ and concentrated to dryness. The product is purified by preparative HPLC.

Reaction 17

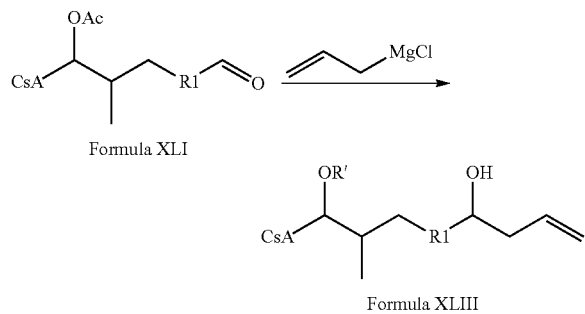

Where R1 is a saturated or unsaturated, straight or branched aliphatic chain, R' is either a H or an acetyl group.

Example 17: Synthesis of 420-49

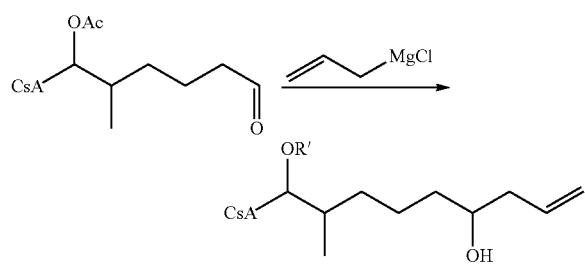

As an illustrative example, 420-49 (0.037 mmol) is dissolved under argon atmosphere in 5 mL anhydrous THF. The reaction is cooled to −70° C. and allylmagnesium chloride (1 M sol. in THF, 0.22 mmol) is added. The reaction is stirred for 15 minutes at −70° C. and is then allowed to come to room temperature. After 90 minutes the reaction is quenched with sat. $NH_4Cl$ solution. The reaction is extracted with 25 mL EtOAc. The extract is washed with brine, dried over $Na_2SO_4$ and concentrated to dryness. The product is purified by preparative HPLC. A mixture of acetylated and deacetylated compound is obtained.

Reaction 18

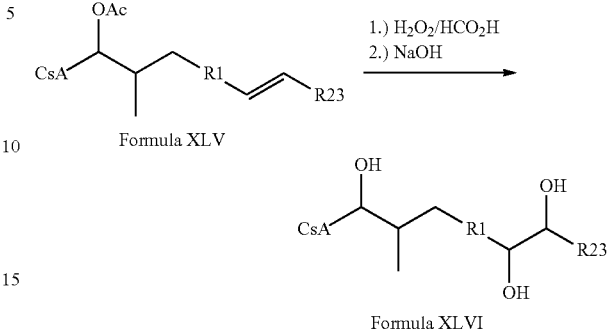

Where R1 is a saturated or unsaturated, straight or branched aliphatic chain, and R23 is a saturated or unsaturated, straight or branched aliphatic chain.

Example 18: Synthesis of 404-126

As an illustrative example, 404-16 (0.054 mmol) is dissolved in 1 mL formic acid and hydrogen peroxide (30% aqueous solution, 0.52 mmol) is added. The reaction is stirred at room temperature over night and is then concentrated to dryness. The residue is dissolved in 25 mL EtOAc, washed with sat. $NaHCO_3$ solution and dried over $Na_2SO_4$. The solvent is removed in vacuum. The reaction is taken up in 9 mL THF and 3 mL 1 M NaOH, and is stirred for 4 hours at room temperature. The solvent is removed and the residue is partitioned between 25 mL EtOAc and 5 mL $H_2O$. The organic layer is washed with brine and dried over $Na_2SO_4$. The solvent is evaporated and the crude product is purified by preparative HPLC.

Example 19: Modification of Amino Acid 3

CsA undergoes substitution on AA3 as outlined below. Reaction with excess LDA (lithium diisopropylamide) leads to a hexalithio derivative containing four lithium azaenolate units as well as a lithium alkoxide unit on the amino acid 1 side chain and a lithium enolate unit on AA3, respectively. Subsequent reaction with a suitable electrophile generates substitution products on the AA3 (sarcosine) residue. Suitable electrophiles are e.g. alkyl halides, aldehydes, carbon dioxide and alkyl disulfides (Table 1). Both D and L epimers can be obtained, with the relative ratios depending on the reaction conditions. Route A (see below) leads predominantly to the D product, while Route B (addition of excess LiCl) gives mixtures of both epimers.

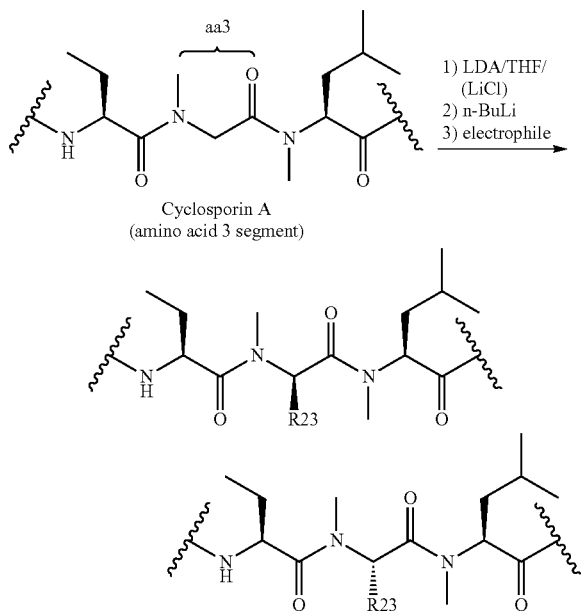

Example 19: Substitution Reaction at AA3 of Cyclosporin A. D and L Stereoisomers are Obtained Route A: [D-MeSar]³-CsA An oven dried flask is charged under argon atmosphere with 160 mL anhydrous THF and diisopropylamine (2.07 mL, 14.8 mmol). The solution is cooled to −78° C. and n-butyl lithium (2.5 M in hexane, 5.4 mL, 135 mmol) is added. After stirring for 30 minutes, CsA (2.40 g, 2.0 mmol, dissolved in 40 mL anhydrous THF) is added. The reaction is stirred for 1 hour at −78° C. Additional n-butyl lithium (3.2 mL, 8.0 mmol) is added, followed by addition of methyl iodide (1.25 mL, 20.0 mmol). Stirring is continued at −78° C. far 1.5 hours, and then the reaction is allowed to warm to room temperature over an additional 1.5 hours. 20 mL H₂O are added and the THF is removed in vacuum. Additional 50 mL H₂O are added and an extraction is carried out with 150 mL EtOAc. The extract is washed with brine and dried over Na₂SO₄. The solvent is removed in vacuum and the crude product is purified over silica gel (hexane/acetone 3:1). Yield: 0.74 g (0.61 mmol, 30%).

Route B: [MeSar]³-CsA

A dry 100 mL flask is charged under argon atmosphere with 7.5 mL anhydrous THF and diisopropylamine (0.46 mL, 3.3 mmol). The solution is cooled to 0° C. and n-butyl lithium (1.32 mL, 2.5 M solution in hexane, 3.3 mmol) is added. The reaction is stirred for 20 minutes at 0° C. and is then cooled to −78° C. A solution of CsA (601 mg, 0.5 mmol) and lithium chloride (636 mg, 15 mmol) in 12 mL anhydrous THF is prepared and cooled to −78° C. under argon atmosphere. The LDA solution is then transferred into this mixture through a cannula. The reaction is stirred at −78° C. for 2 hours. Additional n-butyl lithium (1.20 mL, 3.0 mmol) is added, followed by methyl iodide (0.62 mL, 10 mmol). The mixture is allowed to warm to −20° C. and stirred at this temperature for 3 hours. The reaction is allowed to warm to room temperature, quenched with saturated NH₄Cl solution, extracted with EtOAc (2×20 mL), washed with brine and dried over Na₂SO₄. The solvent is removed in vacuum and the crude product is purified over silica gel (hexane/acetone 3:1). Yield: [L-MeAla³]-CsA: 302 mg (0.25 mmol, 50%). [D-MeAla³]-CsA: 76 mg (0.06 mmol, 12%).

TABLE 1

Examples of possible electrophilee used for the alkylation of the 3-position of Cyclosporin.

| Electrophile | R23[1] | Route | Remarks |
|---|---|---|---|
| methyl iodide | —CH₃ | A/B | — |
| ethyl iodide | —CH₂CH₃ | A/B | — |
| allyl bromide | —CH₂CHCH₂ | B | — |
| 1,3-diiodopropane | —CH₂CH₂CH₂I | B | — |
| 1,4-diiodobutane | —(CH₂)₃CH₂I | B | — |
| trimethylammonium-3-iodopropane hexafluorophosphate | —(CH₂)₃N⁺(CH₃)₃ | B | — |
| propargyl bromide | —CH₂CCH | A | 10 equiv electrophile; stirred for 1 h at room temperature after electrophile addition |
| tert-butyl bromoacetate | —CH₂CO₂(t-Bu) | A | 5 equiv electrophile; stirred for 1 h at room temperature after electrophile addition |
| benzyl bromide | —CH₂Ph[2] | A | 15 equiv LDA and 30 equiv electrophile; stirred for 6 h at −75° C. and 10 h at room temperature after electrophile addition |
| formaldehyde | —CH₂OH | A | formaldehyde prepared from paraformaldehyde at 170° C. prior to addition |
| acetaldehyde | —CH(OH)CH₃ | B | stirred for 2.5 h at −78° C. after electrophile addition |
| pivalaldehyde | —CH(OH)(t-Bu)[3] | B | stirred for 70 min at −78° C. after electrophile addition |
| benzaldehyde | —CH(OH)Ph | B | stirred for 2.5 h at −78° C. after electrophile addition |
| carbon dioxide | —COOH | A | CO₂ gas passed for 15 min |

TABLE 1-continued

Examples of possible electrophilee used for the alkylation of the 3-position of Cyclosporin.

| Electrophile | R23[1] | Route | Remarks |
|---|---|---|---|
| | | | through reaction mixture at −78° C.; stirred for 1 h at −78° C. after electrophile addition |
| dimethyl disulfide | —SCH$_3$ | B | stirred for 18 h at 0° C. after electrophile addition |
| p-tolyl disulfide | —S(p-Tol)[4] | B | stirred for 18 h at 0° C. after electrophile addition |

[1]according to Example 19
[2]Ph = phenyl;
[3]t-Bu = tert-butyl;
[4]Tol = tolyl.

Examples 20 and 21, set out below, are general examples of the chemical reactions able to synthesize the desired compounds modified at amino acid 1 and 3 of CsA using reagents that have the requisite chemical properties, and it would be understood by a person skilled in the art that substitutions of certain reactants may be made.

Example 20: AA1 Modification of Alkylated CsA

Example 20 provides a synthetic route for the introduction of substituents at the 3-position of CsA prior to modification of the AA1 side-chain. Following the 3-alkylation, a 2 step procedure leads to the acetylated aldehyde (compound 3 in the example below), which is a suitable substrate for the modification of the 1-position via Wittig reaction. This method allows introduction of residues to the AA1 side-chain that have limited stability under the reaction conditions used in steps 1-3, such as strong base and oxidizing agents.

Further examples of compounds prepared using this sequence is summarized in Table 2.

Step 1: Alkylation of AA3 Side-Chain

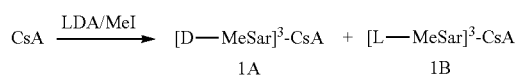

Synthesis is carried out according to Route A or B, respectively, as described above.

Step 2: Acetylation of the Hydroxy-Group on AA1 Side-Chain

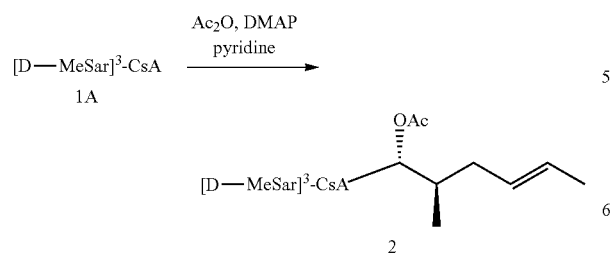

An oven dried flask is charged under nitrogen with [D-MeSar]$^3$-CsA (1.84 g, 1.51 mmol), N,N-dimethylaminopyridine (19 mg, 0.15 mmol) and 20 mL anhydrous pyridine, followed by acetic anhydride (10 mL, 0.1 mol). The reaction is stirred at ambient temperature over night. The mixture is poured into 100 mL ice-water and is stirred until all ice has melted. A solid is collected by filtration and dried in air. The solid is dissolved in 50 mL EtOAc and is washed with 1 M HCl (2×), sat. NaHCO$_3$ solution and brine. The organic phase is dried over Na$_2$SO$_4$ and evaporated. The crude product is purified over silica gel (hexane/EtOAc/MeOH 10:10:0.5).

Step 3: Aldehyde Formation

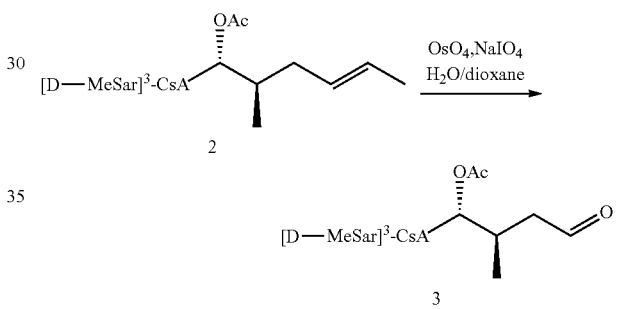

To a flask containing compound 2 (800 mg, 0.636 mmol) are added 10 mL dioxane and 10 mL H$_2$O. NaIO$_4$ (544 mg, 2.54 mmol) and OsO$_4$ (7.9 mM solution in water/dioxane 1:1, 4.05 mL, 32 mmol) are added and the reaction is stirred at room temperature over night 75 mL H$_2$O is added and the reaction is extracted with 3×25 mL EtOAc. The extracts are washed with water, sat. NaHCO$_3$ solution, water and brine (25 mL each) and are dried over MgSO$_4$. The solvent is removed in vacuum and the crude product is purified over silica gel (hexane/EtOAc 3:1).

Step 4: Wittig Reaction

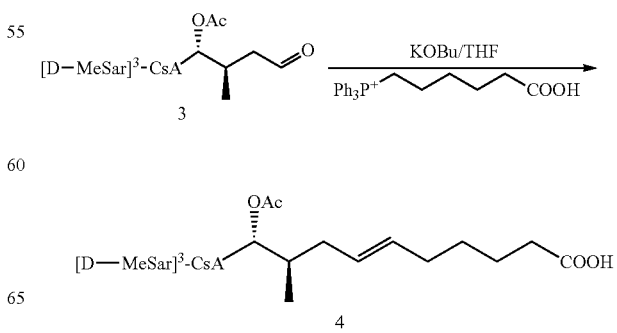

An oven dried flask Is charged under argon atmosphere with triphenyl-6-hexanoic acid phosphonium bromide (90 mg, 0.195 mmol) and 5 mL anhydrous THF. Potassium t-butoxide (1 M solution in THF, 0.39 mL, 0.39 mmol) is added at 0° C. and the solution is stirred for 30 minutes to give a bright orange color. Compound 3 (81 mg, 0.065 mmol, dissolved in 1 mL anhydrous THF) is added to the reaction drop-wise and stirring is continued at room temperature over night. The reaction is quenched with sat. NH$_4$Cl solution and is extracted with EtOAc. The extract is washed with brine and dried over Na$_2$SO$_4$. The solvent is removed in vacuum and the crude product is purified over silica gel (toluene/acetone 3:1).

Step 5: Deacetylation

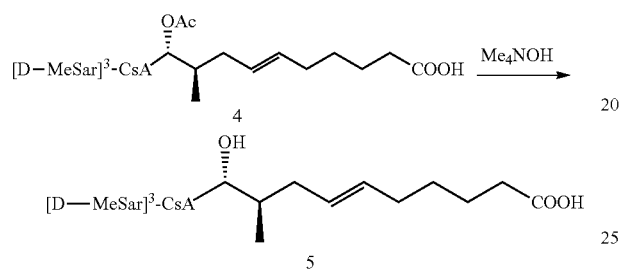

Compound 4 (30 mg, 0.022 mmol) is dissolved in 2 mL methanol and 0.5 mL water and tetramethylammonium hydroxide pentahydrate (12 mg, 0.066 mmol) Is added. The reaction is stirred at room temperature for several days until HPLC confirms deprotection is complete. The reaction is acidified to pH 2 with 1 M HCl and concentrated in a vacuum. The residue is taken up in EtOAc, is washed with water and dried over Na$_2$SO$_4$. The solvent is evaporated and the crude product is purified by preparative HPLC.

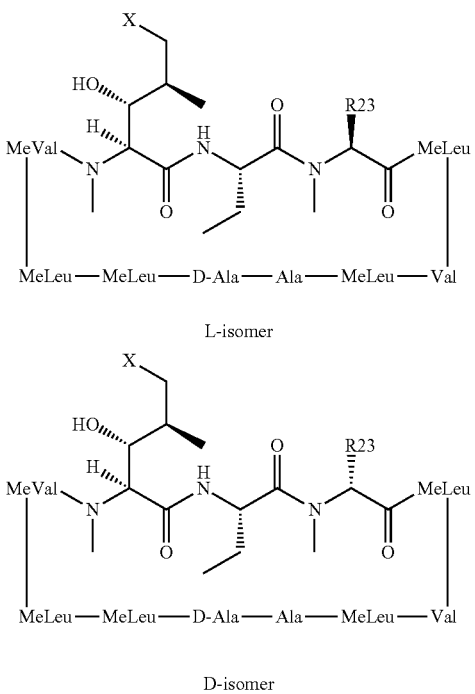

Schematic Representation of 1,3-Modified Cyclosporin Derivatives.

Using the method of Example 20, the following compounds are further examples of the compounds that may be synthesized (X and Y in reference to the above schematic representation; and reference of R in X is to indicate attachment of structure to AA1 of CsA).

TABLE 2

| Compound | X | R23 | Isomer | MS (Na$^+$) |
|---|---|---|---|---|
| 431-13 | R⌒═⌒COOH | —CH$_3$ | L | 1296.8 |
| 414-64 | R⌒═⌒⌒COOH | —CH$_3$ | D | 1325.0 |
| 431-19 | R⌒═⌒⌒COOH | —CH$_3$ | L | 1324.8 |
| 431-40 | R⌒═⌒⌒COOH | —CH$_2$CH$_3$ | D | 1338.8 |
| 440-02 | R⌒═⌒⌒⌒COOH | —CH$_3$ | D | 1327.1 |
| 431-20 | R⌒═⌒⌒⌒COOH | —CH$_3$ | L | 1326.9 |
| 440-13 | R⌒═⌒⌒⌒COOH | —CH$_2$CH$_3$ | D | 1341.1 |
| 431-21 | R⌒═⌒CN | —CH$_3$ | D | 1277.9 |
| 431-44 | R⌒═⌒CN | —CH$_2$CH$_3$ | L | 1291.9 |
| 440-14 | R⌒═⌒CN | —CH$_2$CH$_3$ | D | 1292.0 |

TABLE 2-continued

| Compound | X | R23 | Isomer | MS (Na+) |
|---|---|---|---|---|
| 431-136 | R–CH2CH2–C(=O)–CH2CH3 | —CH3 | L | 1283.1 |
| 440-24 | R–CH2CH2–C(=O)–CH2CH3 | —CH3 | D | 1283.1 |
| 440-10-1 | R–CH2CH2–COOH | —CH3 | D | 1270.9 |
| 440-22-1 | R–CH2CH2–COOH | —CH2CH3 | D | 1285.0 |
| 440-20 | R–CH2CH2–(CH2)9COOH | —CH3 | D | 1397.2 |

Alkylation of AA1 Modified Compounds

Reaction 21 introduces substituents to the AA3 residue of compounds previously modified on the AA1 side-chain. In addition to the groups available through Reaction 19, this route allows the introduction of substituents at AA3 that are unstable under the reaction conditions used in Reaction 20, e.g. a thiomethyl residue could undergo oxidation during the formation of the aldehyde in step 3 of this method.

Example 21

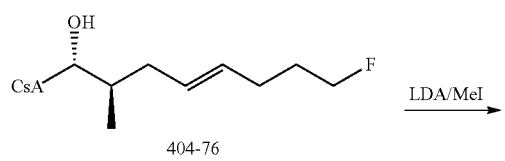

404-76

LDA/MeI

-continued

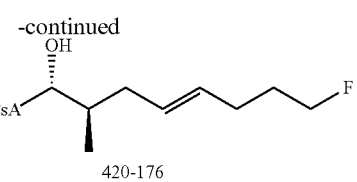

420-176

A dry 25 mL flask is charged under argon atmosphere with 1.5 mL anhydrous THF and diisopropylamine (87 µL, 0.62 mmol). The solution is cooled to 0° C. and n-butyl lithium (2.5 M in hexane, 0.25 mL, 0.62 mmol) is added. The mixture is stirred for 20 minutes at 0° C. and is ten cooled to −70° C. The clear LDA solution is transferred into a solution of 404-76 (118 mg, 0.095 mmol) and lithium chloride (120 mg, 2.84 mmol) in 1.5 mL anhydrous THF at −70° C. Stirring is continued for 2 hours at −70° C. Additional n-butyl lithium (0.23 mL, 0.58 mmol) is added, followed by methyl iodide (118 µL, 1.89 mmol). The reaction is allowed to warm to −20° C. and is kept at this temperature over night. The reaction is quenched with sat. NH4Cl solution and is extracted with EtOAc. The extract is washed with brine, dried over Na2SO4 and evaporated to dryness. The crude product is purified over silica gel (hexane/acetone 3:1→2:1).

TABLE 3

Examples of compounds prepared by Method 21 (X and Y according to FIG. 3; and refperence of R in X is to indicate attachment of structure to AA1 of CsA).

| Compound | X | R23 | Isomer | MS (Na+) |
|---|---|---|---|---|
| 420-176-1 | R–CH=CH–CH2CH2CH2–F | —CH3 | D | 1284.9 |
| 420-176-2 | R–CH=CH–CH2CH2CH2–F | —CH3 | L | 1284.9 |
| 420-177-1 | R–CH2CH2CH2CH2–COOH | —CH3 | D | 1298.8 |
| 420-177-2 | R–CH2CH2CH2CH2–COOH | —CH3 | L | 1298.8 |
| 420-180-1 | R–CH2CH2–Ph | —CH3 | D | 1302.8 |

TABLE 3-continued

Examples of compounds prepared by Method 21 (X and Y according to FIG. 3; and refperence of R in X is to indicate attachment of structure to AA1 of CsA).

| Compound | X | R23 | Isomer | MS (Na⁺) |
|---|---|---|---|---|
| 420-182-1 | R—CH(OH)—CH₂—CH(OH)—CH₃ (branched, OH down) | —CH₃ | D | 1270.8 |
| 420-182-2 | R—CH₂—CH₂—CH(OH)—CH₃ | —CH₃ | L | 1270.8 |
| 420-186 | R—CH=CH—(CH₂)₉COOH | —CH₂CH₃ | L | 1409.0 |
| 431-42 | R—CH=CH—CH₂—COOH | —SCH₃ | D/L [1] | 1328.8 |
| 440-03 | R—(CH₂)₆—F | —SCH₃ | D | 1319.1 |
| 440-78 | R—CH=CH—CH₂—COOH | —(CH₂)₃N⁺(CH₃)₃ | D/L [1] | 1359.9 [2] |
| 440-34-3 | R—(CH₂)₃—C(=O)—NEt₂ | —CH₂—C₆H₅ | D | 1416.2 |
| 440-36 | R—CH=CH—CH=CH₂ | —CH₃ | D | 1251.1 |

[1] isomers not separated;
[2] m⁺ signal.

Additional modifications to the functional groups at AA1 (or AA3, respectively) residue can be carried out to obtain various derivative compounds, such as esters, amides, alcohols etc. Saturated compounds can be obtained by reducing the double bond created in the Wittig reaction.

Example 22: Amide Formation from Carboxylic Acid—Synthesis of 440-08

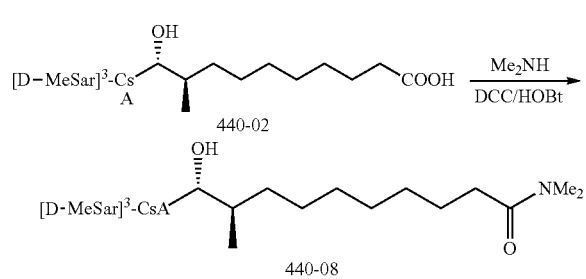

440-02 (48 mg, 0.037 mmol) is dissolved under nitrogen atmosphere in 5 mL anhydrous DCM and cooled to 0° C. Dicyclohexylcarbodiimide (DCC, 11.6 mg, 0.056 mmol) and 1-hydroxybenzotriazole (HOBt, 5.0 mg, 0.037 mmol) are added and the mixture is stirred for 15 minutes at 0° C. Dimethylamine (2 M solution in THF, 0.19 mL, 0.38 mmol) is added and stirring is continued at room temperature for 3 days. The reaction is diluted with 20 mL DCM and washed with 15 mL 0.5 M HCl. The organic phase is dried over $NaSO_4$ and then brought to dryness. The crude mixture is purified by preparative HPLC.

Example 23: Ester Formation—Synthesis of 440-31

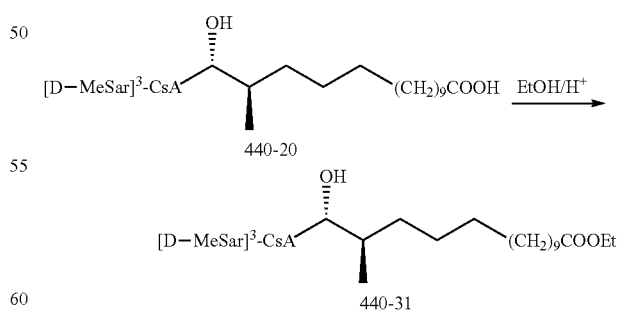

440-20 (30 mg, 0.022 mmol) is dissolved in 4 mL anhydrous EtOH and 2 μL of conc. $H_2SO_4$. The reaction is heated to reflux for 3 hours and is then allowed to cool to room temperature. The reaction is brought to dryness. The crude product is purified by preparative HPLC.

Example 24: Amide Formation from Nitrile Compound (Reversed Amide)—Synthesis of 440-15

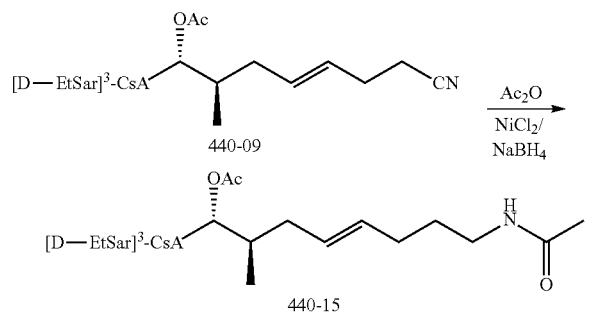

A 50 mL flask is charged under nitrogen with 440-09 (80 mg, 0.061 mmol) and 5 mL MeOH. The reaction is cooled to 0° C. and Ni(II)Cl$_2$.6H$_2$O (1.4 mg, 0.006 mmol) and acetic anhydride (19 μL, 0.20 mmol) are added. Sodium borohydride (104 mg, 2.75 mmol) is added in 2 batched 2 hours apart. The reaction is then allowed to warm to room temperature and is stirred over night. After the reaction is complete, 7 mL 1 M HCl is added. The solution is concentrated in vacuum to approximately half of its original volume. The resulting mixture is extracted with EtOAc, the extract is washed with sat. NaHCO$_3$ solution and brine and is dried over Na$_2$SO$_4$. The solvent is removed in vacuum. The product, which contains some saturated compound, is used in the following step without further purification.

Example 25: Synthesis of 440-25

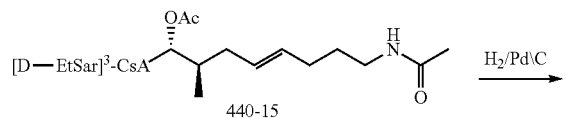

440-15 (83 mg, 0.061 mmol) is dissolved in 10 mL anhydrous EtOH. Palladium (10 wt % on Carbon, 8 mg) and 3-4 drops of acetic acid are added. The reaction is hydrogenated under atmospheric pressure at room temperature for several days until complete by HPLC. The reaction is filtered through Celite and the filtrate is evaporated to dryness. The crude product is purified by prep. HPLC and is then subjected to the deacetylation step.

Example 26: Synthesis of 440-32

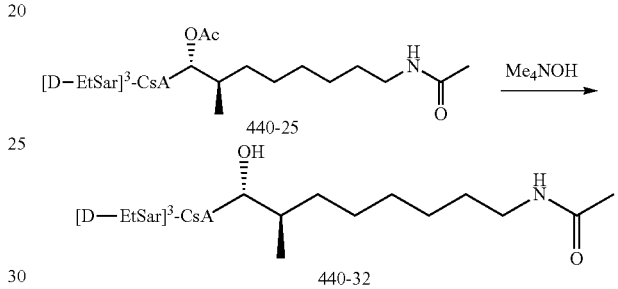

440-25 (41 mg, 0.03 mmol) is dissolved in 4 mL MeOH and tetramethylammonium hydroxide pentahydrate (16 mg, 0.09 mmol, dissolved in 1 mL H$_2$O) is added. The reaction is stirred at room temperature for 2 days. The reaction is concentrated in vacuum. 5 mL H$_2$O is added and the product is extracted with EtOAc. The extract is washed with brine, dried over Na$_2$SO$_4$ and evaporated to dryness. The crude product is purified by preparative HPLC.

Table 4: Examples of Derivatives of 1,3-Modified Cyclosporin Compounds Obtained by Reducing the Double Bond Created in the Wittig Reaction (X and Y According to FIG. 3; and Reference of R in X is to Indicate Attachment of Structure to AA1 of CsA).

| Compound | X | R23 | Isomer | MS (Na$^+$) |
|---|---|---|---|---|
| 431-23 | R⌒⌒C(=O)NMe$_2$ (with double bond) | —CH$_3$ | L | 1323.8 |
| 431-29 | R⌒⌒C(=O)-morpholine (with double bond) | —CH$_3$ | L | 1393.9 |
| 440-08 | R⌒⌒⌒C(=O)NMe$_2$ | —CH$_3$ | D | 1354.1 |
| 440-27 | R⌒⌒⌒C(=O)NMe$_2$ | —CH$_2$CH$_3$ | D | 1368.1 |

-continued

| Compound | X | R23 | Isomer | MS (Na$^+$) |
|---|---|---|---|---|
| 440-23 | R—(CH$_2$)$_9$—C(=O)—NMe$_2$ | —CH$_3$ | D | 1424.2 |
| 431-32 | R—(CH$_2$)$_5$—NH—C(=O)—CH$_3$ | —CH$_3$ | D | 1325.9 |
| 431-53 | R—(CH$_2$)$_5$—NH—C(=O)—CH$_3$ | —CH$_2$CH$_3$ | L | 1339.9 |
| 440-32 | R—(CH$_2$)$_5$—NH—C(=O)—CH$_3$ | —CH$_2$CH$_3$ | D | 1340.1 |
| 440-10-2 | R—CH$_2$—CH(COOMe)— | —CH$_3$ | D | 1285.0 |
| 440-22-2 | R—CH$_2$—CH(COOMe)— | —CH$_2$CH$_3$ | D | 1299.1 |
| 440-31 | R—CH$_2$—CH((CH$_2$)$_9$COOEt)— | —CH$_3$ | D | 1425.2 |

Cyclophilin A Isomerase Inhibition Assay

An enzymatic assay was used to measure the inhibition of CyP-A activity by 1,3 CsA analogs of the present invention, according to a protocol described in the scientific literature with minor modifications. The assay is based on the ability of CyP-A to catalyze a conformational change in proline-containing peptides from cis to trans isomeric conformations. Briefly, a peptide substrate that includes a nitroanilide moiety was supplied to a reaction mixture containing CyP-A, test compound (CsA analog, CsA, or dimethylsulfoxide vehicle), and a second enzyme, alpha-chymotrypsin. Each test compound was tested at 10 concentrations in triplicate or quadruplicate. The peptide was converted from the cis conformation to the trans conformation both by non-catalytic and CyP catalytic processes. The trans isomer of the peptide, but not the cis isomer, is a substrate for alpha-chymotrypsin. Alpha-chymotrypsin immediately cleaved nitroanilide from the rest of the peptide, and free nitroanilide accumulated at a rate proportional to cis-trans isomerization. Since free nitroanilide is a colored product, its accumulation was quantified by measuring its absorbance with a spectrophotometer. Nitroanilide accumulation was measured for 6 minutes, and first order rate constants for each reaction were calculated using Graphpad Prism software. The CyP-A catalytic rate constant of each reaction was determined by subtracting the non-catalytic rate constant (derived from the reaction without CyP-A) from the total reaction rate constant. Plots of the catalytic rate constants as a function of inhibitor concentrations demonstrated the compounds' potencies, defined by their IC$_{50}$ values.

Detailed Protocol

A. Peptide

The assay peptide was N-succinyl-alanine-alanine-proline-phenylalanine-p-nitroanilide. It was dissolved to a concentration of 3 mM in a solution of trifluoroethanolamine and lithium chloride (TFE/LiCl). TFE/LiCl was prepared fresh each day by dissolving lithium chloride in trifluoroethanolamine to a concentration of 17 mg/ml. Following dissolution of LiCl, the water content of the TFE/LiCl solution was reduced by adding heat-dried molecular sieves and gentle mixing the solution for at least 30 minutes. The peptide was then dissolved in TFE/LiCl, and the solution cooled to 4° C.-8° C. prior to the assays. Dissolution of the peptide in dry TFE/LiCl promoted more peptide to exist in the cis conformation at the beginning of each assay reaction. Data analysis showed that approximately 60% of the peptide in our assays began as a c/s isomer which Is consistent with reported data in the scientific literature. In the enzyme reactions the peptide was diluted 20-fold to a final assay concentration of 150 μM.

B. Test Compounds

The test compounds consisted of CsA, CsA analogs, or dimethylsulfoxide (DMSO). Stock solutions of CsA and CsA analogs were made by dissolution in DMSO to a concentration of 10 mg/ml in sterile microcentrifuge tubes. Stock solutions were stored at −20° C. when not in use. Further dilutions of the test compounds were made on each day of the assays. DMSO and CsA were tested in every experiment to serve as the vehicle control and reference compound, respectively.

The 10 mg/ml stock solutions of CsA and CsA analogs were diluted with DMSO to 50 μM in microcentrifuge tubes, based on the molecular weights of the compounds. Nine 3-fold serial dilutions of each compound in DMSO were then made in a 96-well polystyrene plate. An aliquot of DMSO-solution or DMSO vehicle alone was diluted 50-fold in reaction buffer (see below for recipe) to make final concentrations of CsA or CSA ANALOGs of 1000, 333, 111, 37, 12, 4.1, 1.4, 0.46, 0.15, and 0.05 nM. The reaction buffer solutions were stored at 4° C.-8° C. for at least one hour prior to the assays C. Reaction Buffer The starting solution (saline buffer) for the reaction buffer consisted of Hepes 50 mM, sodium chloride 100 mM, and human serum albumin 1 mg/ml, adjusted to pH 8.0 with sodium hydroxide. The saline buffer was stored at 4° C. when not in use. On each assay day bovine alpha-chymotrypsin was dissolved in a volume of saline buffer to a concentration of 1 mg/ml. An aliquot of the alpha-chymotrypsin solution was removed to serve as the noncatalytic control reaction buffer. Recombinant human CyP-A was added to the remainder of the chymotrypsin solution to a concentration of 5 nM. The solution containing alpha-chymotrypsin and CyP-A was designated the reaction buffer and was used for preparation of the reaction solutions.

D. Reaction Protocol

All assay reactions were conducted in a cold room within a temperature range of 4° C.-8° C. All solutions and equipment were stored in the cold room for at least 1 hour prior to the assays. The low temperature was necessary for reactions to proceed at a sufficiently slow rate to measure with the available equipment. The measuring device was a BMG Polarstar microplate reader configured for absorbance readings at OD 405 nm. Reactions were performed in 96-well, flat-bottom, polystyrene assay plates. Each assay run consisted of 12 separate reactions in one row of the plate. Peptide was aliquoted at 5 µl per well with a single-channel pipettor in one row of the plate, then the plate placed in the plate holder of the microplate reader. Reactions were begun by dispensing 95 µl of reaction buffer into each peptide-containing well using a 12-channel pipettor and mixing each reaction thoroughly by repeat pipetting to ensure uniform dissolution of the peptide. The 12 reactions in each assay run were represented by the following:

a) 10 reactions, representing one replicate for each of the 10 concentrations of one test compound (CyP-A in reaction buffer)
b) 1 reaction with 5 µl DMSO vehicle (CyP-A in reaction buffer)
c) 1 reaction with 5 µl DMSO vehicle (CyP-A A absent from reaction buffer)

Absorbance recordings were begun immediately after mixing. Approximately 15 seconds elapsed from addition of the reaction buffer to the first $OD_{405}$ recording due to mixing time and instrument setup. Subsequent readings were made at 6-second intervals for a total of 60 readings over 360 seconds. Three or four reaction runs were made for each test compound to provide data replicates.

E. Data Analysis

The raw data consisted of a time-dependent increase in $OD_{405}$. In the presence of CyP-A and the absence of inhibitor the peptide was completely converted to the trans isomer within approximately 150 seconds as demonstrated by a plateau in the $OD_{405}$. $OD_{405}$ vs. time data were plotted with Graphpad Prism software and fitted with a one phase exponential equation to derive a first order rate constant K for each reaction. In reactions without CyP-A, the rate constant entirely represented the spontaneous noncatalytic, thermal cis-to-trans isomerization of the peptide and was defined as the noncatalytic rate constant $K_0$. In reactions containing CyP-A, isomerization occurred both through noncatalytic and enzyme-catalyzed processes. Thus, the rate constant K in CyP-A-containing reactions represented the sum of the noncatalytic rate constant $K_0$ and the catalytic rate constant $K_{cat}$. $K_{cat}$ was calculated by subtracting $K_0$ (obtained from the reaction without CyP-A) from the total rate constant K. $K_{cat}$ typically was 3-fold higher than $K_0$ in reactions with 5 nM CyP-A, 150 µM peptide substrate, and no inhibitor.

Plots of $K_{cat}$ versus inhibitor concentration were fitted with sigmoidal dose-response nonlinear regressions to demonstrate inhibitor potencies. Software-calculated $EC_{50}$ values represented the test compound concentrations that inhibited $K_{cat}$ by 50%. To normalize for inter-experiment variability in assay conditions, CsA was run in every experiment as a reference compound, and CsA analog potency was expressed as a fold-potency relative to CsA based on $EC_{50}$ values. For example, a CsA analog $EC_{50}$ that was ½ of CsA represented a 2-fold potency compared to CsA, whereas a CSA analog $IC_{50}$ that was 5-fold higher than CsA represented a 0.2-fold potency compared to CsA.

Table 5, shown in the attached Figure, shows cyclophilin A inhibition and immunosuppression of CsA analogs modified at position 1 and at positions 1 and 3 according to the present invention.

The invention claimed is:
1. A compound of Formula L:

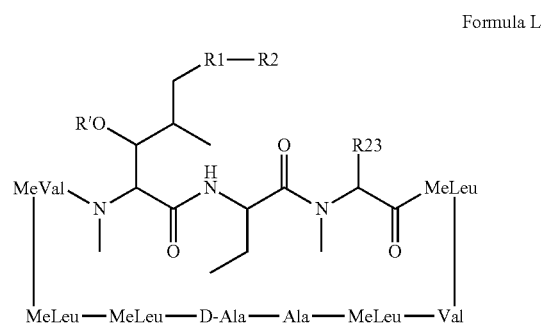

Formula L wherein:
a) R' is H or acetyl;
b) R1 is a saturated or unsaturated straight or branched aliphatic carbon chain from 2 to 15 carbon atoms in length;
c) R2 is selected from the group consisting of:
   i) an unsubstituted, N-substituted, or N,N-disubstituted amide;
   ii) a carboxylic acid;
   iii) a nitrile;
   iv) an ester;
   v) a ketone;
   vi) a hydroxy, dihydroxy, trihydroxy, or polyhydroxy alkyl;
   vii) a substituted or unsubstituted aryl;
   viii) a saturated or unsaturated straight or branched aliphatic carbon chain substituted with a substituent selected from the group consisting of a ketone, a hydroxy, a nitrile, a carboxylic acid, an ester, a 1,3-dioxolane, and an oxo;
   ix) an aromatic group substituted with a substituent selected from the group consisting of a halogen, an ester, and a nitro; and
   x) a combination of the saturated or unsaturated straight or branched aliphatic carbon chain of viii) and the aromatic group of ix); and
d) R23 is unsubstituted $C_1$-$C_3$ alkyl.

2. The compound of claim 1, wherein R1-R2 is selected from the group consisting of:
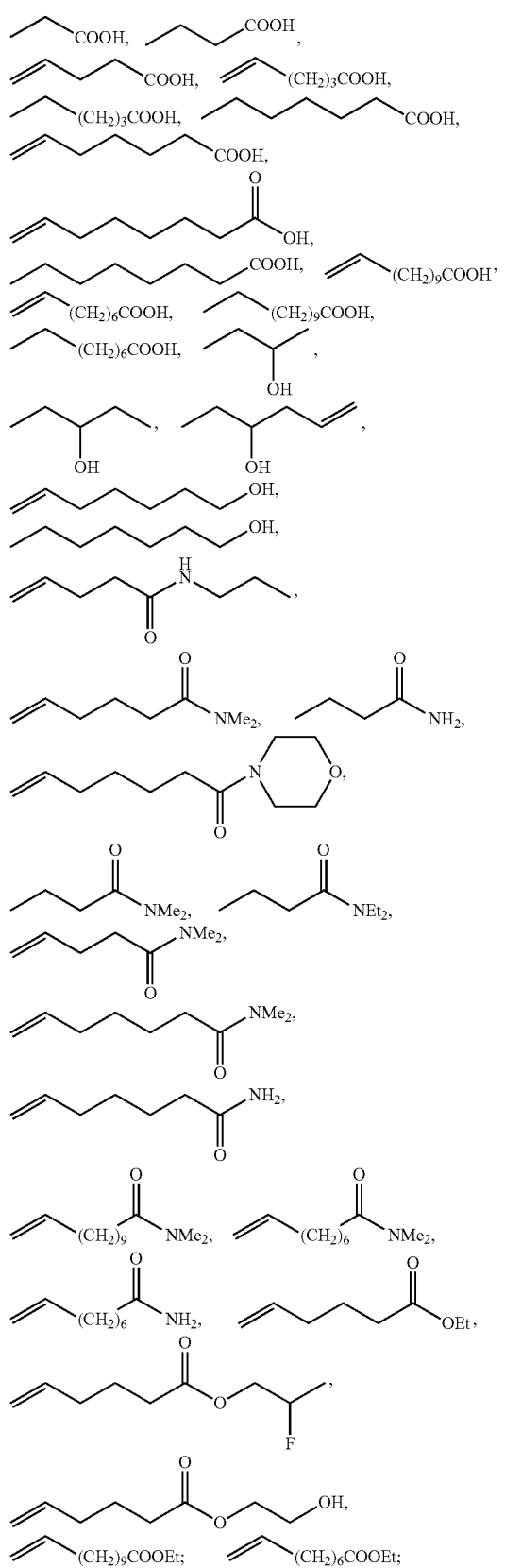
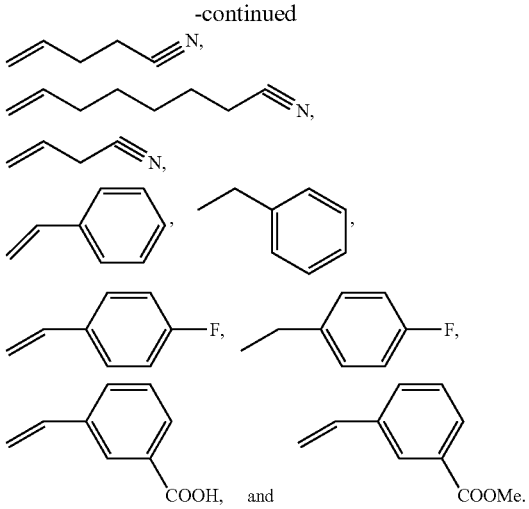
3. The compound of claim 1, wherein R2 is selected from the group consisting of:
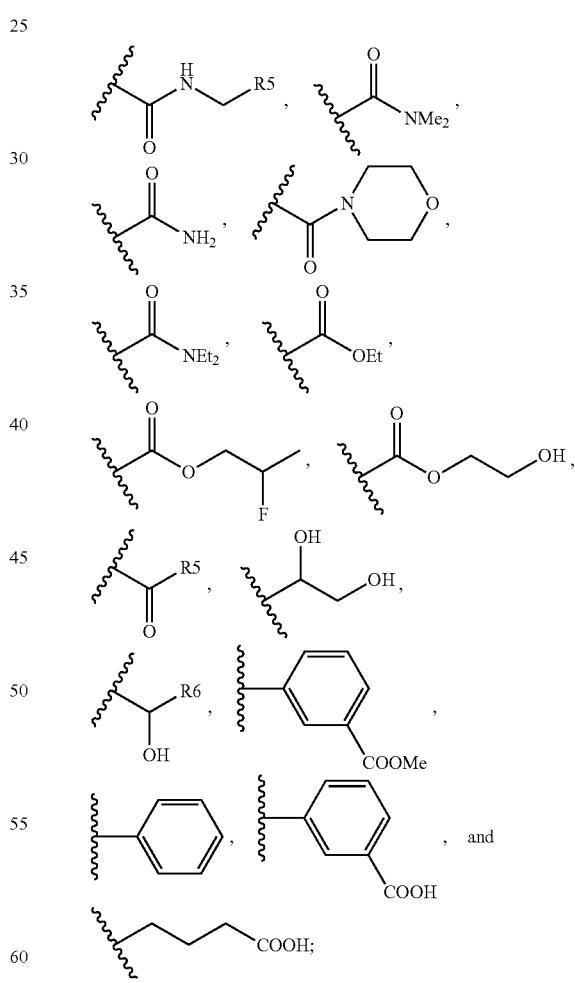
wherein:
R5 is a saturated or unsaturated straight or branched aliphatic carbon chain between 1 and 10 carbons in length; and R6 is a monohydroxylated, dihydroxylated, trihydroxylated, or polyhydroxylated saturated or unsaturated straight or branched aliphatic carbon chain between 1 and 10 carbons in length.

4. The compound of claim 1, wherein R1 is a saturated or unsaturated straight or branched aliphatic carbon chain from 5 to 8 carbon atoms in length.

5. The compound of claim 1, wherein R' is H.

6. The compound of claim 1, wherein R1-R2 is substituted with a substituent selected from the group consisting of a ketone, a hydroxy, a nitrile, an oxo, a carboxylic acid, an ester, and a 1,3-dioxolane.

7. The compound of claim 1, wherein R23 is selected from the group consisting of:
—CH$_3$ and —CH$_2$CH$_3$.

8. The compound of claim 1, wherein the compound comprises the D-epimer of amino acid 3 which is the amino acid to which R23 is attached.

9. The compound of claim 1, wherein R23 is methyl.

10. The compound of claim 1, wherein

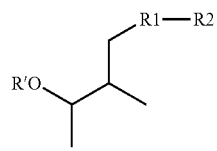

in Formula L is selected from the group consisting of:

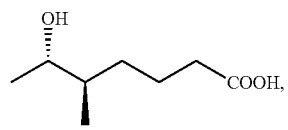

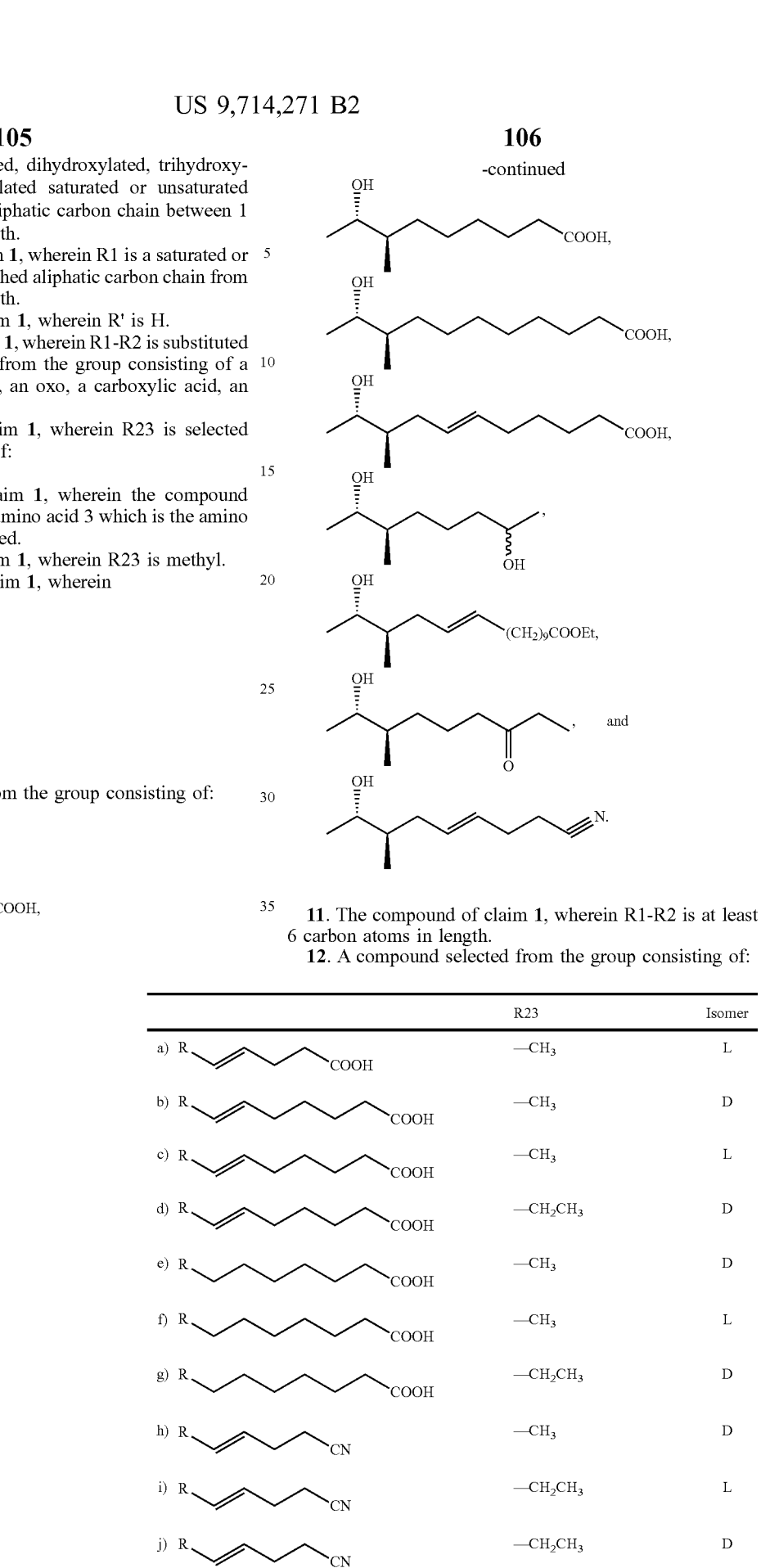

11. The compound of claim 1, wherein R1-R2 is at least 6 carbon atoms in length.

12. A compound selected from the group consisting of:

|  |  | R23 | Isomer |
|---|---|---|---|
| a) | R⎯⎯COOH | —CH$_3$ | L |
| b) | R⎯⎯COOH | —CH$_3$ | D |
| c) | R⎯⎯COOH | —CH$_3$ | L |
| d) | R⎯⎯COOH | —CH$_2$CH$_3$ | D |
| e) | R⎯⎯COOH | —CH$_3$ | D |
| f) | R⎯⎯COOH | —CH$_3$ | L |
| g) | R⎯⎯COOH | —CH$_2$CH$_3$ | D |
| h) | R⎯⎯CN | —CH$_3$ | D |
| i) | R⎯⎯CN | —CH$_2$CH$_3$ | L |
| j) | R⎯⎯CN | —CH$_2$CH$_3$ | D |

-continued
| | | R23 | Isomer |
|---|---|---|---|
| k) | 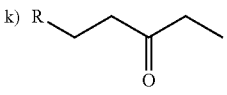 | —CH₃ | L |
| l) | 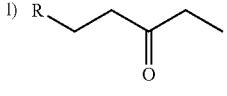 | —CH₃ | D |
| m) | 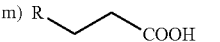 | —CH₃ | D |
| n) | 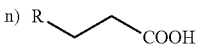 | —CH₂CH₃ | D |
| o) | 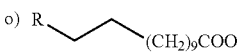 | —CH₃ | D |
| r) | 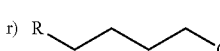 | —CH₃ | D |
| s) |  | —CH₃ | L |
| t) | 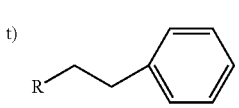 | —CH₃ | D |
| u) | 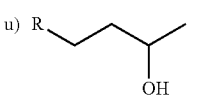 | —CH₃ | D |
| v) | 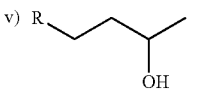 | —CH₃ | L |
| w) | 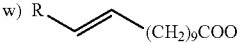 | —CH₂CH₃ | L |
| x) | 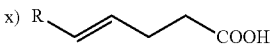 | —SCH₃ | D/L |
| z) |  | —(CH₂)₃N⁺(CH₃)₃ | D/L |
| aa) | 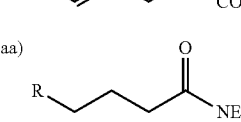 | 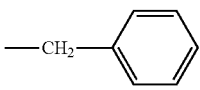 | D |
| bb) | 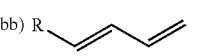 | —CH₃ | D |
| cc) | 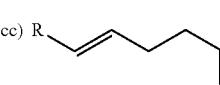 | —CH₃ | L |
| dd) | 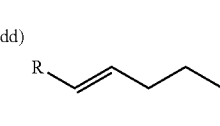 | —CH₃ | L |
| ee) | 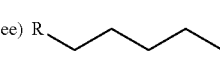 | —CH₃ | D |

-continued

| | | R23 | Isomer |
|---|---|---|---|
| ff) | R~~~~~~~NMe₂ (with C=O) | —CH₂CH₃ | D |
| gg) | R—(CH₂)₉—C(=O)—NMe₂ | —CH₃ | D |
| hh) | R~~~COOMe | —CH₃ | D |
| ii) | R~~~COOMe | —CH₂CH₃ | D |
| jj) | R~~~(CH₂)₉COOEt | —CH₃ | D | wherein:
R is

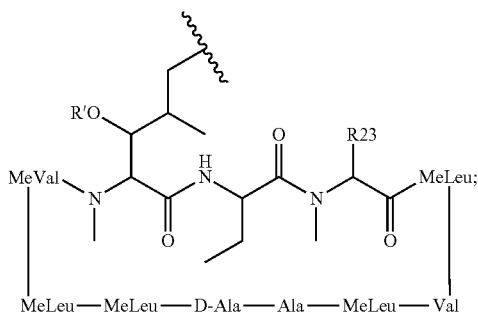

MeLeu—MeLeu—D-Ala—Ala—MeLeu—Val

R' is H or acetyl,
and wherein the isomer is the isomeric form of amino acid 3 which is the amino acid to which R23 is attached.

13. A pharmaceutical composition comprising the compound of claim 1 and one or more pharmaceutical excipients.

14. A method of treating or preventing a cyclophilin mediated disease or injury in a mammal comprising administering the compound of claim 1 to the mammal.

15. The method of claim 14, wherein the disease or injury is mediated by the over-expression of cyclophilin or the disease is a congenital over-expression of cyclophillin.

16. The method of claim 14, wherein the cyclophilin mediated disease or injury is selected from the group consisting of a viral infection; inflammatory disease; cancer; muscular disorder; neurological disorder; and injury associated with ischemia, reperfusion, loss of cellular calcium homeostasis, loss of ionic homeostasis, increase in free radical production, or toxins that induce mitochondrial dysfunction;
   wherein the viral infection is optionally caused by a virus selected from the group consisting of Human Immunodeficiency Virus, Hepatitis A, Hepatitis B, Hepatitis C, Hepatitis D, Hepatitis E, SARS-CoV, hCoV-NL63, hCoV-HKU-1, hCoV-OC43, hCOV-229E, coronavirus, feline infectious peritonitis virus, and transmissible gastroenteritis virus;
   wherein the inflammatory disease is optionally selected from the group consisting of asthma, autoimmune disease, chronic inflammation, chronic prostatitis, glomerulonephritis, hypersensitivity disease, inflammatory bowel disease, sepsis, vascular smooth muscle cell disease, aneurysms, pelvic inflammatory disease, reperfusion injury, rheumatoid arthritis, transplant rejection, and vasculitis;
   wherein the cancer is optionally selected from the group consisting of small and non-small cell lung cancer, bladder cancer, hepatocellular cancer, pancreatic cancer, breast cancer, glioblastoma, colorectal cancer, squamous cell carcinoma, melanoma, and prostate cancer;
   wherein the muscular disorder is optionally selected from the group consisting of myocardial reperfusion injury, muscular dystrophy, collagen VI myopathies, Post-cardiac arrest syndrome (PCAS), heart failure, atherosclerosis, and abdominal aortic aneurysm;
   wherein the neurological disorder is optionally selected from the group consisting of Alzheimer's disease, Parkinson's disease, Huntington's disease, multiple systems atrophy, multiple sclerosis, cerebral palsy, epilepsy, stroke, diabetic neuropathy, amyotrophic lateral sclerosis (Lou Gehrig's Disease), bipolar disorder, excitotoxic injury, hepatic encephalopathy, hypoglycemia, manganese toxicity, neuronal target deprivation, toxic fatty acids, mechanical nerve injury, spinal cord injury, and cerebral injury; and
   wherein the injury associated with loss of cellular calcium homeostasis is optionally selected from the group consisting of myocardial infarct, stroke, acute hepatotoxicity, cholestasis, and storage/reperfusion injury of transplant organs.

17. The method of claim 16, wherein the toxic fatty acid is arachadonic acid.

18. A process for the preparation of a compound of Formula L:

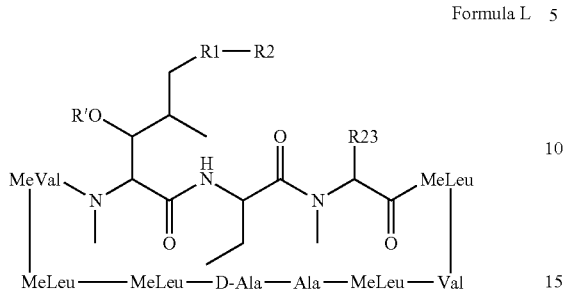

Formula L wherein:
a) R' is H or acetyl;
b) R1 is a saturated or unsaturated straight or branched aliphatic carbon chain from 2 to 15 carbon atoms in length;
c) R2 is selected from the group consisting of:
 i) an unsubstituted, N-substituted, or N,N-disubstituted amide;
 ii) a carboxylic acid;
 iii) a nitrile;
 iv) an ester;
 v) a ketone;
 vi) a hydroxy, dihydroxy, trihydroxy, or polyhydroxy alkyl;
 vii) a substituted or unsubstituted aryl;
 viii) a saturated or unsaturated straight or branched aliphatic carbon chain substituted with a substituent selected from the group consisting of a ketone, a hydroxy, a nitrile, a carboxylic acid, an ester, a 1,3-dioxolane, and an oxo;
 ix) an aromatic group substituted with a substituent selected from the group consisting of a halogen, an ester, and a nitro; and
 x) a combination of the saturated or unsaturated straight or branched aliphatic carbon chain of viii) and the aromatic group of ix); and
d) R23 is a saturated or unsaturated straight or branched optionally substituted aliphatic carbon chain,
comprising the steps of:
1) reacting cyclosporin-A (CsA) with a basic lithium alkylamide, in the presence of a suitable solvent optionally with LiCl, followed by reaction with a suitable electrophile to generate a compound of Formula 1:

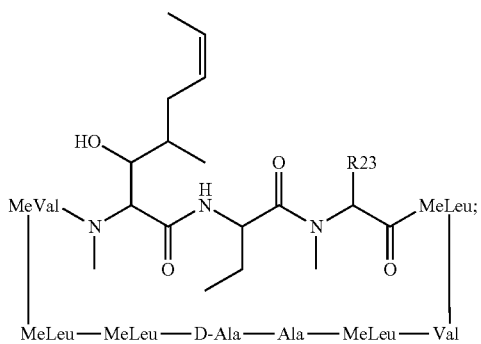

Formula 1

2) reacting the compound of Formula 1 with Ac₂O in the presence of a suitable solvent to form a compound of Formula 2A:

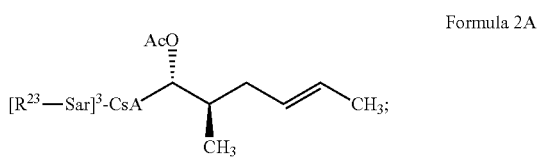

Formula 2A 3) reacting the compound of Formula 2A with an oxidant to form a compound of Formula 3A:

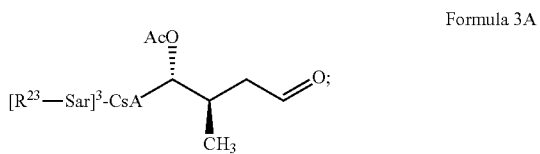

Formula 3A 4) reacting the compound of Formula 3A with an electrophile to form a compound of Formula 4A:

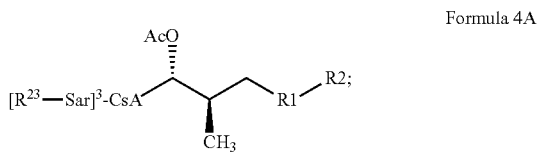

Formula 4A and
5) optionally deacylating the compound of Formula 4A.

19. The process of claim 18, wherein the preparation of the compound of Formula L comprises the addition of an excess of LiCl in the suitable solvent in step 1) to form predominantly the L-epimer of the compound of Formula L, or the preparation of the compound of Formula L is carried out in the absence of LiCl in the suitable solvent in step 1) to form predominantly the D-epimer of the compound of Formula L, wherein the chiral center of the L-epimer or the D-epimer of the compound of Formula L is the carbon atom to which R23 is attached.

20. The process of claim 18, wherein the basic lithium alkylamide is lithium diisopropylamide.

21. The process of claim 18, wherein the electrophile is selected from the group defined in the following table, to generate the corresponding R23 in the table:

| Electrophile | R23 |
| --- | --- |
| methyl iodide | —CH₃ |
| ethyl iodide | —CH₂CH₃ |
| allyl bromide | —CH₂CHCH₂ |
| 1,3-diiodopropane | —CH₂CH₂CH₂I |
| 1,4-diiodobutane | —(CH₂)₃CH₂I |
| trimethylammonium-3-iodopropane hexafluorophosphate | —(CH₂)₃N⁺(CH₃)₃ |
| propargyl bromide | —CH₂CCH |
| tert-butyl bromoacetate | —CH₂CO₂(t-Bu) |
| benzyl bromide | —CH₂Ph |
| Formaldehyde | —CH₂OH |
| Acetaldehyde | —CH(OH)CH₃ |
| Pivalaldehyde | —CH(OH)(t-Bu) |

-continued

| Electrophile | R23 |
|---|---|
| Benzaldehyde | —CH(OH)Ph |
| carbon dioxide | —COOH |
| dimethyl disulfide | —SCH$_3$ |
| p-tolyl disulfide | —S(p-Tol) |

22. The process of claim 18, wherein R2 is a carboxylic acid and R23 is —CH$_3$.

23. A process for the preparation of the compound of Formula L of claim 1, comprising the steps of:
reacting a compound of Formula 1A with dimethylaminopyridine in the presence of a suitable solvent, to form a compound of Formula 2:

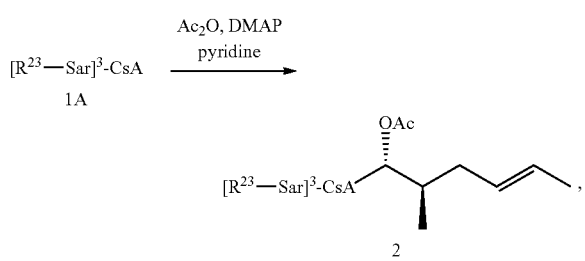

optionally followed by formation of an aldehyde of Formula 3:

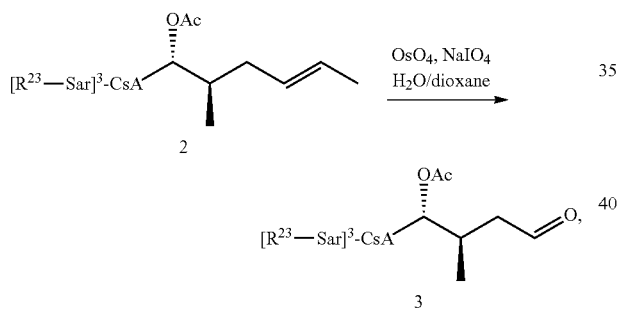

optionally followed by a Wittig reaction to generate the compound of Formula L, wherein R23 is selected from the group consisting of: —CH$_3$ and —CH$_2$CH$_3$.

24. A process for the preparation of the compound of Formula L of claim 1, comprising the steps of:
reacting a compound of Formula 5

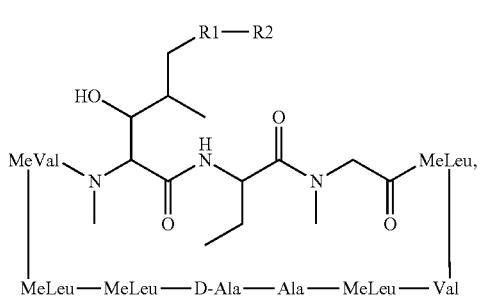

wherein R1 and R2 are as defined in claim 1, with a basic lithium alkylamide, in the presence of a suitable electrophile in an appropriate solvent to form the compound of Formula L, wherein R23 is unsubstituted $C_1$-$C_3$ alkyl.

25. The process of claim 24, wherein the basic lithium alkylamide is lithium diisopropylamide.

26. The process of claim 24, wherein R2 is a carboxylic acid and R23 is —CH$_3$.

27. A compound of Formula L:

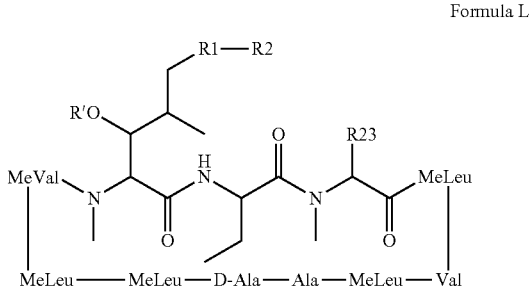

wherein:
a) R' is H or acetyl;
b) R1 is a saturated or unsaturated straight or branched aliphatic carbon chain from 2 to 15 carbon atoms in length;
c) R2 is selected from the group consisting of:
i) an unsubstituted, N-substituted, or N,N-disubstituted amide;
ii) a carboxylic acid;
iii) a nitrile;
iv) an ester;
v) a ketone;
vi) a hydroxy, dihydroxy, trihydroxy, or polyhydroxy alkyl;
vii) a substituted or unsubstituted aryl;
viii) a saturated or unsaturated straight or branched aliphatic carbon chain substituted with a substituent selected from the group consisting of a ketone, a hydroxy, a nitrile, a carboxylic acid, an ester, a 1,3-dioxolane, and an oxo;
ix) an aromatic group substituted with a substituent selected from the group consisting of a halogen, an ester, and a nitro; and
x) a combination of the saturated or unsaturated straight or branched aliphatic carbon chain of viii) and the aromatic group of ix); and
d) R23 is a saturated or unsaturated straight or branched optionally substituted aliphatic carbon chain,
wherein R1-R2 is at least 6 carbon atoms in length.

28. The compound of claim 27, wherein R1-R2 is selected from the group consisting of:

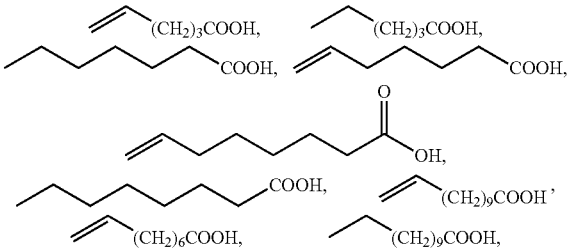

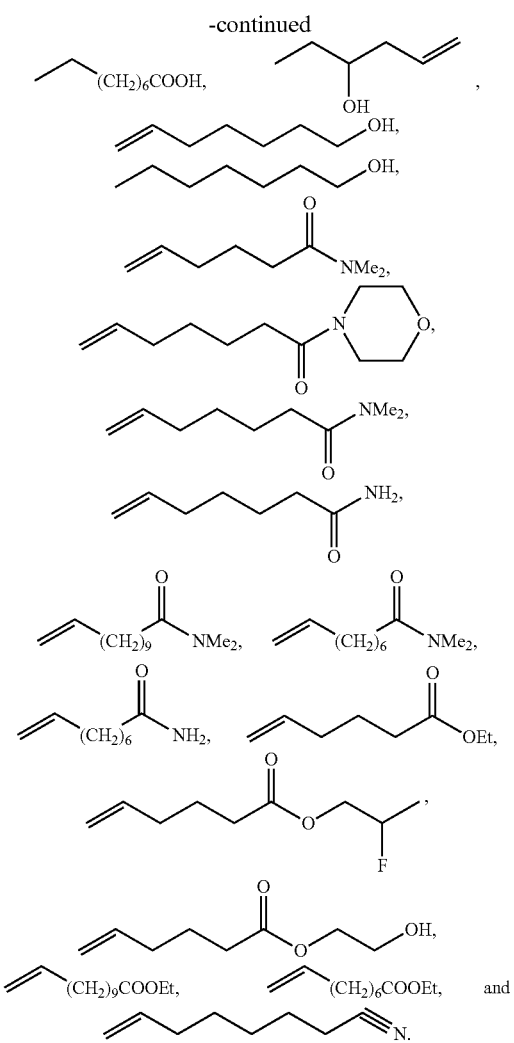

N⁺(CH₃)₃, —CH₂CCH, —CH₂CO₂(t-Bu), —CH₂Ph, —CH₂OH, —CH(OH)CH₃, —CH(OH)(t-Bu), —CH(OH)Ph, —COOH, —SCH₃, and —S(p-Tol).

33. The compound of claim 27, wherein R23 comprises an optionally substituted $C_1$-$C_3$ alkyl.

34. The compound of claim 27, wherein R23 is substituted with amino.

35. The compound of claim 27, wherein R23 is $C_1$-$C_3$ alkyl and the compound comprises the D-epimer of amino acid 3 which is the amino acid to which R23 is attached.

36. The compound of claim 27, wherein R23 is methyl.

37. The compound of claim 27, wherein

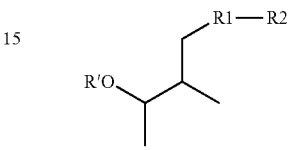

in Formula L is selected from the group consisting of:

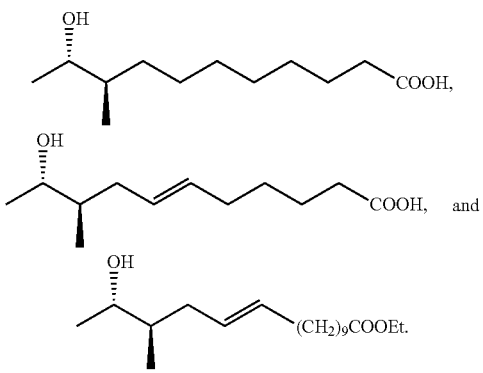

38. The compound of claim 27, wherein R23 is a straight or branched aliphatic carbon chain of 1 to 6 carbons in length.

29. The compound of claim 27, wherein R1 is a saturated or unsaturated straight or branched aliphatic carbon chain from 5 to 8 carbon atoms in length.

30. The compound of claim 27, wherein R' is H.

31. The compound of claim 27, wherein R1-R2 is substituted with a substituent selected from the group consisting of a ketone, a hydroxy, a nitrile, an oxo, a carboxylic acid, an ester, and a 1,3-dioxolane.

32. The compound of claim 27, wherein R23 is selected from the group consisting of: —CH₃, —CH₂CH₃, —CH₂CHCH₂, —CH₂CH₂CH₂I, —(CH₂)₃CH₂I, —(CH₂)₃

39. The compound of claim 1, wherein R1-R2 is

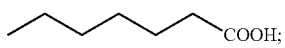

and R23 is methyl, and wherein the compound is a D-epimer, wherein the chiral center of the D-epimer is the carbon to which R23 is attached.

* * * * *

UNITED STATES PATENT AND TRADEMARK OFFICE
CERTIFICATE OF CORRECTION

| | | |
|---|---|---|
| PATENT NO. | : 9,714,271 B2 | Page 1 of 2 |
| APPLICATION NO. | : 14/928885 | |
| DATED | : July 25, 2017 | |
| INVENTOR(S) | : Alexander Hegmans et al. | |

It is certified that error appears in the above-identified patent and that said Letters Patent is hereby corrected as shown below:

On the Title Page

References Cited
OTHER PUBLICATIONS

Page 4, Right-Hand Column, Third Cited Reference:
jin Z. et al. "Cyclophilin A is a secreted growth factor induced by oxidative stress", *Circ. Res.* 30 2000, 87:789-796.

Should read:
--Jin Z. et al. "Cyclophilin A is a secreted growth factor induced by oxidative stress", *Circ. Res.* 30 2000, 87:789-796.--

Page 4, Right-Hand Column, 11$^{th}$ Cited Reference:
Lubart J. et al. "Human immunodeficiency virus type I Gag protein binds to cyclophilins A and B", *Cell* 1993, 73:1067-1078.

Should read:
--Luban J. et al. "Human immunodeficiency virus type I Gag protein binds to cyclophilins A and B", *Cell* 1993, 73:1067-1078.--

In the Claims

At Column 103, Line 15, replace:

Signed and Sealed this
Third Day of October, 2017

Joseph Matal
*Performing the Functions and Duties of the*
*Under Secretary of Commerce for Intellectual Property and*
*Director of the United States Patent and Trademark Office*

With:
-- 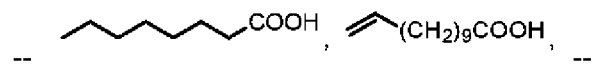 , --
At Column 103, after Line 65, insert:
-- 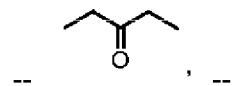 , --
At Column 114, Line 64, replace:
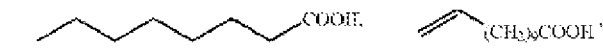
With:
-- 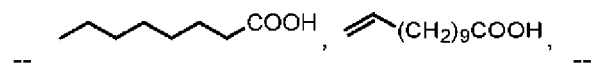 , --